US012784887B2

(12) United States Patent
Athey et al.

(10) Patent No.: US 12,784,887 B2
(45) Date of Patent: *Nov. 3, 2026

(54) METHODS AND SYSTEM FOR THE RECONSTRUCTION OF DRUG RESPONSE AND DISEASE NETWORKS AND USES THEREOF

(71) Applicant: REGENTS OF THE UNIVERSITY OF MICHIGAN, Ann Arbor, MI (US)

(72) Inventors: Brian D. Athey, Ann Arbor, MI (US); Gerald A. Higgins, Ann Arbor, MI (US); Alex Ade, Ann Arbor, MI (US); Alexandr Kalinin, Ann Arbor, MI (US); Narathip Reamaroon, Ann Arbor, MI (US); James S. Burns, Ann Arbor, MI (US)

(73) Assignee: REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 354 days.

This patent is subject to a terminal disclaimer.

(21) Appl. No.: 18/601,517

(22) Filed: Mar. 11, 2024

(65) Prior Publication Data

US 2024/0266018 A1 Aug. 8, 2024

Related U.S. Application Data

(63) Continuation of application No. 16/749,694, filed on Jan. 22, 2020, now Pat. No. 11,984,208.

(Continued)

(51) Int. Cl.

*G16H 20/10* (2018.01)
*G16B 5/00* (2019.01)

(Continued)

(52) U.S. Cl.

CPC .............. *G16H 20/10* (2018.01); *G16B 5/00* (2019.02); *G16B 5/10* (2019.02); *G16B 30/00* (2019.02);

(Continued)

(58) Field of Classification Search

None

See application file for complete search history.

(56) References Cited

U.S. PATENT DOCUMENTS 10,098,854 B2 10/2018 Drevets et al.
10,249,389 B2 4/2019 Athey et al.

(Continued)

FOREIGN PATENT DOCUMENTS

CN 109196590 A 1/2019
JP 2012524124 A 10/2012

(Continued)

OTHER PUBLICATIONS

Higgins et al., Network reconstruction reveals that valproic acid activates neurogenic transcriptional programs in adult brain following traumatic injury, Pharm. Res., 34:1658-72 (2017).

(Continued)

*Primary Examiner* — Karlheinz R. Skowronek
*Assistant Examiner* — Mary C Leverett
(74) *Attorney, Agent, or Firm* — MARSHALL, GERSTEIN & BORUN LLP

(57) ABSTRACT

Methods comprising an integrated, multiscale artificial intelligence-based system that reconstructs drug-specific pharmacogenomic networks and their constituent functional subnetworks are described. The system uses features of the functional topology of the three-dimensional architecture of drug-modulated spatial contacts in chromatin space. Discovery of a drug pharmacogenomic network is made through the selection of candidate SNPs by imputation, (Continued)

determination of the predicted causality of the SNPs using machine learning and deep learning, use of the causal SNPs to probe the spatial genome as determined by chromosome conformation capture analysis, combining targeted genes controlled by the same cell and tissue-specific enhancers, and reconstruction of the pharmacogenomic network using diverse data sources and metrics based on the results of genome-wide association studies. Knowledge-based segmentation methods are used to deconstruct the pharmacogenomic network into its constituent efficacy and adverse event sub-networks for applications in clinical decision support, drug re-purposing, and in silico drug discovery.

17 Claims, 81 Drawing Sheets

Related U.S. Application Data

(60) Provisional application No. 62/795,705, filed on Jan. 23, 2019, provisional application No. 62/795,710, filed on Jan. 23, 2019.

(51) Int. Cl.

| | |
|---|---|
| ***G16B 5/10*** | (2019.01) |
| ***G16B 30/00*** | (2019.01) |
| ***G16B 40/00*** | (2019.01) |
| ***G16B 45/00*** | (2019.01) |
| ***G16B 50/10*** | (2019.01) |
| ***G16H 50/20*** | (2018.01) |
| ***G16H 50/50*** | (2018.01) |

(52) U.S. Cl.

CPC ............. *G16B 40/00* (2019.02); *G16B 45/00* (2019.02); *G16B 50/10* (2019.02); *G16H 50/20* (2018.01); *G16H 50/50* (2018.01)

(56) References Cited

U.S. PATENT DOCUMENTS

| | | | |
|---|---|---|---|
| 2005/0048666 | A1 | 3/2005 | Larson et al. |
| 2005/0060305 | A1 | 3/2005 | Hopkins et al. |
| 2012/0041778 | A1 | 2/2012 | Kraft |
| 2014/0046696 | A1 | 2/2014 | Higgins et al. |
| 2014/0274764 | A1 | 9/2014 | Zhu et al. |
| 2015/0265628 | A1 | 9/2015 | Rosenblatt et al. |
| 2016/0045455 | A1 | 2/2016 | Drevets et al. |
| 2018/0330824 | A1 | 11/2018 | Athey et al. |

FOREIGN PATENT DOCUMENTS

| | | | |
|---|---|---|---|
| JP | 2014522530 | A | 9/2014 |
| JP | 2015520375 | A | 7/2015 |
| JP | 2015522565 | A | 8/2015 |
| JP | 2016521987 | A | 7/2016 |
| JP | 2016529903 | A | 9/2016 |
| JP | 2017524143 | A | 8/2017 |
| WO | WO-02/055995 | A2 | 7/2002 |
| WO | WO-2010/123898 | A1 | 10/2010 |
| WO | WO-2012/168481 | A1 | 12/2012 |
| WO | WO-2013/176694 | A1 | 11/2013 |
| WO | WO-2013186399 | A1 | 12/2013 |
| WO | WO-2014/202541 | A1 | 12/2014 |
| WO | WO-2015/031808 | A2 | 3/2015 |
| WO | WO-2015168346 | A1 | 11/2015 |
| WO | WO-2018075332 | A1 | 4/2018 |

OTHER PUBLICATIONS

Chiu et al., Application of the Cockcroft-Gault method to estimate lithium dosage requirement, Psychiatry and Clinical Neurosciences, 61.3:269-74 (2007).

Kantae et al., Integration of pharmacometabolomics with pharmacokinetics and pharmacodynamics: towards personalized drug therapy, Metabolomics, 13:1-11 (2017).

Lee et al., DeSigN: connecting gene expression with therapeutics for drug repurposing and development, BMC Genomics, 18.1:1-11 (2017).

Chinese Patent Application 202080015844.7, Office Action, dated Aug. 13, 2024.

Cirillo et al., A review of pathway-based analysis tools that visualize genetic variants, Frontiers in Genetics, 8:174 (2017).

Duman et al., Signaling pathways underlying the rapid antidepressant actions of ketamine. *Neuropharmacology* 62, 35-41 (2012).

Glusman et al., Mapping genetic variations to three-dimensional protein structures to enhance variant interpretation: a proposed framework, Genome Med., 9(1):113 (2017).

Guo et al., Exploratory genome-wide association analysis of response to ketamine and a polygenic analysis of response to scopolamine in depression. *Translational psychiatry* 8, 280 (2018).

Hansen et al., Generating genome-scale candidate gene lists for pharmacogenomics, Clin. Pharm. & Ther., 86(2):183-9 (2009).

Higgins et al., A glutamatergic network mediates lithium response in bipolar disorder as defined by epigenome pathway analysis. *Pharmacogenomics* 16, 1547-1563 (2015).

Higgins et al., Epigenomic mapping and effect sizes of noncoding variants associated with psychotropic drug response. *Pharmacogenomics* 16, 1565-1583 (2015).

Higgins et al., The epigenome, 4D nucleome and next-generation neuropsychiatric pharmacogenomics, Pharmacogenomics, 16(14):1649-69 (2015).

International Application No. PCT/US2020/014536, International Preliminary Report on Patentability (Chapter II), mailed Apr. 26, 2021.

International Application No. PCT/US2020/014536, International Search Report and Written Opinion, mailed May 12, 2020.

International Application No. PCT/US2020/014549, International Search Report and Written Opinion, mailed May 11, 2020.

Jayavelu et al., Iterative sub-network component analysis enables reconstruction of large scale genetic networks, BMC Bioinformatics, 16:366 (2015).

Kalinin et al., Deep learning in pharmacogenomics: from gene regulation to patient stratification. *Pharmacogenomics* 19, 629-650 (2018).

Licinio et al., Pharmacogenomics of antidepressent treatment effects, Dialogues Clin. Neurosci., 13(1):63-71 (2011).

Lu et al., 3DSNP: a database for linking human noncoding SNPs to their three-dimensional interacting genes, Nucleic Acids Res., 45(d1):D643-D649 (2017).

Niciu et al., Glutamate receptor antagonists as fast-acting therapeutic alternatives for the treatment of depression: ketamine and other compounds. *Annual review of pharmacology and toxicology* 54, 119-139 (2014).

Reiling et al., New Pharmacogenomics Research Network: An Open Community Catalyzing Research and Translation in Precision Medicine, Clin. Pharmacol. Ther., 102(6):897-902 (2017).

Tanaka et al., Pharmacogenomics of cardiovascular pharmacology: Pharmacogenomic network of cardiovascular disease models, J. Pharm. Sci., 107:8-14 (2008).

Tang et al., CTCF-Mediated Human 3D Genome Architecture Reveals Chromatin Topology for Transcription, Cell, 163(7):1611-27 (2015).

Turner et al., Parsing interindividual drug variability: an emerging role for systems pharmacology, Wiley Interdiscip. Rev. Syst. Biol. Med., 7(4):221-41 (2015).

U.S. Appl. No. 16/749,737, filed Jan. 22, 2020.

Vialou et al., Epigenetic mechanisms of depression and antidepressant action. Ann. Rev. Pharmacol. Toxicol., 53:59-87 (2013).

(56) References Cited

OTHER PUBLICATIONS

Way et al., Implicating candidate genes at GWAS signals by leveraging topologically associating domains, Eur. J. Hum. Genet., 25(11):1286-9 (Nov. 2017).
Zanos et al., Ketamine and Ketamine Metabolite Pharmacology: Insights into Therapeutic Mechanisms. *Pharmacological reviews* 70, 621-660 (2018).
U.S. Appl. No. 16/749,694, filed Jan. 22, 2020.
Griebel et al., Neuropeptide receptor ligands as drugs for psychiatric diseases: the end of the beginning?, Nat. Rev. Drug Discov., 11(6):462-78 (2012).
Sulman et al., Molecular predictors of outcome and response to bevacizumab (BEV) based on analysis of RTOG 0825, a phase III trial comparing chemoradiation (CRT) with and without BEV in patients with newly diagnosed gliobastoma (GBM), J. Clin. Oncol., 31(18 Suppl) (Jun. 2013). [abstract].
Higgins et al., Mining the topography and dynamics of the 4D nucleome to identify novel CNS drug pathways, Methods, 123:102-18 (2017).
European Patent Application No. 20708286.8, Communication Pursuant to Article 94(3) EPC, dated Jul. 4, 2024.

Chromatin is organized with the three-dimensional (3D) architecture of the human genome in a manner that resembles a "ball-of-yarn", including pre-existing and drug-induced changes in spatial contacts.

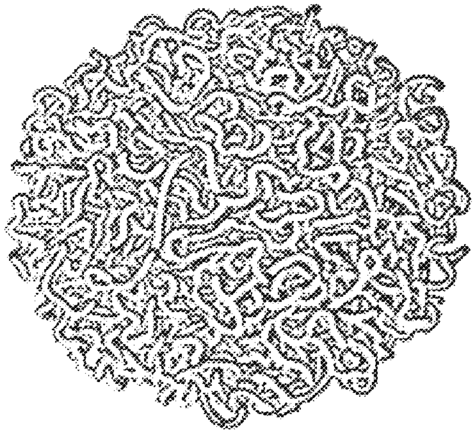

FIG. 5A

Drug pharmacogenomic networks consist of specific chromatin contacts that are comprised of local (cis) enhancer-promoter and promoter-promoter interactions within TADs that are activated (expanded) or repressed (contracted) by the drug. Adjacent TADs may have their genes controlled by superenhancers in cis-interactions. Distant (trans) interactions are based on spatial promixity in the 3D genome.

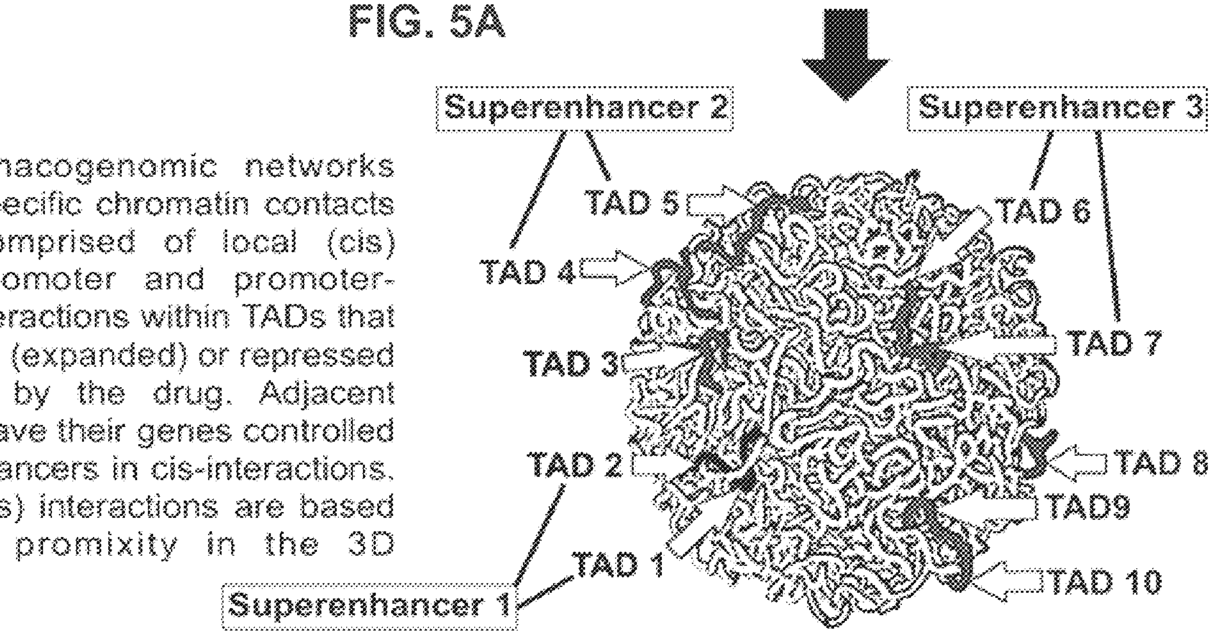

FIG. 5B

MEASURES

1. Three-dimensional (3D) nuclear arhitecture: Develop 3D model of cell type-specific nucleus, map drug-induced difference in chromatin contacts using Euclidian spatial coordinates (x, y, z). May be performed using FISH and high resolution microscopic analysis;
2. Matrix mapping of TADs activated / repressed by input drug using both chromosome conformation capture and gene expression methods. Convert for 2D for comparative analysis using deep learning;
3. Apply know chromosome conformation capture methods for inference of differential TAD activation / repression and chromatin loop contacts.

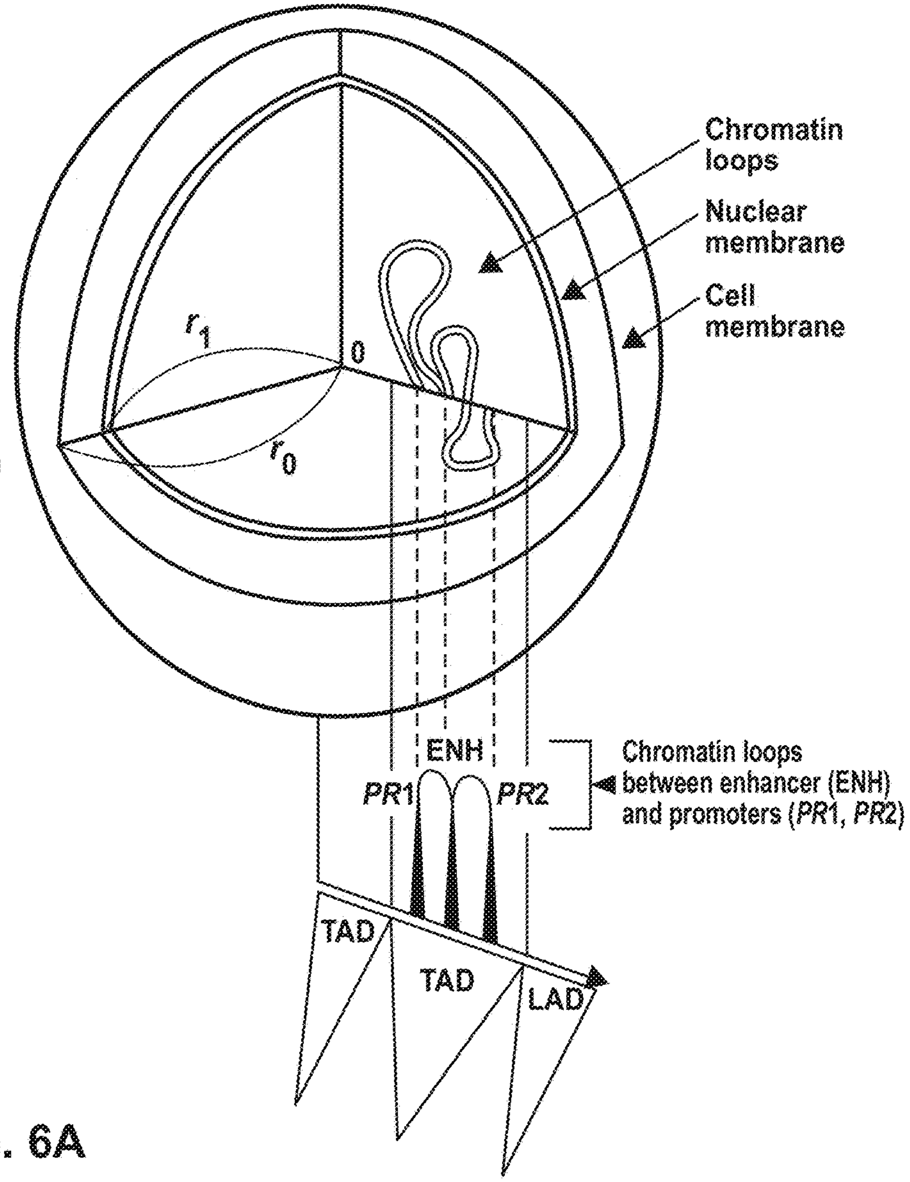

FIG. 6A

| GENES | TAD COORDINATES (Human GRch 37/hg19) | NUMBER OF GENES IN TAD | TAD SIZE | MOST SIGNIFICANT BIOLOGICAL PROCESS OF ENTIRE TAD | TAD BOUNDARY STRENGTH |
|---|---|---|---|---|---|
| **EXAMPLES OF PHARMACOKINETIC GENES** | | | | | |
| *CYP1A1, CYP1A2, CYP11A1* | 15:74652947-75252947 | 17 | 600 KB | Dibenzo-p-dioxin metabolic process, P=9.4E-04 | V |
| *CYP2A6, CYP2A7, CYP2B6, CYP2A13, CYPF1, CYP2S1* | 19:41348160-4248160 | 24 | 1.08 MB | Epoxygenase P450 pathway, P=8.39E-10 | V |
| *CCYP2C8, CYP2C9, CYP2C18, CYP2C19* | 10:96330010-98130010 | 18 | 1.8 MB | Omega-hydroxylase P450 pathway, P=6.55E-04 | V |
| *CYP2D6, CYP2D7* | 22:42030054-42950056 | 21 | 920 KB | Drug catabolic process, P=4.41E-03 | III |
| *CYP3A4, CYP3A5, CYP3A43, CYP3A7* | 7:99042064-100482064 | 51 | 1.44 MB | Lipid hydroxylation, P=3.24E-03 | V |
| *CYP4F2, CYP4F3, CYPF411, CYP4F12, CYP4F22* | 19:14619000-1633900 | 42 | 1.72 MB | Leukotriene metabolic process, P=1.56E-04 | V |
| *UGT1A1, UGT1A3, UGT1A4, UGT1A5, UGT1AG, UGT1A7* | 2:234375261-234735261 | 13 | 360 KB | Xenobiotic glucuronidation, P=3.0E-24 | V |
| *UGT2A3, UGT2B7, UGT2B10, UGT2B11* | 4:69590555-70085411 | 5 | 494 KB | Cellular glucuronidation, P=3.00E-05 | V |
| *UGT2A1, UGT2B4, UGT2B28, SULT1B1, SULT1E1* | 4:70085411-70841136 | 7 | 755 KB | Xenobiotic metabolic process, P=7.83E-09 | V |
| *SULT1A1, SULT1A2, SULT1A3, SULT1A4* | 16:27492499-28652499 | 24 | 2.4 MB | Xenobiotic metabolic process, P=5.63E-05 | V |
| *NAT1, NAT2* | 8:17795720-18675720 | 5 | 880 KB | Arylamine N-acetyltransferase activity P=1.35E-04 | V |
| **EXAMPLES OF ADVERSE DRUG EVENT GENES** | | | | | |
| *HLA-DRA, HLA-DRB1, HLA-DRB5, HLA-DQA1, HLA-DQA2, HLA-DQB1, HLA-DQB2, HLA-DMA, HLA-DMB, HLA-DOA, HLA-DOB, HLA-DP1, HLA-DPB1* | 6:32172022-33252022 | 31 | 1.08 MB | Antigen processing and presentation of exogenous peptide antigen, P=2.69E-20 | V |
| *HCP5, HLA-A, HLA-B, HLA-C, MICA, MICB* | 6:30972499-31532499 | 21 | 560 KB | Antigen processing and presentation of exogenous peptide antigen, P=4.01E-09 | V |

FIG. 10

| Medications, Topology 1 | Medications, Topology 2 | Medications, Topology 3 | Medications, Topology 4 |
|---|---|---|---|
| Valproic acid<br>Bexarotene<br>Trichostatin A | Ketamine<br>Esketamine<br>Lamotrigine | Clozapine<br>Chlorpromazine<br>Carbamazine | Lithium<br>Lithium carbonite<br>Fluoxetine |

| Diseases Annotation | p-value of overlap |
|---|---|
| Epilepsy or neurodevelopmental disorder | 2.19E-31 |
| Cognitive impairment | 5.29E-25 |
| Mood disorders | 1.35E-21 |
| Migraine | 1.78E-19 |
| Mania | 4.26E-19 |

| Upstream Regulator | p-value of overlap |
|---|---|
| valproic acid | 5.20E-114 |
| trichostatin A | 3.21E-35 |
| nicotine | 5.57E-21 |
| curcumin | 6.15E-20 |
| lithium chloride | 6.66E-15 |
| clozapine | 3.99E-11 |
| morphine | 5.32E-11 |
| resveratrol | 5.52E-11 |
| lithium | 1.02E-10 |
| carbamazepine | 5.93E-10 |

| The valproic acid adverse event sub-network | | | | | | | |
|---|---|---|---|---|---|---|---|
| GWAS SNP | Populations | Gene(s) | Reported trait | Reported P-value | Enhancer, cell type | Hi-C score: Human brain | PMID |
| rs71530654 | EUR | HDAC9 | Alopecia | 5E-70 | Neuron | 1E-10: Temporal cortex | 28196072 |
| rs13300218 | EUR | NOTCH1 | Inflammatory bowel disease | 5E-29 | Neuron | 1E-10: Dorsal root | 26192919 |
| rs13300218 | EUR | NOTCH1 | Crohn's disease | 7E-16 | Neuron | 1E-10: Dorsal root | 26192919 |
| rs13300218 | EUR | NOTCH1 | Ulcerative colitis | 2E-10 | Neuron | 1E-10: Dorsal root | 26192919 |
| rs77945277 | EUR | BAZ1A | Reduced efficacy, buproprion, bipolar depression | 3E-08 | Biopolar Neuron | 1E-10: Cingulate cortex | 27622933 |
| rs34102224 | EUR | CSMD1 | Reduced efficacy, buproprion, bipolar depression | 7E-06 | Biopolar Neuron | 1E-10: Frontal cortex | 27622933 |
| rs68088846 | EUR | RUNX1 | Alopecia | 3E-19 | Epithilial cell: Astrocyte | 1E-10: Cingulate cortex | 29146897 |

FIG. 22A

| The valproic acid neurogenesis sub-network | | | | | | | |
|---|---|---|---|---|---|---|---|
| GWAS SNP | Populations | Gene(s) | Reported trait | Reported P-value | Enhancer, cell type | Hi-C score: Human brain | PMID |
| rs1925950 | EUR | MEF2D | Chronic migraine | 9E-22 | Neuron | 1E-10: Cingulate cortex | 27182965 |
| rs1050316 | EUR | MEF2D | Headache | 2E-11 | Biopolar Neuron | 1.00E-15: Temporal cortex | 29397368 |
| rs6432877 | EUR | SCN1A | Epilepsy | 2E-13 | Neuron | 1E-05: Temporal cortex | 30531953 |
| rs6732655 | EUR | SCN1A | Epilepsy | 9E-10 | Biopolar Neuron | 1E-05: Temporal cortex | 30531953 |
| rs7587026 | EUR | SCN1A | Epilepsy | 3E-09 | Neuron | 1E-20: Temporal cortex | 24014518 |
| rs1006737 | EUR | CACNA1C | Bipolar I disorder (F31.0 - F31.64) | 6E-13 | Biopolar Neuron | 1E-10: Cingulate cortex | 24280982 |
| rs10744560 | EUR | CACNA1C | Bipolar I disorder (F31.0 - F31.64) | 4E-10 | Biopolar Neuron | 1E-10: Cingulate cortex | 31043756 |
| rs10998815 | EUR | ANK3 | Bipolar I disorder (F31.0 - F31.64) | 7E-11 | Biopolar Neuron | 1E-19: Frontal cortex | 31096178 |
| rs10994338 | EUR | ANK3 | Bipolar I disorder (F31.0 - F31.64) | 9E-09 | Biopolar Neuron | 1E-19: Frontal cortex | 31096178 |
| rs1051730 | ASN, EUR | XBP1 | Efficacy, valpropic acid in mania | 6E-27 | Neuron | 1E-23: Frontal cortex | 25910213 |

FIG. 22B

| Symbol | Entrez Gene Name |
|---|---|
| ACTL6A | actin like 6A |
| ACTL6B | actin like 6B |
| ARID1A | AT-rich interaction domain 1A |
| ARID1B | AT-rich interaction domain 1B |
| ARID2 | AT-rich interaction domain 2 |
| BCL11A | BAF chromatin remodeling complex subunit BCL11A |
| HDAC1 | histone deacetylase 1 |
| HDAC10 | histone deacetylase 10 |
| HDAC2 | histone deacetylase 2 |
| HDAC3 | histone deacetylase 3 |
| HDAC4 | histone deacetylase 4 |
| HDAC5 | histone deacetylase 5 |
| HDAC6 | histone deacetylase 6 |
| HDAC7 | histone deacetylase 7 |
| HDAC8 | histone deacetylase 8 |
| HDAC9 | histone deacetylase 9 |
| HST1H3G | histone cluster 1 H3 family member g |
| HST2H3C | histone cluster 2 H3 family member c |
| HST3H2A | histone cluster 3 H2A |
| HST3H2BB | histone cluster 3 H2B family member b |
| HST4H4 | histone cluster 4 H4 |
| INO80 | INO80 complex subunit |
| PBRM1 | polybromo 1 |
| SMARCA2 | SWI/SNF related, matrix associated, actin dependent regulator of chromatin, subfamily a, member 2 |
| SMARCA4 | SWI/SNF related, matrix associated, actin dependent regulator of chromatin, subfamily a, member 4 |
| SMARCB1 | SWI/SNF related, matrix associated, actin dependent regulator of chromatin, subfamily b, member 1 |
| SMARCC1 | SWI/SNF related, matrix associated, actin dependent regulator of chromatin, subfamily c, member 1 |
| SMARCD1 | SWI/SNF related, matrix associated, actin dependent regulator of chromatin, subfamily d, member 1 |
| SMARCD2 | SWI/SNF related, matrix associated, actin dependent regulator of chromatin, subfamily d, member 2 |
| SMARCE1 | SWI/SNF related, matrix associated, actin dependent regulator of chromatin, subfamily e, member 1 |
| SOX10 | SRY-box 10 |
| SS18L1 | SS18L1 subunit of BAF chromatin remodeling complex |
| ST18 | ST18, C2HC-type zinc finger |

FIG. 24

| Symbol | Entrez Gene Name |
|---|---|
| ACSL1 | acyl-CoA synthetase long chain family member 1 |
| AKT1 | AKT serine/threonine kinase 1 |
| ANK3 | ankyrin 3 |
| ATF3 | activating transcription factor 3 |
| ATF4 | activating transcription factor 4 |
| BDNF | brain derived neurotrophic factor |
| BDNF-AS | BDNF antisense RNA |
| BMP2 | bone morphogenetic protein 2 |
| CACNA1C | calcium voltage-gated channel subunit alpha 1 C |
| CAMK2A | calcium/calmodulin dependent protein kinase II alpha |
| CARM1 | coactivator associated arginine methyltransferase 1 |
| CASP3 | caspase 3 |
| CCL2 | C-C motif chemokine ligand 2 |
| CHGB | chromogranin B |
| CRHR1 | corticotropin releasing hormone receptor 1 |
| CXCR4 | C-X-C motif chemokine receptor 4 |
| DNAJC3 | DnaJ heat shock protein family Hsp40) member C3 |
| DRD1 | dopamine receptor D2 |
| EGR1 | early growth response 1 |
| EP300 | E1A binding protein p300 |
| FGF7 | fibroblast growth factor 7 |
| FGF9 | fibroblast growth factor 9 |
| FOXC1 | forkhead box C1 |
| FRS2 | fibroblast growth factor receptor substrate 2 |
| GABBR1 | gamma-aminobutyric acid type B receptor subunit 1 |
| GABRB2 | gamma-aminobutyric acid type A receptor beta2 subunit |
| GABRG2 | gamma-aminobutyric acid type A receptor gamma2 subunit |
| GAP43 | growth associated protein 43 |
| GDNF | glial cell derived neurotrophic factor |
| GFAP | glial fibrillary acidic protein |
| GRIA1 | glutamate ionotropic receptor AMPA type subunit 1 |
| GSK3B | glycogen synthase kinase 3 beta |
| HES1 | hes family bHLH transcription factor 1 |
| HIF1A | hypoxia inducible factor 1 subunit alpha |
| HOXA2 | homeobox A2 |
| HOXB1 | homeobox B1 |
| HOXB4 | homeobox B4 |
| ID2 | inhibitor of DNA biding 2 |
| INA | internexin neuronal intermediate filament protein alpha |
| KIT | KIT proto-oncogene, receptor tyrosine kinase |
| L1CAM | L1 cell adhesion molecule |
| MAPK10 | mitogen-activated protein kinase 10 |
| MECP2 | methyl-CpG binding protein 2 |
| MEF2C | myocyte enhancer factor 2C |
| MEF2D | myocyte enhancer factor 2D |
| MEIS1 | Meis homeobox 1 |
| MYT1L | myelin transcription factor 1 like |
| NCAM1 | neural cell adhesion molecule 1 |
| NEFH | neurofilament heavy |

FIG. 25A

| | |
|---|---|
| NEFL | neurofilament light |
| NEFM | neurofilament medium |
| NES | nestin |
| NEUROD1 | neuronal differentiation 1 |
| NEUROG3 | neurogenin 3 |
| NFE2L2 | nuclear factor, erythroid 2 like 2 |
| NOTCH1 | notch receptor 1 |
| NR0B2 | nuclear receptor subfamily 0 group B member 2 |
| NR1D1 | nuclear receptor subfamily 1 group D member 1 |
| NR6A1 | nuclear receptor subfamily 6 group A member 1 |
| NRN1 | neuritin 1 |
| NTF3 | neurotrophin 3 |
| OLIG2 | oligodendrocyte transcription factor 2 |
| PAX6 | paired box 6 |
| PLXNA4 | plexin A4 |
| POMC | proopiomelanocortin |
| POU5F1 | POU class 5 homeobox1 |
| PPARD | Peroxisome proliferator activated receptor delta |
| PROX1 | prospero homeobox 1 |
| PRRX1 | paired related homeobox 1 |
| RBFOX1 | RNA binding fox-1 homolog 1 |
| RUNX1 | runt related transcription factor 1 |
| SCN1A | sodium voltage-gated channel alpha subunit 1 |
| SERPINE1 | serpin family E member 1 |
| SIRT1 | sirtuin 1 |
| SMAD4 | SMAD family member 4 |
| SNCA | synuclein alpha |
| SNCB | synuclein beta |
| SOX11 | SRY-box 11 |
| SOX2 | SRY-box 2 |
| SP2 | Sp2 transcription factor |
| SP3 | Sp3 transcription factor |
| SPI1 | Spi-1 proto-oncogene |
| STAT1 | signal transducer and activator of transcription 1 |
| STAT3 | signal transducer and activator of transcription 3 |
| SV2A | synaptic vesicle glycoprotein 2A |
| SV2B | synaptic vesicle glycoprotein 2B |
| SYN1 | synapsin I |
| SYNGAP1 | synaptic Ras GTPase activating protein 1 |
| SYT1 | synaptotagmin 1 |
| TBR1 | T-box, brain 1 |
| TH | tyrosine hydroxylase |
| THRB | thyroid hormone receptor beta |
| TOP2A | DNA topoisomerase II alpha |
| TUBB2B | tubulin beta 2B class IIb |
| TUBB3 | tubulin beta 3 class III |
| VIP | vasoactive intestinal peptide |
| WNT1 | Wnt family member 1 |
| WNT5A | Wnt family member 5A |
| XIAP | X-linked inhibitor of apoptosis |
| XBP1 | X-box binding protein 1 |
| YWHAH | tyrosine 3-monooxygenase/tryptophan 5-monooxygenase activation protein eta |
| ZEB1 | zinc finger E-box binding homeobox 1 |

FIG. 25B

| Symbol | Entrez Gene Name |
|---|---|
| *ABCD2* | ATP binding cassette subfamily D member 2 |
| *ACTC1* | actin alpha cardiac muscle 1 |
| *ALR1B1* | aldo-keto reductase family 1 member B |
| *AKR1C3* | aldo-keto reductase family 1 member C3 |
| *AKR1C4* | aldo-keto reductase family 1 member C4 |
| *ANXA2* | annexin A2 |
| *ATAD2* | ATPase family AAA domain containing 2 |
| *ATF3* | activating transcription factor 3 |
| *ATF4* | activating transcription factor 4 |
| *ATF6* | activating transcription factor 6 |
| *ATM* | ATM serine/threonine kinase |
| *ATP1A3* | ATPase Na+/K+ transporting subunit alpha 3 |
| *BAZ1A* | bromodomain adjacent to zinc finger domain 1A |
| *BAZ2B* | bromodomain adjacent to zinc finger domain 2B |
| *BCL2A1* | BCL2 related protein A1 |
| *BCL2L11* | BCL2 like 11 |
| *BRDT* | bromodomain testis associated |
| *CA4* | carbonic anhydrase 4 |
| *CADM3* | cell adhesion molecule 3 |
| *CARM1* | coactivator associated arginine methyltransferase |
| *CCR1* | C-C motif chemokine receptor 1 |
| *CDK5R1* | cyclin dependent kinase 5 regulatory subunit 1 |
| *CEBPA* | CCAAT enhancer binding protein alpha |
| *CHAF1B* | chromatin assembly factor 1 subunit B |
| *CHGA* | chromogranin A |
| *CLMN* | calmin |
| *DCT* | dopachrome tautomerase |
| *DLG3* | discs large MAGUK scaffold protein 3 |
| *DOCK10* | dedicator of cytokinesis 10 |
| *EDNRB* | endothelin receptor type B |
| *ELK1* | ETS transcription factor ELK1 |
| *ENPP5* | econucleotide pyrophosphatase/phosphodiesterase 5 (putative) |
| *EP300* | E1A binding protein p300 |
| *ETV6* | ETS variant 6 |
| *FLT3* | fms related tyrosine kinase 3 |
| *FSCN1* | fascin actin-bundling protein 1 |
| *GAD2* | glutamate decarboxylase 2 |
| *GALC* | galactosylceramidase |
| *GLUL* | glutamate-ammonia ligase |
| *GRIN2B* | glutamate ionotropic receptor NMDA type subunit 2B |
| *GRM1* | glutamate metabotropic receptor 1 |
| *GRM7* | glutamate metabotropic receptor 7 |
| *GSK3A* | glycogen synthase kinase 3 alpha |
| *HMOX1* | heme oxygenase 1 |
| *HNRNPA1* | heterogeneous nuclear ribonucleoprotein A1 |
| *HOMER1* | homer scaffold protein 1 |
| *HS6ST1* | heparan sulfate 6-O-sulfotransferase 1 |
| *IAPP* | islet amyloid polypeptide precursor |

FIG. 26-1

| | |
|---|---|
| ICAM1 | intercellular adhesion molecule 1 |
| ITPKA | inositol-trisphosphate 3-kinase A |
| KAT2A | lysine acetyltransferase 2A |
| KCNJ11 | potassium voltage-gated channel subfamily J member 11 |
| KCNJ3 | potassium voltage-gated channel subfamily J member 3 |
| KCNQ5 | potassium voltage-gated channel subfamily Q member 5 |
| KIT | KIT proto-oncogene, receptor tyrosine kinase |
| KMT2A | lysine methyltransferase 2A |
| LIN7B | lin-7 homolog B, crumbs cell polarity complex component |
| LMO1 | LIM domain only 1 |
| MAPK8 | mitogen-ectivated protein kinase 8 |
| MAST1 | microtubule associated serine/threonine kinase 1 |
| MBOAT1 | membrane bound O-acyltransferase domain containing 1 |
| MICA | MHC class I polypeptide sequence A |
| MTA1 | metastasis associated 1 |
| MTHFR | methylenetetrahydrofolate reductase |
| MYCN | MYCN proto-oncogene, bHLH transcription factor |
| NFYA | nuclear transcription factor Y subunit alpha |
| NGEF | neuronal guanine nucleotide exchange factor |
| NME1 | NME/NM23 nucleoside diphosphate kinase 1 |
| NOS3 | nitric oxide synthase 3 |
| NR3C1 | nuclear receptor subfamily 3 group C member 1 |
| OPRK1 | opioid receptor kappa 1 |
| OPRM1 | opioid receptor mu 1 |
| PPRC1 | peroxisome proliferator-activated receptor gamma, coactivator-related 1 |
| PREG1 | PEAK1 related, kinase-activating pseudokinase 1 |
| PRKCD | protein kinase C delta |
| PRKCZ | protein kinase C zete |
| PRKD1 | protein kinase D1 |
| PRMT8 | protein arginine methyltransferase 8 |
| PSMD1 | proteasome26S subunit, non-ATPase 1 |
| PSMD14 | proteasome26S subunit, non-ATPase 14 |
| RAB3A | RAB3A, member RAS oncogene family |
| RARA | retinoic acid receptor alpha |
| RUNX1 | runt related transcription factor 1 |
| ROR1 | receptor tyrosine kinase like orphan receptor 1 |
| RXRA | retinoid X receptor alpha |
| SERPINH1 | serpin family H member 1 |
| SIRT4 | sirtuin 4 |
| SIRT7 | sirtuin 7 |
| SLC12A5 | solute carrier family 12 member 5 |
| SLC7A8 | solute carrier family 7 member 8 |
| SYP | synaptophysin |
| TBL1X | transcription beta like 1 X-linked |
| TF | transferrin |
| TFEB | transcription factor EB |
| THBS1 | thrombospondin 1 |
| UBD | ubiquitin D |
| YY1 | YY1 transcription factor |
| ZNF296 | zinc finger protein 296 |
| ZNF585A | zinc finger protein 585A |
| ZNRF1 | zinc and ring finger 1 |

FIG. 26-2

| Symbol | Entrez Gene Name |
|---|---|
| *AR* | androgen receptor |
| *CYP2B6* | cytochrome P450 family 2subfamily B member 6 |
| *CYP2C8* | cytochrome P450 family 2subfamily C member 8 |
| *CYP2C9* | cytochrome P450 family 2subfamily C member 9 |
| *ESR1* | estrongen receptor 1 |
| *UGT1A1* | UDP glucuronosyltransferase family 1 member A1 |
| *UGT1A3* | UDP glucuronosyltransferase family 1 member A3 |
| *UGT1A4* | UDP glucuronosyltransferase family 1 member A4 |
| *UGT1A6* | UDP glucuronosyltransferase family 1 member A6 |
| *UGT2B17* | UDP glucuronosyltransferase family 2 member B17 |
| *UGT2B7* | UDP glucuronosyltransferase family 2 member B7 |

FIG. 27

| Diseases Annotation | p-value |
|---|---|
| Schizophrenia | 3.45E-41 |
| Refractory depression | 1.33E-40 |
| Bipolar disorder | 8.44E-40 |
| Postoperative delirium | 4.47E-39 |
| Postoperative pain | 3.20E-38 |

| Upstream Regulator | p-value |
|---|---|
| ketamine | 6.26E-33 |
| morphine | 1.97E-17 |
| nicotine | 6.62E-17 |
| cocaine | 6.92E-17 |
| haloperidol | 1.32E-14 |

The ketamine glutamate receptor sub-network

| GWAS SNP | Populations | Gene(s) | Reported trait | Reported P-value | Enhancer, cell type | Hi-C score: Human brain | PMID |
|---|---|---|---|---|---|---|---|
| rs1051730 | ASN, EUR | *CHRNA5, CHRNA3* | Smoking status | 6E-121 | Neuron | 1E-27: Nucleus accumbens | 30617275 |
| rs28681284 | ASN | *CHRNA5, CHRNA3* | Schizophrenia, chronic (F20) | 6E-13 | Neuron | 1E-27: Nucleus accumbens | 30285260 |
| rs2007044 | ASN | *CACNA1C* | Schizophrenia, chronic (F20) | 6E-20 | Bipolar neuron | 1E-10: Cingulate cortex | 29483656 |
| rs7192140 | EUR | *GRIN2A* | Smoking status | 2E-15 | Bipolar neuron | 1E-19: Frontal cortex | 30643251 |
| rs11647445 | EUR | *GRIN2A* | Bipolar 1 disorder (F31.0 - F31.64) | 1E-10 | Bipolar neuron | 1E-19: Frontal cortex | 31043756 |
| rs7893279 | ASN, EUR | *CACNB2* | Schizophrenia, chronic (F20) | 9E-14 | Neuron | 1E-10: Frontal cortex | 30285260 |
| rs111294930 | EUR | *LINCO1470, GRIA1* | Schizophrenia, chronic (F20) | 9E-12 | Bipolar neuron | 1E-12: Cingulate cortex | 29483656 |
| rs9292918 | ASN | *HCN1* | Schizophrenia, chronic (F20) | 4E-11 | Bipolar neuron | 1E-10: Frontal cortex | 28991256 |
| rs62367520 | EUR | *HCN1* | Smoking status | 1E-10 | Bipolar neuron | 1E-10: Frontal cortex | 29283656 |

FIG. 33A

The ketamine neuroplasticity sub-network

| GWAS SNP | Populations | Gene(s) | Reported trait | Reported P-value | Enhancer, cell type | Hi-C score: Human brain | PMID |
|---|---|---|---|---|---|---|---|
| rs61902811 | EUR | *TMPRSS5, DRD2* | Recurrent depression (F33) | 4E-39 | Neuron | 1E-04: Hippocampus | 30718901 |
| rs4936277 | EUR | *TMPRSS5, DRD2* | Alcohol use disorder, alcohol dependence | 1E-13 | Bipolar neuron | 1.00E-06: Nucleus Accumbens | 29942085 |
| rs7227069 | EUR | *DCC* | Recurrent depression (F33) | 2E-28 | Neuron | 1E-10: Cingulate cortex | 30718901 |
| rs12967143 | EUR | *TCF4* | Recurrent depression (F33) | 2E-27 | Neuron | 1E-10: Frontal cortex | 30718901 |
| rs7932640 | EUR | *GRM5* | Recurrent depression (F33) | 2E-25 | Neuron | 1E-04: Cingulate cortex | 30718901 |
| rs139438618 | AFR | *SEMA3A* | Major depression and alcoholism | 2E-11 | Bipolar neuron | 1E-10: Nucleus Accumbens | 29071344 |
| rs775766 | EUR | *ROBO2* | Recurrent depression (F33) | 2E-08 | Neuron | 1E-14: Cingulate cortex | 29942085 |
| rs1400237 | EUR | *ROBO2* | Response to ketamine in depression | 8E-06* | Neuron | 1E-14: Cingulate cortex | 30552316 |

FIG. 33B

| Symbol | Entrez Gene Name |
|---|---|
| *ARC* | activity regulated cytoskeleton associated protein |
| *ASCL1* | achaete-scute family bHLH transcription factor 1 |
| *BDNF* | brain derived neurotrophic factor |
| *BDNF-AS* | BDNF antisense RNA |
| *CAMK2A* | calcium/calmodulin dependent protein kinase II alpha |
| *CDKN1A* | cyclin dependent kinase inhibitor 1A |
| *CREM* | cAMP responsive element modulator |
| *CUX2* | cut like homeobox 2 |
| *DCC* | DCC netrin 1 receptor |
| *DRD2* | dopamine receptor D2 |
| *EEF2K* | eukaryotic elongation factor 2 kinase |
| *FMR1* | fragile X mental retardation 1 |
| *GDAP1L1* | ganglioside induced differentiation associated protein 1 like 1 |
| *GRM5* | glutamate metabotropic receptor 5 |
| *HOMER1* | homer scaffold protein 1 |
| *HTR1B* | 5-hydroxytryptamine receptor 1B |
| *HTR2A* | 5-hydroxytryptamine receptor 2A |
| *KLF6* | Kruppel like factor 6 |
| *LIN7C* | lin-7 homolog C, crumbs cell polarity complex component |
| *LOC105379109* | |
| *MEF2D* | myocyte enhancer factor 2D |
| *MYO6* | myosin VI |
| *MYT1L* | myelin transcription factor 1 like |
| *NEUROD1* | neuronal differentiation 1 |
| *NEUROD2* | neuronal differentiation 2 |
| *NHLH2* | nescient helix-loop-helix 2 |
| *NMB* | neuromedin B |
| *NSMF* | NMDA receptor synaptonuclear signaling and neuronal migration factor |
| *NTRK2* | neurotrophic receptor tyrosine kinase 2 |
| *PTEN* | phosphatase and tensin homolog |
| *PTGS2* | prostaglandin-endoperoxide synthase 2 |
| *RAC1* | Rac family small GTPase 1 |
| *RASGRF2* | Ras protein specific guanine nucleotide releasing factor 2 |
| *RHOA* | ras homolog family member A |
| *ROBO2* | roundabout guidance receptor 2 |
| *RP11_360A181* | |
| *SEMA3A* | semaphorin 3A |
| *SHANK1* | SH3 and multiple ankyrin repeat domains 1 |
| *SHANK2* | SH3 and multiple ankyrin repeat domains 2 |
| *SHANK3* | SH3 and multiple ankyrin repeat domains 3 |
| *SLC22A15* | solute carrier family 22 member 15 |
| *SLC6A2* | solute carrier family 6 member 2 |
| *SLIT1* | slit guidance ligand 1 |
| *SLIT2* | slit guidance ligand 2 |
| *SNAP25* | synaptosome associated protein 25 |
| *SYN1* | synapsin I |
| *SYN2* | synapsin II |
| *SYT3* | synaptotagmin 3 |
| *TBR1* | T-box, brain 1 |
| *TCF4* | transcription factor 4 |

FIG. 34

| Symbol | Entrez Gene Name |
|---|---|
| *ACHE* | acetylcholinesterase (Cartwright blood group) |
| *ATF7IP* | activating transcription factor 7 interacting protein |
| *ATF7IP2* | activating transcription factor 7 interacting protein 2 |
| *ATP1A1* | ATPase Na+/K+ transporting subunit alpha 1 |
| *BORCS7* | BLOC-1 related complex subunit 7 |
| *BRD4* | bromodomain containing 4 |
| *CACNA1C* | calcium voltage-gated channel subunit alpha1 C |
| *CACNB1* | calcium voltage-gated channel auxiliary subunit beta 1 |
| *CACNB2* | calcium voltage-gated channel auxiliary subunit beta 2 |
| *CACNG2* | calcium voltage-gated channel auxiliary subunit gamma 2 |
| *CHRM2* | cholinergic receptor muscarinic 2 |
| *CHRNA3* | cholinergic receptor nicotinic alpha 3 subunit |
| *CHRNA5* | cholinergic receptor nicotinic alpha 5 subunit |
| *CHRNA7* | cholinergic receptor nicotinic alpha 7 subunit |
| *CNR1* | cannabinoid receptor 1 |
| *DLG3* | discs large MAGUK scaffold protein 3 |
| *DLG4* | discs large MAGUK scaffold protein 4 |
| *DNMT1* | DNA methyltransferase 1 |
| *EHMT1* | euchromatic histone lysine methyltransferase 1 |
| *GABRA2* | gamma-aminobutyric acid type A receptor alpha2 subunit |
| *GABRA5* | gamma-aminobutyric acid type A receptor alpha5 subunit |
| *GAD1* | glutamate decarboxylase 1 |
| *GLRA1* | glycine receptor alpha 1 |
| *GLRA2* | glycine receptor alpha 2 |
| *GLRB* | glycine receptor beta |
| *GRIA1* | glutamate ionotropic receptor AMPA type subunit 1 |
| *GRIA2* | glutamate ionotropic receptor AMPA type subunit 2 |
| *GRIA4* | glutamate ionotropic receptor AMPA type subunit 4 |
| *GRIN1* | glutamate ionotropic receptor NMDA type subunit 1 |
| *GRIN2A* | glutamate ionotropic receptor NMDA type subunit 2A |
| *GRIN2B* | glutamate ionotropic receptor NMDA type subunit 2B |
| *GRIN2C* | glutamate ionotropic receptor NMDA type subunit 2C |
| *GRIN2D* | glutamate ionotropic receptor NMDA type subunit 2D |
| *GRIN3A* | glutamate ionotropic receptor NMDA type subunit 3A |
| *GRIN3B* | glutamate ionotropic receptor NMDA type subunit 3B |
| *HCN1* | hyperpolarization activated cyclic nucleotide gated potassium channel 1 |
| *HDAC5* | histone deacetylase 5 |
| *MBD1* | methyl-CpG binding domain protein 1 |
| *MPHOSPH8* | M-phase phosphoprotein 8 |
| *NCAM1* | neural cell adhesion molecule 1 |
| *NOS1* | nitric oxide synthase 1 |
| *NOS2* | nitric oxide synthase 2 |
| *NOS3* | nitric oxide synthase 3 |
| *NQO1* | NAD(P)H quinone dehydrogenase 1 |
| *OPRK1* | opioid receptor kappa 1 |
| *OPRM1* | opioid receptor mu 1 |
| *ROBO2* | roundabout guidance receptor 2 |
| *SETDB1* | SET domain bifurcated histone lysine methyltransferase 1 |
| *SHANK2* | SH3 and multiple ankyrin repeat domains 2 |
| *SIGMAR1* | sigma non-opioid intracellular receptor 1 |
| *SLC6A9* | solute carrier family 6 member 9 |
| *TASOR* | transcription activation suppressor |
| *TOGARAM2* | TOG array regulator of axonemal microtubules 2 |
| *TRIM28* | tripartite motif containing 28 |
| *ZNF274* | zinc finger protein 274 |

FIG. 35

| **Symbol** | **Entrez Gene Name** |
|---|---|
| *ANAPC2* | anaphase promoting complex subunit 2 |
| *CYP2A6 (includes others)* | cytochrome P450 family 2 subfamily A member 6 |
| *CYP2B6* | cytochrome P450 family 2 subfamily B member 6 |
| *CYP3A4* | cytochrome P450 family 3 subfamily A member 4 |
| *DLG4* | discs large MAGUK scaffold protein 4 |
| *EEF2K* | eukaryotic elongation factor 2 kinase |
| *ESR1* | estrogen receptor 1 |
| *GRIA1* | glutamate ionotropic receptor AMPA type subunit 1 |
| *GRIA4* | glutamate ionotropic receptor AMPA type subunit 4 |
| *GRIN1* | glutamate ionotropic receptor NMDA type subunit 1 |
| *GRIN2B* | glutamate ionotropic receptor NMDA type subunit 2B |
| *MYO6* | myosin VI |
| *ROBO2* | roundabout guidance receptor 2 |
| *SHANK2* | SH3 and multiple ankyrin repeat domains 2 |
| *TCERG1* | transcription elongation regulator 1 |

FIG. 36

| Diseases Annotation | p-value |
|---|---|
| Cognitive impairment | 9.45E-20 |
| Mood disorders | 7.93E-18 |
| Drug-induced tremor | 2.46E-16 |
| Drug-induced weight gain | 1.08E-15 |
| Schizophrenia | 1.00E-12 |

| Upstream Regulator | p-value |
|---|---|
| Lithium chloride | 2.04E-23 |
| Lithium | 4.20E-19 |
| Fluoxetine | 2.94E-14 |
| Haloperidol | 2.59E-12 |
| Valproic acid | 1.04E-11 |

| Symbol | Entrez Gene Name |
|---|---|
| *BCL2* | BCL2 apoptosis regulator |
| *BRD2* | bromodomain containing 2 |
| *HDAC3* | histone deacetylase 3 |
| *KMT2A* | lysine methyltransferase 2A |
| *KMT2D* | lysine methyltransferase 2D |
| *SBSN* | suprabasin |
| *TRIM26* | tripartite motif containing 26 |

FIG. 44

| Symbol | Entrez Gene Name |
|---|---|
| AKR1C3 | aldo-keto reductase family 1 member C3 |
| *ANK3* | ankyrin 3 |
| *AP3B2* | adaptor related protein complex 3 subunit beta 2 |
| *BAX* | BCL2 associated X, apoptosis regulator |
| *CAPRIN2* | caprin family member 2 |
| *CASP3* | caspase 3 |
| *CASP8* | caspase 8 |
| *CCNH* | cyclin H |
| *CDKN1A* | cyclin dependent kinase inhibitor 1A |
| *CEBPA* | CCAAT renhancer binding protein alpha |
| *CPEB1* | cytoplasmic polyadenylation element binding protein 1 |
| *CTNNB1* | catenin beta 1 |
| *CYCS* | cytochrome c, somatic |
| *DDX11* | DEADIH-box helicase 11 |
| *DKK1* | diokkopf WNT signaling pathway inhibitor 1 |
| *DLG4* | discs large MAGUK scaffold protein 4 |
| *DLL4* | delta like caronical Notch ligand 4 |
| *EMCN* | endomucin |
| *FOS* | FOS proto-oncogene, AP-1 transcription factor subunit |
| *FSCN1* | fascin actin-bundling protein 1 |
| *GRIA2* | glutamate ionotropic receptor AMPA type subunit 1 |
| *HDGFL3* | HDGF like 3 |
| *IPO8* | importin 8 |
| *ITIH3* | inter-alpha-trypsin inhibitor heavy chain 3 |
| *L1CAM* | L1 cell adhesion molecule |
| *MAD1L1* | mitotic arrest deficient 1 like 1 |
| *MAPK1* | mitogen- activated protein kinase 1 |
| *MAPT* | microtubule associated protein tau |
| *MEF2C* | myocyte enhancer factor 2C |
| *NKX2-1* | NK2 homeobox 1 |
| *NOTCH1* | notch receptor 1 |
| *NR1D1* | nuclear receptor subfamily 1 group D member 1 |
| *NTN1* | netrin 1 |
| *NTRK2* | neurotrophic receptor tryosine kinase 2 |
| *PARP1* | poly (ADP-ribose) polymerase 1 |
| *POU5F1* | POU class 5 homeobox 1 |
| *PPARGC1A* | PPARO coactivator 1 alpha |
| *PPP1R11* | protein phosphatase 1 regulatory inhibitor subunit 1 |
| *RASGRFF2* | Ras protein specific guanine nucleotide releasing factor 2 |
| *RGS2* | regulator of G protein signaling 2 |
| *SESTD1* | SEC14 and spectrin domain containing 1 |
| *SHISA9* | shisa family member 9 |
| *SRR* | serine racemase |
| *TNIK* | TRAF2 and NCK interacting kinase |
| *UBD* | ubiquilin D |
| *VCAN* | versican |

FIG. 45

| Symbol | Entrez Gene Name |
|---|---|
| *ARNTL* | aryl hydrocarbon receptor nuclear translocator like |
| *CACNA1C* | calcium voltage-gated channel subunit alpha 1 C |
| *CACNG2* | calcium voltage-gated channel auxillary subunit gamma 2 |
| *CHRNA2* | cholinergic receptor nicotinic alpha 2 subunit |
| *CLOCK* | clock circadian regulator |
| *DLG3* | discs large MAGUK scaffold protein 3 |
| *EPHX2* | epoxide hydrolase 2 |
| *GABBR1* | gamma-aminobutyric acid type B receptor subunit 1 |
| *GRIA4* | glutamate ionotropic receptor AMPA type subunit 4 |
| *GRWD1* | glutamate rich WD repeat containing 1 |
| *GSK3A* | glycogen synthase kinase 3 alpha |
| *GSK3B* | glycogen synthase kinase 3 beta |
| *IMPA2* | inositol monophosphatase 2 |
| *LMAN2L* | lectin, mannose binding 2 like |
| *NCS1* | neuronal calcium sensor 1 |
| *NR3C1* | nuclear receptor subfamily 3 group C member 1 |
| *PER1* | period circadian regulator 1 |
| *PER2* | period circadian regulator 2 |
| *PCDH12* | protocadherin 12 |
| *RELL2* | RELT like 2 |
| *TSPAN3* | tetraspanin 3 |

FIG. 46

| Symbol | Entrez Gene Name |
|---|---|
| *CHAC1* | ChaC glutathione specific gamma-glutamylcyclotransferase 1 |
| *CREB1* | cAMP responsice element binding protein 1 |
| *EIF4EBP2* | eukaryotic translation initiation factor 4E binding protein 2 |
| *HTR1A* | 5-hydroxytryptamine receptor 1A |
| *MC4R* | melanocortin 4 receptor |
| *OXT* | oxytocin/neurophsin I prepropeptide |
| *PDE3A* | phosphodiesterase 3A |
| *PVT1* | Pvt1 oncogene |
| *STAT3* | signal transducer and activator of transcription 3 |

FIG. 47

| Symbol | Entrez Gene Name |
|---|---|
| *AXIN1* | axin 1 |
| *AXIN2* | axin 2 |
| *HMG20A* | high mobility group 20A |
| *LINGO1* | leucine rich repeat and Ig domain containing 1 |
| *MYC* | MYC proto-oncogene, bHLH transcription factor |
| *PTGS2* | prostaglandin-endoperoxide synthase 2 |
| *SLC1A2* | solute carrier family 1 member 2 |

FIG. 48

| Diseases Annotation | p-value |
|---|---|
| Epilepsy | 1.95E-21 |
| Fibromyalgia | 9.75E-21 |
| Bipolar 1 disorder | 2.62E-19 |
| Mania | 3.12E-19 |
| Treatment-resistant schizophrenia | 9.83E-46 |

| Upstream Regulator | p-value |
|---|---|
| Lamotrigine | 1.08E-10 |
| Carbamazepine | 3.51E-08 |
| Mirtazapine | 1.06E-07 |
| Fluoxetine | 7.11E-06 |
| Haloperidol | 1.01E-05 |

Network topology

| Symbol | Entrez Gene Name |
|---|---|
| *ACTL6B* | actin like 6B |
| *ANKRA2* | ankyrin repeat family A member 2 |
| *ARID2* | AT-rich interaction domain 2 |
| *ARID2* | AT-rich interaction domain 4A |
| *ARID4A* | AT-rich interaction domain 4B |
| *BRD1* | bromodomain containing 1 |
| *BRD7* | bromodomain containing 7 |
| *CHD2* | chromodomain helicase DNA binding protein 2 |
| *GATAD2A* | GATA zinc finger domain containing 2A |
| *GATAD2B* | GATA zinc finger domain containing 2B |
| *HDAC2* | histone deacetylase 2 |
| *HDAC3* | histone deacetylase 3 |
| *HDAC5* | histone deacetylase 5 |
| *KAT6A* | lysine acetyltransferase 6A |
| *KDM5C* | lysine demethylase 5C |
| *MBD3* | methyl-CpG binding domain protein 3 |
| *PBRM1* | polybromo 1 |
| *SMARCA2* | SWI/SNF related, matrix associated, actin dependent regulator of chromatin, subfamily a, member 2 |
| *SMARCA4* | SWI/SNF related, matrix associated, actin dependent regulator of chromatin, subfamily a, member 4 |
| *SMARCC2* | SWI/SNF related, matrix associated, actin dependent regulator of chromatin, subfamily c, member 2 |
| *SMARCD1* | SWI/SNF related, matrix associated, actin dependent regulator of chromatin, subfamily d, member 1 |
| *SMARCD3* | SWI/SNF related, matrix associated, actin dependent regulator of chromatin, subfamily d, member 3 |
| *SMARCE1* | SWI/SNF related, matrix associated, actin dependent regulator of chromatin, subfamily e, member 1 |

FIG. 52

| Symbol | Entrez Gene Name |
|---|---|
| *AEAT* | 4-aminobutyrate aminotransferase |
| *AR* | androgen receptor |
| *ARMC8* | armadillo repeat cotaining 8 |
| *ASTN2* | astrotactin 2 |
| *BDNF* | brain derived neurotrophic factor |
| *CACNA1E* | calcium voltage-gated channel subunit alpha 1 E |
| *CADM1* | cell adhesion molecule 1 |
| *CAMK2B* | calcium/calmodulin dependent protein kinase II beta |
| *CCND1* | cyclin D1 |
| *CDA* | cytidine deaminase |
| *CDC5L* | call division cycle 5 like |
| *CEBPA* | CCAAT enhancer binding protein alpha |
| *CSNK2B* | casein kinase 2 beta |
| *CUL1* | cullin 1 |
| *CUX2* | cut like homeobox 2 |
| *CYP2S1* | cytochrome P450 family 2 subfamily S member 1 |
| *DCX* | doublecortin |
| *DLG1* | discs large MAGUK scaffold protein 1 |
| *DLG4* | discs large MAGUK scaffold protein 4 |
| *DLG5* | discs large MAGUK scaffold protein 5 |
| *DRD2* | dopamine receptor D2 |
| *EFHC1* | EF-hand domain containing 1 |
| *EPB41L3* | erythrocyte membrane protein band 4.1 like 3 |
| *EPHB1* | EPH receptor B1 |
| *ERBIN* | erbb2 interacting protein |
| *GABRA1* | gamma-aminobutyric acid type A receptor alpha1 subunit |
| *GABRB2* | gamma-aminobutyric acid type A receptor beta2 subunit |
| *GABRB3* | gamma-aminobutyric acid type A receptor beta3 subunit |
| *GABRG2* | gamma-aminobutyric acid type A receptor gamma2 subunit |
| *GID4* | GID complex subunit 4 homolog |

FIG. 53-1

| | |
|---|---|
| *HACE1* | HECT domain and ankyrin repeat containing E3 ubiquitin protein ligase 1 |
| *HTR1A* | 5-hydroxytryptamine receptor 1A |
| *HTR2A* | 5-hydroxytryptamine receptor 2A |
| *ISOC2* | isochorismatase domain containing 2 |
| *KCNC2* | potassium voltage-gated channel subfamily C member 2 |
| *KCNJ2* | potassium inwardly rectifying channel subfamily C member 2 |
| *LIN7A* | lin-7 homolog A, crumbs cell polarity complex component |
| *LIN7B* | lin-7 homolog B, crumbs cell polarity complex component |
| *LIN7C* | lin-7 homolog C, crumbs cell polarity complex component |
| *MBP* | myelin basic protein |
| *MEIS1* | Mois homeobox 1 |
| *MPP2* | membrane palmitoylated protein 2 |
| *MPP6* | membrane palmitoylated protein 6 |
| *NET1* | neuroepithelial cell transforming 1 |
| *NF2* | neurofibromin 2 |
| *NGB* | neuroglobin |
| *OSM* | oncostatin M |
| *PAQR8* | progestin and adipoQ receptor family member B |
| *PAX8* | paired box 6 |
| *PLK1* | polo like kinase 1 |
| *PRL* | prolactin |
| *SCN1A* | sodium voltage-gated channel alpha subunit 1 |
| *SCN2A* | sodium voltage-gated channel alpha subunit 2 |
| *SCN2B* | sodium voltage-gated channel beta subunit 2 |
| *SHANK3* | SH3 and multiple ankyrin repeat domains 3 |
| *SLC20A1* | solute carrier family 20 member 1 |
| *SQSTM1* | sequestosome 1 |
| *SYT2* | synaptotagmin 2 |
| *TP53* | tumor protein p53 |
| *TPH2* | tryptophan hydroxylase 2 |
| *TPM3* | tropomyosin 3 |
| *XBP1* | X-box binding protein |
| *YWHAG* | tyrosine 3-monooxygenase/tryptopphan 5-monooxygenase activation protein gamma |

FIG. 53-2

| Symbol | Entrez Gene Name |
|---|---|
| *ABCB1* | ATP binding cassette subfamily B member 1 |
| *ABRA* | actin binding Rho activating protein |
| *ADAT2* | adenosine deaminase lRNA specific 2 |
| *APP* | amyloid beta precursor protein |
| *C11or154* | chromosome 11 open reading fame 54 |
| *CALML4* | calmodulin like 4 |
| *CFDP1* | oranicfacial development protein 1 |
| *CLTC* | clathnin heavy chain |
| *CRAMP1* | cramped chromatin regulator hornolog 1 |
| *DHRSX* | dehydrogenase/reductase X-linked |
| *DNAJB14* | DnaJ heat shock protein family (Hsp40) member B14 |
| *DNAJB7* | DnaJ heat shock protein family (Hsp40) member B7 |
| *DNAJC4* | DnaJ heat shock protein family (Hsp40) member C4 |
| *DNAJC5B* | DnaJ heat shock protein family (Hsp40) member C5 beta |
| *FAM53A* | family with sequence similarity 53 member A |
| *FHIT* | fragile histidine triad diadenosine triphosphatase |
| *GUSB* | glucuronidase beta |
| *HDAC9* | histone deacetylase 9 |
| *HIF1A* | hypoxia inducible factor 1 subunit alpha |
| *HLA-A* | major histocompatbility complex, class I, A |
| *HLA-B* | major histocompatbility complex, class I, B |
| *HNF4A* | hepatocyte nuclear factor 4 alpha |
| *HNRNPL* | heterogeneous nuclearrioonucleoproteinL |
| *HTT* | huntingtin |
| *IFNA1/IFNA13* | interferon alpha 1 |
| *IFVA6* | interferon alpha 6 |
| *IFO8* | importin 8 |
| *KCNJ2* | potassium inwardly rectifying channel subfamily J member 2 |
| *MAPK10* | mitogen-activated protein kinase 10 |
| *MCTP2* | multiple C2 and transmembrane domain containing 2 |
| *MEF2C* | myocyte enhancer factor 2C |
| *NDUFB2* | NADHcubiquinone oxidoreductase subunit B2 |
| *NDUFV2* | NADHcubiquinone oxidoreductase core subunit V2 |
| *PNPLA7* | patath like phospholipase domain cortaining 7 |
| *PTCHD3* | patched domain containing 3 |
| *RAB18* | RAB18, member RAS oncogene family |
| *RNF14* | ring finger protein 14 |
| *SYT2* | synaptotagmin 2 |
| *TMCC1* | transmembrane and coiled-coil domain family 1 |
| *ZDHHC14* | zinc finger DHHC-type containing 14 |
| *ZNF236* | zinc finger protein 236 |
| *ZNF385B* | zinc finger protein 385B |
| *ZNF449* | zinc finger protein 449 |
| *ZNF706* | zinc finger protein 706 |
| *ZNF839* | zinc finger protein 839 |

FIG. 54

| Symbol | Entrez Gene Name |
|---|---|
| *SLC22A1* | solute carrier family 22 member 1 |
| *UGT1A1* | UDP glucuroncsyltransferase family 1 member A1 |
| *UGT1A3* | UDP glucuroncsyltransferase family 1 member A3 |
| *UGT1A4* | UDP glucuroncsyltransferase family 1 member A4 |
| *UGT1A6* | UDP glucuroncsyltransferase family 1 member A6 |
| *UGT2B7* | UDP glucuroncsyltransferase family 2 member B7 |

FIG. 55

| Diseases Annotation | p-value |
|---|---|
| Psychosis | 2.66E-57 |
| Agitation | 1.01E-49 |
| Bipolar spectrum disorder | 5.99E-48 |
| Non-affective psychosis | 3.33E-47 |
| Treatment-resistant schizophrenia | 9.83E-46 |

| Upstream Regulator | p-value |
|---|---|
| Clozapine | 8.85E-110 |
| Haloperidol | 1.45E-42 |
| Chlorpromazine | 6.59E-20 |
| Ollanzapine | 2E-19 |
| Risperidone | 5.45E-13 |

| Symbol | Entrez Gene Name |
|---|---|
| *BRD2* | bromodomain containing 2 |
| *EHMT2* | euchromatic histone lysine methyltransferase 2 |
| *HDAC2* | histone deacetylase 2 |
| *HDAC3* | histone deacetylase 3 |
| *KDM1A* | lysine demethylase 1A |
| *KDM6A* | lysine demethylase 6A |
| *KMT2A* | lysine methyltransferase 2A |
| *KMT2D* | lysine methyltransferase 2D |
| *MYT1* | myelin transcription factor 1 |
| *SOX2* | SRY-box transcription factor 2 |
| *WDR5* | WD repeat domain 5 |

FIG. 59

| Symbol | Entrez Gene Name |
|---|---|
| *ADH7* | alcohol dehydrogenase 7 (class IV), mu or sigma polypeptide |
| *ADRA1A* | adrenoceptor alpha 1A |
| *ADRA1B* | adrenoceptor alpha 1B |
| *ADRA1D* | adrenoceptor alpha 1D |
| *ADRA2A* | adrenoceptor alpha 2A |
| *ADRA2B* | adrenoceptor alpha 2B |
| *ADRA2C* | adrenoceptor alpha 2C |
| *AGER* | advanced glycosylation end-product specific receptor |
| *BCAS1* | breast carcinoma amplified sequence 1 |
| *BCL9* | BCL9 transcription coactivator |
| *BCL9L* | BCL9 like |
| *BDNF* | brain derived neurotrophic factor |
| *C11orf98* | chromosome 11 open reading frame 98 |
| *CACNB2* | calcium voltage-gated channel auxillary subunit beta 2 |
| *CASKIN2* | CASK interacting protein 2 |
| *CASP3* | caspase 3 |
| *CERS4* | Ceramide synthase 4 |
| *CHRM1* | cholinergic receptor muscarinic 1 |
| *CHRM3* | cholinergic receptor muscarinic 3 |
| *CHRM4* | cholinergic receptor muscarinic 4 |
| *CHRM5* | cholinergic receptor muscarinic 5 |
| *COL16A1* | collagen type XVI alpha 1 chain |
| *COMT* | calechol-O-methiltransferase |
| *CYTH4* | cytohesin 4 |
| *DLGAP1* | DLG associated protein 1 |
| *DLGAP2* | DLG associated protein 2 |
| *DRD1* | dopamine receptor D1 |
| *DRD2* | dopamine receptor D2 |
| *DRD3* | dopamine receptor D3 |
| *DRD4* | dopamine receptor D4 |
| *DRD5* | dopamine receptor D5 |
| *DVL3* | dishevelled segment polarity protein 3 |
| *EFHD1* | EF-hand domain family member D1 |
| *EGR1* | early growth response 1 |
| *ESR2* | estrogen receptor 2 |
| *EVX1* | even-skipped homeobox 1 |
| *FAM50A* | family with sequence similarity 50 member A |
| *FARP1* | FERM, ARH/RhoGEF and pleckstrin domain protein 1 |
| *FOS* | Fos proto-oncogene, AP-1 transcription factor subunit |
| *FOXA1* | forkhead box A1 |
| *GATA3* | GATA binding protein 3 |
| *GRIA1* | glutamate ionotropic receptor AMPA type subunit 1 |
| *GRIA2* | glutamate ionotropic receptor AMPA type subunit 2 |
| *GRIN2B* | glutamate ionotropic receptor NMDA type subunit 2B |
| *HOMER1* | homer scaffold protein 1 |
| *HRH1* | histamine receptor H1 |
| *HTR1A* | 5-hydroxytryplamine receptor 1A |

FIG. 60-1

| | |
|---|---|
| *HRT1B* | 5-hydroxytryptamine receptor 1B |
| *HRT1D* | 5-hydroxytryptamine receptor 1D |
| *HRT2A* | 5-hydroxytryptamine receptor 2A |
| *HRT2B* | 5-hydroxytryptamine receptor 2B |
| *HRT3A* | 5-hydroxytryptamine receptor 3A |
| *HRT3B* | 5-hydroxytryptamine receptor 3B |
| *HRT5A* | 5-hydroxytryptamine receptor 5A |
| *HRT6* | 5-hydroxytryptamine receptor 6 |
| *KCNC2* | potassium voltage-gated channel subfamily C member 2 |
| *KCNH2* | potassium voltage-gated channel subfamily H member 2 |
| *KIRREL3* | kirre like nephrin family adhesion molecule 3 |
| *LEP* | leptin |
| *MEIS2* | Meis homeobox 2 |
| *MICA* | MHC class I polypeptide-related sequence A |
| *MISP3* | MISP family member 3 |
| *MTERF4* | mitochondrial transcription termination factor 4 |
| *MTNR1B* | melatonin receptor 1B |
| *NOTCH4* | notch receptor 4 |
| *NR4A1* | nuclear receptor subfamily 4 group A member 1 |
| *NR4A2* | nuclear receptor subfamily 4 group A member 2 |
| *NR4A3* | nuclear receptor subfamily 4 group A member 3 |
| *NRXN1* | neurexin 1 |
| *NSUN5* | NOP2/Sun RNA methyltransferase 5 |
| *NTRK2* | neurotrophic receptor tyrosine kinase 2 |
| *PCDH19* | protocadherin 19 |
| *PRDM15* | PR/SET domain 15 |
| *PRDM16* | PR/SET domain 16 |
| *PRKAA1* | Protein kinase AMP-activated catalytic subunit alpha 1 |
| *PRL* | prolactin |
| *PRR12* | proline rich 12 |
| *PVALB* | parvalbumin |
| *RGS14* | regulator of G protein signaling 14 |
| *RIC3* | RIC3 acetylcholine receptor chaperone |
| *SDK1* | sidekick cell adhesion molecule 1 |
| *SGK1* | serum/glucocorticoid regulated kinase 1 |
| *SHANK1* | SH3 and multiple ankyrin repeat domains 1 |
| *SLITRK1* | SLIT and NTRK like family member 1 |
| *SNN* | Stannin |
| *SOX2* | SRY-box transcription factor 2 |
| *SREBF1* | sterol regulatory element binding transcription factor 1 |
| *SREBF2* | sterol regulatory element binding transcription factor 2 |
| *SYP* | synaptophysin |
| *TAC1* | tachykinin precursor 1 |
| *UCP1* | uncoupling protein 1 |
| *WNT5A* | Wnt family member 5A |
| *ZNF618* | zinc finger protein 618 |
| *ZNF652* | zinc finger protein 652 |
| *ZNF787* | zinc finger protein 787 |

FIG. 60-2

| Symbol | Entrez Gene Name |
|---|---|
| *ACAC2* | acetyl-CoA carboxylase alpha |
| *ACAT2* | acetyl-CoA acetyltransferase 2 |
| *AGER* | advanced glycosylation end-product specific receptor |
| *AKT1* | AKT serine/threonine kinase 1 |
| *ARRB2* | arrestin beta 2 |
| *AXIN1* | axin 1 |
| *B4GALT4* | beta-1,4 galactosyltransferase 4 |
| *C14ORF93* | chromosome 14 open reading frame 93 |
| *C4A/C4B* | complement C4B (Chido blood group) |
| *CASP3* | caspase 3 |
| *CCND1* | cyclin D1 |
| *CDH13* | cadherin 13 |
| *CDH24* | cadherin 24 |
| *CIDEA* | cell death inducing DFFA like effector a |
| *CL/C1* | chloride intracellular channel 1 |
| *CPT1C* | carnitine palmitoyltransferase 1C |
| *CSNK1A1* | casein kinase 1 alpha 1 |
| *CSNK2B* | casein kinase 2 beta |
| *CTNNA2* | catenin alpha 2 |
| *CTNNB1* | catenin beta 1 |
| *DHCR7* | 7-dehydrocholesterol reductase |
| *DIO2* | iodothyronine deiodinase 2 |
| *DIO3* | iodothyronine deiodinase 3 |
| *EPHB2* | EPH receptor B2 |
| *ERMN* | ermin |
| *EZH2* | enhancer of zeste 2 polycomb repressive complex 2 subunit |
| *FASN* | fatty acid synthase |
| *FDPS* | farnesyl diphosphate synthase |
| *FOS* | Fos proto-oncogene, AP-1 transcription factor subunit |
| *GATA3* | GATA binding protein 3 |
| *GPANK1* | G-patch domain and ankyrin repeats 1 |
| *GPR1* | G protein-coupled receptor 1 |
| *GSK3A* | glycogan synthase kinase 3 alpha |
| *GSK3B* | glycogan synthase kinase 3 beta |
| *H2-M2* | histocompatibility 2, M region locus 2 |
| *HCP5* | HLA complex P5 |
| *HLA-B* | major histocompatibility complex, class I, B |
| *HLA-C* | major histocompatibility complex, class I, C |
| *HLA-DRBB1* | major histocompatibility complex, class II, DR beta 1 |
| *HMGCR* | 3-hydroxy-3-methylglutaryl-CoA reductase 1 |
| *HMGCS1* | 3-hydroxy-3-methylglutaryl-CoA synthase 1 |
| *HRH3* | histamine receptor H3 |

FIG. 61-1

| | |
|---|---|
| HRH4 | histamine receptor H4 |
| HTR1F | 5-hydroxytryptamine receptor 1F |
| HTR2C | 5-hydroxytryptamine receptor 2C |
| HTR3A | 5-hydroxytryptamine receptor 3A |
| HTR4 | 5-hydroxytryptamine receptor 4 |
| HTR7 | 5-hydroxytryptamine receptor 7 |
| IFNG | interferon gamma |
| INSR | insulin receptor |
| LDLR | low density lipoprotein receptor |
| LRRC42 | leucine rich repeat containing 42 |
| MC4R | melanocortin 4 receptor |
| MICA | MHC class I polypeptide-related sequence A |
| MOV10 | Mov10 RISC complex RNA helicase |
| NANOG | Nanog homeobox |
| NCF1 | neutrophil cytosolic factor 1 |
| NFKB1 | nuclear factor kappa B subunit 1 |
| NTS | neurotensin |
| PBX2 | PBX homeobox 2 |
| PCMTD2 | protein-L-isoaspartate (D-aspartate) O-methyltransferase domain containing 2 |
| PEA15 | proliferation and apoptosis adaptor protein 15 |
| PPARD | peroxisome proliferator activated receptor delta |
| PPARGC1A | PPARG coactivator 1 alpha |
| PPP1R9B | protein phosphatase 1 regulatory subunit 9B |
| PRDM16 | PR/SET domain 16 |
| PRKACB | protein kinase cAMP-activated catalytic subunit beta |
| PRKAR2A | protein kinase cAMP-dependent type II regulatory subunit alpha |
| PRKAR2B | protein kinase cAMP-dependent type II regulatory subunit beta |
| PRKCI | protein kinase C Iota |
| RAD23A | RAD23 homolog A, nucleotide excision repair protein |
| RNF5 | ring finger protein 5 |
| RPS6 | ribosomal protein S6 |
| SC5D | sterol-C5-desaturase |
| SCD | stearoyl-CoA desaturase |
| SELENOW | selenoprotein W |
| SFMBT2 | Scm like with four mbt domains 2 |
| SLC1A2 | solute carrier family 1 member 2 |
| SPATA46 | spermatogenesis associated 46 |
| TAL1 | TAL bHLH transcription factor 1, erythroid differentiation factor |
| TAP1 | transporter 1, ATP binding cassette subfamily B member |
| TAP2 | transporter 2, ATP binding cassetter subfamily B member |
| TBX21 | t-box transcription factor 21 |
| TEX9 | testis expressed 9 |
| VPS54 | VPS54 subunit of GARP complex |
| XRCC4 | X-ray repair cross complementing 4 |
| ZNF343 | zinc finger protein 343 |
| ZNF618 | zinc finger protein 618 |

FIG. 61-2

| Symbol | Entrez Gene Name |
|---|---|
| *CYP1A1* | cytochrome P450 family 1 subfamily A member 1 |
| *CYP1A2* | cytochrome P450 family 1 subfamily A member 2 |
| *CYP2C19* | cytochrome P450 family 2 subfamily C member 19 |
| *CYP2C8* | cytochrome P450 family 2 subfamily C member 8 |
| *CYP2C9* | cytochrome P450 family 2 subfamily C member 9 |
| *CYP2D6* | cytochrome P450 family 2 subfamily D member 6 |
| *CYP2E1* | cytochrome P450 family 2 subfamily E member 1 |
| *CYP3A4* | cytochrome P450 family 3 subfamily A member 4 |
| *UGT1A4* | UDP glucuronosyltransferase family 1 member A4 |
| *UGT1A7* | UDP glucuronosyltransferase family 1 member A9 |
| *UGT2B10* | UDP glucuronosyltransferase family 2 member B10 |

FIG. 62

METHODS AND SYSTEM FOR THE RECONSTRUCTION OF DRUG RESPONSE AND DISEASE NETWORKS AND USES THEREOF

CROSS-REFERENCE TO RELATED APPLICATIONS

This application is a continuation of and claims priority to U.S. application Ser. No. 16/749,694, filed on Jan. 22, 2020, entitled Methods and System for the Reconstruction of Drug Response and Disease Networks and Uses Thereof," which claims priority to and the benefit of the filing date of (1) provisional U.S. Application Ser. No. 62/795,705, filed on Jan. 23, 2019, entitled "Methods and Systems to Reconstruct Drug Pharmacogenomic Networks from Pharmacogenomic Regulatory Interactions and Uses Thereof," and (2) provisional U.S. Application Ser. No. 62/795,710, filed on Jan. 23, 2019, entitled "Companion Diagnostic Assays for N-methyl-D-Aspartate Receptor Modulators," the entire disclosures of each of which is hereby expressly incorporated by reference herein.

FIELD OF THE INVENTION

The techniques described herein pertain to the discovery of gene network contacts in chromatin space that define a specific drug's pharmacogenomic substrate, the identification of functionally distinct gene sets within this drug's pharmacogenomic network called sub-networks, and detection of regulatory genome variants within the drug's sub-network gene sets that impact therapeutic efficacy or adverse events. Methods are described for the application of these results to characterize drug response in humans for clinical decision support, drug re-purposing including the development of novel companion therapeutics, and for in silico drug target discovery.

BACKGROUND

The Spatial Pharmacoepigenome, Super Enhancersuper Enhancers, and Topologically Associating Domains New insights into the architecture and dynamics of the noncoding regulatory genome have transformed conventional views of pharmacodynamics and pharmacokinetics. The non-coding, regulatory genome whose variation impacts drug response in humans is hereafter referred to as the "pharmacoepigenome." The pharmacoepigenome can be defined as the active, noncoding domain of the human genome that consists of spatial, temporal and mechanical regulatory mechanisms of gene regulation that respond to xenobiotic stimuli. It contains regulators of gene expression, including enhancers, promoters and regulatory RNAs, and is characterized by a hierarchy of stereotypic transcriptional domains in which variation profoundly impacts drug response in humans. Transcriptional control consists of canonical 3D structures that include enhancer-promoter pairs, super enhancersuper enhancers, transcriptional hubs, mRNA splicing factors, topologically associating domains (TADs), and lamina-associating domains (LADs). Specific, circumscribed sets of canonical 3D structures are activated or suppressed in a cell-type specific manner. Drug-disease networks are tightly coupled so that gene variants significantly associated with a disease are identical to, or are found within, the same regulatory networks that determine medication-based therapeutic outcomes. Thus, mutations that disrupt the spatial hierarchy of transcription within euchromatin not only convey disease risk but also concomitant variability in drug response. Pathways containing disease risk, drug response and concomitant adverse event variants are fertile networks for the discovery of new drug targets using genotype/phenotype-guided computational strategies. These insights better inform therapeutic options for patients based on the emerging pharmacological basis of drug response and adverse drug events. Examples of future therapeutic strategies that will involve combinatorial drug design targeting a pharmacogenomic network or networks, integrative multi-scale analytic methods, which draw from a diverse set of data types to enhance drug discovery based on stratification by environmental-by-molecular modification of the pharmacoepigenome, synthetic editing that alters non-coding regulatory elements which convey drug treatment resistance, and the development of transcription factor-like molecules for cellular reprogramming of tissue damage and atrophy.

It is important to note that highly significant SNP-trait associations examining hundreds of thousands of humans from both genome-wide association studies (GWAS), phenome-wide association studies (PheWAS), and other biobanked patient data, including SNPs that convey disease risk as well as an individual's response to a particular drug, are found within regulatory elements of the noncoding genome called enhancers. In many cases, enhancers target gene promoters or regulatory RNAs within the same TAD and may be controlled by larger regulatory elements called super enhancers.

Human genes that play critical roles in health, disease states, and drug response, are often regulated by long DNA elements that span 2 or more TADs called "super-enhancers" or "stretch enhancers", herein known as super enhancersuper enhancers. Super enhancerSuper enhancers are clusters of enhancers that are occupied by an unusually high density of interacting factors and activate higher frequencies of differential transcription, also known as gene expression, than that exhibited by typical enhancers. Super enhancer-Super enhancers are multimolecular assemblies that represent macromolecular condensates, similar to the nucleolus, which concentrate and compartmentalize transcriptional regulation within the nucleus of cells. Super enhancerSuper enhancers occupy known genomic positions that straddle multiple TADs and LADs in a cell- and developmental-specific manner.

Mutations that alter super enhancersuper enhancers and disrupt their regulation of genes and RNAs, resulting in the abolition or alteration of chromatin loops between enhancer-promoters or promoter-promoter pairs, and/or break the boundaries of TADs, or disperse the repressive subset of TADs called LADs, have profound consequences for variation in drug response and the incidence of adverse drug events in human populations.

The largest pharmacogenomic effect sizes have been found in patients with SNPs that are single base changes that disrupt super enhancers, causing life-threatening, acute adverse drug events. Examples include clozapine-induced agranulocytosis/granulocytopenia and Stevens-Johnson syndrome or toxic epidermal necrolysis caused by carbamazepine, lamotrigine, phenobarbital, allopurinol, non-steroidal anti-inflammatories and certain other medications. These adverse drug reactions are severe enough that countries such as Singapore and Taiwan require patients be tested for the presence of these SNPs prior to the administration of these medications.

Super enhancers are responsible for specifying the identity of different cell types during development, and in tissues such as the brain, they serve as platforms for the binding of the neural-specific transcription factors and the Mediator complex. They represent a non-traditional pharmacodynamic target, and their involvement in differential neurogenesis in adult brain are also mechanisms by which inhibitors of histone deacetylases exert their action in the CNS. Similarly, unconventional interpretation of drug response and remission single nucleotide polymorphisms (SNPs) from GWAS and PheWAS have markedly improved our understanding of ways in how mutational perturbation of the molecular physiology of the cell leads to human pharmacogenomic variation.

The spatial hierarchy of transcriptional organization is first determined by chromatin conformation capture methods. Chromosomes fill in much of the available volume of the nucleoplasm as chromosome territories (CTs) and contain circumscribed A and B compartments that consist of euchromatin and heterochromatin, respectively. In general, compartment A contains euchromatin and more active gene transcription and compartment B corresponds to heterochromatin and is gene poor. Compartment B subsumes LADs located at the periphery of the nucleus. These are specific to chromosome territories and appear to be a largely invariant feature of chromatin organization, as they are not disrupted when the organization of TADs or LADs are destroyed using genome-editing methods. The A and B chromatin compartments of CTs contain approximately 2,450 TADs with an average length in linear sequence of 100 Kbp (Kilobase pairs) to 5 Mbp (Megabase pairs). TADs were first characterized using chromatin conformation capture methods such as Hi-C permitting high resolution study of enhancer-promoter loops within TADs and the organization of TAD boundary proteins.

Chromosomes are contained within the nucleoplasm of differentiated cells as large, rope-like coils of genomic DNA encapsulated in chromatin. CTs exist in 3D space where spatial proximity and chromatin state determine regulatory interactions, not distance as measured in linear DNA sequence. Although CTs do not overlap to any great degree, there are multiple spatial interactions between different CTs that are functional. These include complex transcriptional hubs that consist of multiple genes, regulatory elements including enhancers and promoters, and DNA-binding proteins such as transcription factors that are functionally related. Trans-interactions include inter-chromosomal spatial contacts that involve enhancer-promoter interactions, or in some cases, promoter-promoter pairs.

Drugs Alter Circumscribed TADS in a Cell-Type Specific Manner

Most of the human genome is separated into approximately 2,450 fundamental units of transcription called TADs, but about 5% of expressed genes and functional long noncoding RNAs are not found within these bounded 3D structures. TADs are delineated by circumscribed boundaries, often contain a plurality of functionally related genes that are controlled by intra-TAD enhancers, and are invariant across all cell types that have been studied to date. Few enhancers cross TAD boundaries in most cases unless the TAD boundary is destroyed by a SNP or other genetic variants. Differences in gene expression among different cell types are a function of which TADs are activated or repressed in that cell type. TADs exhibit specific histone modifications, are units of DNA replication timing, and specific and circumscribed sets of TADs and their trans-interacting TADs comprise drug-responsive and hormone-responsive co-regulation modules. The boundaries of TADs are relatively invariant between different human cell types. The strength of TAD boundaries can be classified into 5 distinct domains based on the amount of CTCF bound to the boundary and whether a super-enhancer is co-located on the TAD boundary.

The Regulatory Pharmacogenome Determines Drug Pharmacogenomic Networks

From recent studies, some basic principles of the pharmacoepigenome have emerged: (1) results from GWAS and PheWAS demonstrate that over 90% of causal single nucleotide polymorphisms (SNPs) are located within regulatory enhancers, while about 5% are located within protein-coding exons; (2) in adult humans, chromatin contacts between enhancers and promoters or coordinated promoters always precedes both gene transcription and alternative splicing of mRNAs that encode proteins; (3) histone modifications indicate the regulatory state of any given genomic regulatory element or gene; and (4) in all cases studied to date, causal genetic variants exhibit allele-specificity, regardless of whether the cells are diploid, tetraploid or octoploid. Numerous studies have demonstrated that it is possible to predict whether a genetic mutation such as a SNP located within an enhancer is causal using machine learning algorithms that have been trained on DNase I hypersensitivity, indicative of allele-specificity, as well as other characteristics of the epigenome including histone modifications associated with enhancers and promoters. The accuracy of the clinical utility of these machine-learning applications has been validated using known causal SNPs and comparing them to outputs of these software programs.

Recent research has demonstrated from our laboratory and those of other researchers have demonstrated the existence of a new class of pharmacodynamic and pharmacokinetic master regulator networks in chromatin whose function is to activate and repress large sets of interconnected genes that are contacted in chromatin space. Controllers of these pharmacogenomic regulatory networks represent a new class of druggable targets in humans, different from the last generation of epigenetic drugs consisting of writers, readers and erasers.

Enhancer and Super Enhancer SNPs Associated with Disease Risk and Drug Response are Key to the Discovery of Drug Pharmacogenomic Networks Causal mutations such as SNPs that are found within enhancers, promoters and splice sites profoundly alter chromatin state and can be used as "data probes" for the discovery of drug networks within the 3D spatial environment of chromatin located within the nucleus of a cell. Although there exists published literature that have described methods for the development of drug networks, even in complex tissues such as the human brain, the problem with current gene-gene and protein-protein regulatory pathways is: (1) They are based on the assumption that protein-coding genes and mutations within protein-coding exons represent the majority of primary, biologically relevant mechanisms, and/or (2) They look for similarities in the structure and catalytic properties of new compounds that mimic those of FDA-approved medications for a given indication or match the tissue-specific gene expression patterns to those of FDA-approved medications for a given indication. Recent research has shown that neither of these assumptions are very accurate for the discovery of new psychotropic drug candidates that provide better efficacy and less adverse events than existing medications. First, most significant SNP-trait associations for disease risk and drug response alter the function of enhancers located within the noncoding genome, not proteins, and genetic variants located within the introns of genes disrupt intragenic enhancers which may or may not regulate the expression of the gene in which they are located. SNPs located within protein-coding exons often disrupt alternative splicing of mRNA or may disrupt enhancers, such that any method that predicts a priori that a missense SNP will alter the protein product is not accurate. Also, many functional RNAs exist in the human genome, including long non-coding RNAs, which are not translated into protein. Second, the "guilt-by-association" approach used by programs such as the Library of Integrated Network-based Cellular Signatures (LINCS) program are based entirely on gene expression profiles in cell lines as surrogates to discover new drugs for human tissues such as the brain. The complexity of this human tissue requires a more nuanced and comprehensive interrogation approach than can be provided by surrogacy using cell line-dependent, "shot-gun" expression profiling.

SUMMARY

A method and system that detects regulatory drug networks in humans using bioinformatics and computational methods such as machine learning and deep learning. The foundation for these methods is the ability to reveal previously unrecognized drug pharmacogenomic networks through interrogation of pharmacogenomic regulatory interactions embedded within the functional three-dimensional (3D) topology of the human genome using mutations that stratify drug response in large human populations. These spatial regulatory interactions provide the architecture for the pharmacogenomic network for most psychotropic and anti-neoplastic drugs.

There now exists an enormous amount of extant data that can be used to computationally map drug pathways in lieu of additional experiments in animal and cellular models and without resorting to the use of sophisticated probabilistic inference methods. These knowledge-based methods described herein can be used to reconstruct drug pharmacogenomic networks acting in different cell types and tissues and deconstruct these networks into constitutive parts that mediate different on-target and off-target mechanisms of a drug, validated post hoc using bioinformatics analysis.

These methods differ from studies that require experimental perturbation of the biology of cells or tissues following drug exposure, or those that entirely depend on the centrality of learning machines for pathway mapping. An important part of the process of determining whether a single nucleotide polymorphism (SNP: may be a single base pair change or a short insertion/deletion) that has been significantly associated with a specific drug response is the use of different machine learning algorithms for determination of probable mechanistic causality. Nonetheless, the primary mapping methods are based on 3D genome structure and an existing knowledge base drawn from multiple public data sources and/or from experimental data or proprietary data.

FIG. 1D illustrates an exemplary model for how the system integrates and processes multi-scale data using machine learning and deep learning for pharmacogenomic network reconstruction. This strategy for mapping drug networks provides insight into the mechanistic on- and off-target effects, laying a foundation for subsequent preclinical studies;

FIG. 1E shows a method for the detection of drug pharmacogenomic networks in humans, which may be executed by a server device. The first step in the method includes extracting significant SNPs that have been associated with a specific drug response. The majority of these SNPs have been published in genome-wide association studies (GWAS) and phenome-wide association studies (PheWAS), and there is also a wealth of unbiased, peer-reviewed scientific publications where such data may be obtained. To improve the accuracy of the location of the SNP it is processed, by the server device, using the automated pharmacoepigenomics informatics pipeline (PIP) described with reference to FIGS. 4B, 4D, and 4E of U.S. patent application Ser. No. 15/977,347 filed on May 11, 2018, incorporated by reference herein. Once imputation and annotation has been performed to further characterize the SNP in its tissue context, multiple, accurate and validated machine learning algorithms trained on causal disease SNPs are applied to make a determination of probable mechanistic causality. In addition, missense SNPs, synonymous SNPs and SNPs located within exons that may be splice site donors or acceptors are characterized using machine learning. The output of this pipeline is the set of "permissive" candidate SNPs that have been shown to stratify drug response within human populations for a specific drug of interest. The next method steps executed by the server device include performing spatial genome classification using these causal SNPs to locate their target genes within the same TADs as these SNPs in the case of enhancers, and these enhancer SNPs are used to located the top ranking (e.g., the top three) statistically significant spatial contacts of their resident TADs within the genome through analysis of datasets generated using chromosome conformation capture methods, most typically generated from the Hi-C method. If the causal enhancer SNP resides in a TAD that has an empirically-determined strong boundary of strength III-V, characteristic of TAD boundaries containing genes involved in drug absorption, distribution, metabolism and excretion (ADME), then all of the intra-TAD genes controlled by the same enhancer within that TAD are saved for further evaluation. Similarly, if the top ranking statistically significant contacted "trans-TADs" in the spatial genome contain genes that are controlled by enhancers active in the same cell type and/or tissue where the drug acts, they are also saved for further evaluation.

The candidate gene set containing intra-TAD and trans-TAD genes is then evaluated for whether the genes in the candidate gene set have known network connections using a pathway analysis from for example, third party software. Genes that do form a statistically significant interconnected pathway, most commonly determined using Fisher's exact test, expressed in the tissue of interest for the drug of interest, comprise the preliminary set of candidate spatial network genes. Genes that are not significantly inter-connected with the others are discarded. This comprises the preliminary set of genes of the specific drug's spatial network.

Knowledge-based semi-automated and automated curation is then performed on this set comprising the specific drug's spatial network to evaluate genes that should be added or removed. First, each member of the gene set is thoroughly examined in the context of its defined function, including from primary scientific publications that have made an assessment of its function, in the context of the specific drug of interest. Second, the entire set of known mutations within each gene, defined in linear distance as +10 kilobases (Kb) from its transcriptional start site(s) and its stop codon is evaluated for its impact on known efficacy and adverse event mechanisms of the specific drug of interest. Mutations include SNPs, variable numbers of tandem repeats, duplications and large insertions or deletions. In this context, any functional relationship to a physiological process related to efficacy or adverse event of the specific drug of interest is included in the evaluation process. It is not restricted to pharmacogenomic impact on the specific drug response. Third, in complex tissues such as the human brain, the pattern of each gene's expression is compared to the neuroanatomical substrate where the specific drug of interest is known to act from other studies. For example, in the reconstruction of the ketamine spatial network, datasets from 24 functional neuroimaging studies are examined to determine which brain regions are metabolically active following ketamine administration in humans. Every gene in the preliminary set of genes of the ketamine spatial network is examined to see if its expression in human brain overlaps with the consensus neuromap derived from the 24 functional neuroimaging studies detailing the neuroanatomical substrate for ketamine action in human brain. To accomplish this task, microarray expression and in situ hybridization results from the Human Brain Atlas of the Allen Brain Science Institute and RNA-seq results from the National Institutes of Health's GTEx program are examined for each gene's neuroanatomical neuromap in the human brain. Genes whose expression patterns do not fit the consensus neuroanatomical neuromap are discarded.

The drug pharmacogenomic network gene set is again evaluated for whether each of the genes have known network connections using a pathway analysis, for example via third party software. Genes that do form a statistically significant interconnected pathway, most commonly determined using Fisher's exact test, expressed in the tissue of interest for the drug of interest comprise the preliminary set of candidate spatial network genes. Genes that are not significantly inter-connected with the others are discarded. This comprises the final set of genes of the specific drug's spatial network.

The next step of the method includes applying the iterative gene set optimization tool and algorithms for organizing the spatial network genes into functional subsets of genes, some of which comprise drug efficacy and adverse drug event sub-networks within the larger set of genes. This involves measures of similarity of input molecules derived from one or more of a multiplicity of data sources that are involved in the specific drug's mechanism of action(s), converting them into standardized human gene nomenclature and comparing them to the genes of the drug pharmacogenomic network. The output of this process is the entire set of genes of the specific drug's spatial network organized into its constitutive sub-networks, including efficacy and adverse event sub-networks.

The next steps of the method include providing scientific validation of the specific drug's spatial network organized into its constitutive sub-networks using for example, third party software applications in bioinformatics and biostatistics. These include the top ranking (e.g., top five) statistically significant terms from Gene Ontology or a medications database such as MedDRA, the top ranking (e.g., top five) canonical pathways determined by a pathway analysis such as via commercial or open source pathway analysis software programs, the top upstream xenobiotic regulators, and examples of mutational functional impairment of the spatial network and its sub-networks annotated using statistically-significant SNP-trait associations from GWAS and PheWAS.

After validation is performed, the specific drug's spatial network and its constitutive sub-networks may be stored in a database and provided to a client device for display.

The drug's spatial network and its constitutive sub-networks may be applied in several contexts. For example, different embodiments are presented in pharmacogenomic decision support for medication selection, drug re-purposing and in silico drug target discovery. One embodiment of clinical decision support is a method in which a reference drug pharmacogenomic network and its efficacy and adverse event sub-networks selected from a database of such spatial networks is matched to the specific drug efficacy and adverse event sub-networks of a patient. This comparison uses a method in deep learning in which co-training of efficacy metrics are undertaken between the reference sub-networks and the patient sub-networks and pattern matching scores are generated. The outputs are separate drug efficacy similarity score and a drug adverse event sub-similarity score. It should be noted that those trained in the art would recognize that a reference drug pharmacogenomic network and its constituent efficacy and adverse event sub-networks do not represent optimal profiles. Instead, they reflect the entirety of the drug's mechanisms of action, encompassing both the best and worst impacts the drug may have on an individual patient.

An embodiment of in silico drug discovery is the selection of a gene member, the PPP1R1B gene, of a set of genes in the ketamine spatial network, and is controlled by the same enhancer that controls the gene NEUROD2, a gene whose protein product is involved in neurogenesis, and is in significant spatial contacts with trans-TADs which contain the genes DRD2 and ADORA2A. Using the methods described herein to map the gene set interconnected with the PPP1R1B gene and evaluating the top Gene Ontology terms and canonical pathways associated with is pathway showed that it is very significantly involved in central nervous system (CNS) development, neuronal differentiation and neurogenesis. In addition, the PPP1R1B gene is expressed in a circumscribed set of human brain regions including the anterior caudate, nucleus accumbens and putamen, as are most of the 24 genes significantly interconnected with the gene, a neuroanatomical substrate that is involved in reward and addiction. Finally, PPP1R1B encodes a druggable phosphoprotein, which has been defined as "a bifunctional signal transduction molecule. Dopaminergic and glutamatergic receptor stimulation regulates its phosphorylation and function as a kinase or phosphatase inhibitor. As a target for dopamine, this gene may serve as a therapeutic target for neurologic and psychiatric disorders. This represents a potential druggable drug target identified using these methods.

The results of these methods include spatial networks for the drugs ketamine, valproic acid, lithium, lamotrigine, clozapine, and warfarin. Post hoc validation using bioinformatics methods for these drug pharmacogenomic networks is provided, as well as their knowledge-based segmentation of their efficacy and adverse event sub-networks using the methods of this disclosure. Details are also provided about specific efficacy and adverse event sub-networks to illustrate the output of the drug pharmacogenomic network identification system.

BRIEF DESCRIPTION OF THE DRAWINGS

FIG. 5A shows the "ball of yarn" model of chromatin organization of the human genome within a nucleus of a cell including chromatin spatial interactions. FIG. 5B shows a simple drug network with 3 super enhancers regulating 6 TADs and 4 TADs lacking super enhancer regulation and their trans-interactions in the spatial genome following exposure of the "ball of yarn" to a drug;

FIGS. 6A-6B show a simple example of how a SNP located within an enhancer in the network might disrupt the enhancer's contact with one of its target gene promoters in the TAD, leading to adverse drug events in a patient within a drug response cohort. FIG. 6A illustrates how different laboratory methods may be used to obtain measures from the chromatin spatial interactome in three dimensions and analyze the data as 2 dimensional plots of enhancer-gene promoter interactions. FIG. 6B depicts how a SNP may disrupt a chromatin loop between an enhancer and one of two gene promoters that it regulates within a TAD. This disruption removes the spatial connection between the enhancer and gene promoter 1 resulting in dysregulation of gene 1, resulting in an adverse event in this patient and its cohort in response to administration of the particular drug of interest;

FIG. 10 illustrates that TADs containing PK and HLA gene clusters have strong TAD boundaries and are associated with significant biological processes as determined by Gene Ontology;

FIGS. 11-1 and 11-2 illustrate a flow diagram representing a method for generating a reconstructed drug pharmacogenomic network and corresponding sub-networks for a drug of interest, including the human pharmacogenomic SNP input filter, the drug pharmacogenomic network reconstruction engine, and the iterative gene set optimization engine, outputting drug efficacy and adverse event sub-networks;

FIGS. 15-1 and 15-2 illustrate a flow diagram representing an exemplary method for using similarity scores to match a patient's drug efficacy and adverse events to that of a reference drug pharmacogenomic network for optimization of medication selection in clinical decision support;

FIGS. 22A-22B illustrate examples of disease risk and pharmacogenomic SNPs from GWAS that can be used to determine the proclivity of an individual patient to experience adverse events following valproic acid therapy, as indicated in FIG. 22A, or efficacy response efficacy, as indicated in FIG. 22B;

FIG. 24 lists the genes contained within the chromatin remodeling sub-network of the valproic acid pharmacogenomic network;

FIGS. 25A-25B list the genes contained within the neuroplasticity and efficacy sub-network of the valproic acid pharmacogenomic network;

FIGS. 26-1 and 26-2 list the genes contained within the adverse event sub-network of the valproic acid pharmacogenomic network;

FIG. 27 lists the genes contained within the pharmacokinetic and hormonal sub-network of the valproic acid pharmacogenomic network;

FIG. 30A is the ketamine pharmacogenomic glutamate receptor sub-network that is responsible for adverse events associated with drug as well as neurotransmission. FIG. 30B is the ketamine pharmacogenomic neuroplasticity sub-network that mediates ketamine's antidepressant response;

FIGS. 33A-33B illustrate examples of disease risk SNPs from GWAS that can be used to determine the proclivity of an individual patient to experience adverse events following ketamine therapy, as indicated in FIG. 33A, or antidepressant response efficacy, as indicated in FIG. 33B;

FIG. 34 lists the genes contained within the neuroplasticity and efficacy sub-network of the ketamine pharmacogenomic network;

FIG. 35 lists the genes contained within the chromatin remodeling and adverse event sub-network of the ketamine pharmacogenomic network;

FIG. 36 lists the genes contained within the pharmacokinetic and hormonal sub-network of the ketamine pharmacogenomic network;

FIG. 44 lists the genes contained within the chromatin remodeling sub-network of the lithium pharmacogenomic network;

FIG. 45 lists the genes contained within the neuroplasticity sub-network of the lithium pharmacogenomic network;

FIG. 46 lists the genes contained within the efficacy sub-network of the lithium pharmacogenomic network;

FIG. 47 lists the genes contained within the drug-induced weight gain (adverse event) sub-network of the lithium pharmacogenomic network;

FIG. 48 lists the genes contained within the drug-induced tremor (adverse event) sub-network of the lithium pharmacogenomic network;

FIG. 52 lists the genes contained within the chromatin remodeling sub-network of the lamotrigine pharmacogenomic network;

FIGS. 53-1 and 53-2 list the genes contained within the neuroplasticity sub-network of the lamotrigine pharmacogenomic network;

FIG. 54 lists the genes contained within the adverse event sub-network of the lamotrigine pharmacogenomic network;

FIG. 55 lists the genes contained within the pharmacokinetic sub-network of the lamotrigine pharmacogenomic network;

FIG. 59 lists the genes contained within the chromatin remodeling sub-network of the clozapine pharmacogenomic network;

FIGS. 60-1 and 60-2 list the genes contained within the neuroplasticity sub-network of the clozapine pharmacogenomic network;

FIGS. 61-1 and 61-2 list the genes contained within the adverse event sub-network of the clozapine pharmacogenomic network;

FIG. 62 lists the genes contained within the pharmacokinetic sub-network of the clozapine pharmacogenomic network; FIG. 63C shows the gene set enrichment for the warfarin anticoagulation sub-network and FIG. 63D shows the gene enrichment for the warfarin bleeding and vascular occlusion sub-network.

DETAILED DESCRIPTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

This section presents a detailed description of the drug pharmacogenomic network identification system and its application to pharmacophenomic decision support for medication selection and for in silico discovery of pharmacodynamic drug targets within biological pathways. The methodological description is presented first, as well as its applications in clinical medicine and pharmaceutical research, followed by several exemplary illustrations of drug pharmacogenomic networks. The examples are non-limiting, and related variations of the methods will be apparent to one who is skilled in the art are intended to been encompassed by the appended claims.

The pharmacogenomic network identification system produces models of pharmacogenomic regulatory networks and their constituent sub-networks using a contemporary knowledge base that includes the functional topology of pharmacogenomic genome architecture, 3D molecular circuits within chromatin that control gene expression and mRNA splicing, and the drug-specific geometric expansion and contraction of TADs and their pharmacogenomics connections regulated by super enhancers that impact enhancer-promoter and promoter-promoter interactions.

Figure 8A:
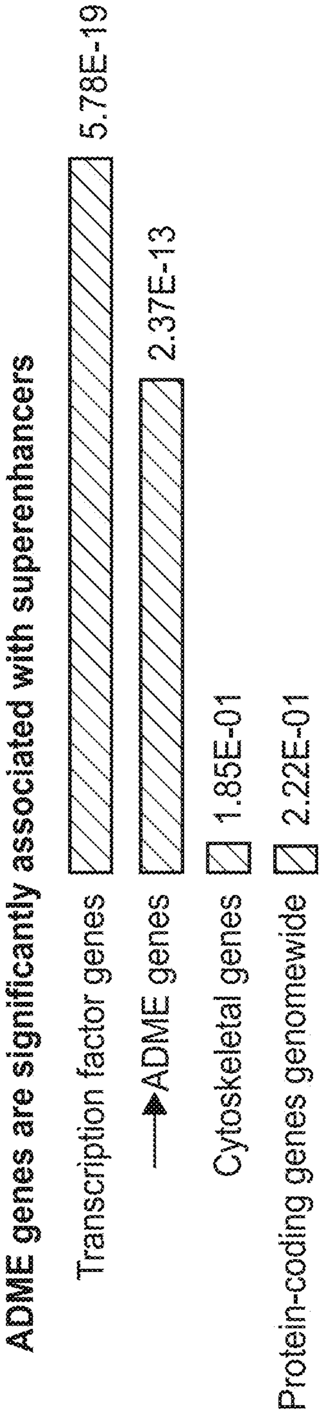
FIG. 8A illustrates the nature of significant associations between ADME genes and super-enhancers in humans.
Figure 8B:
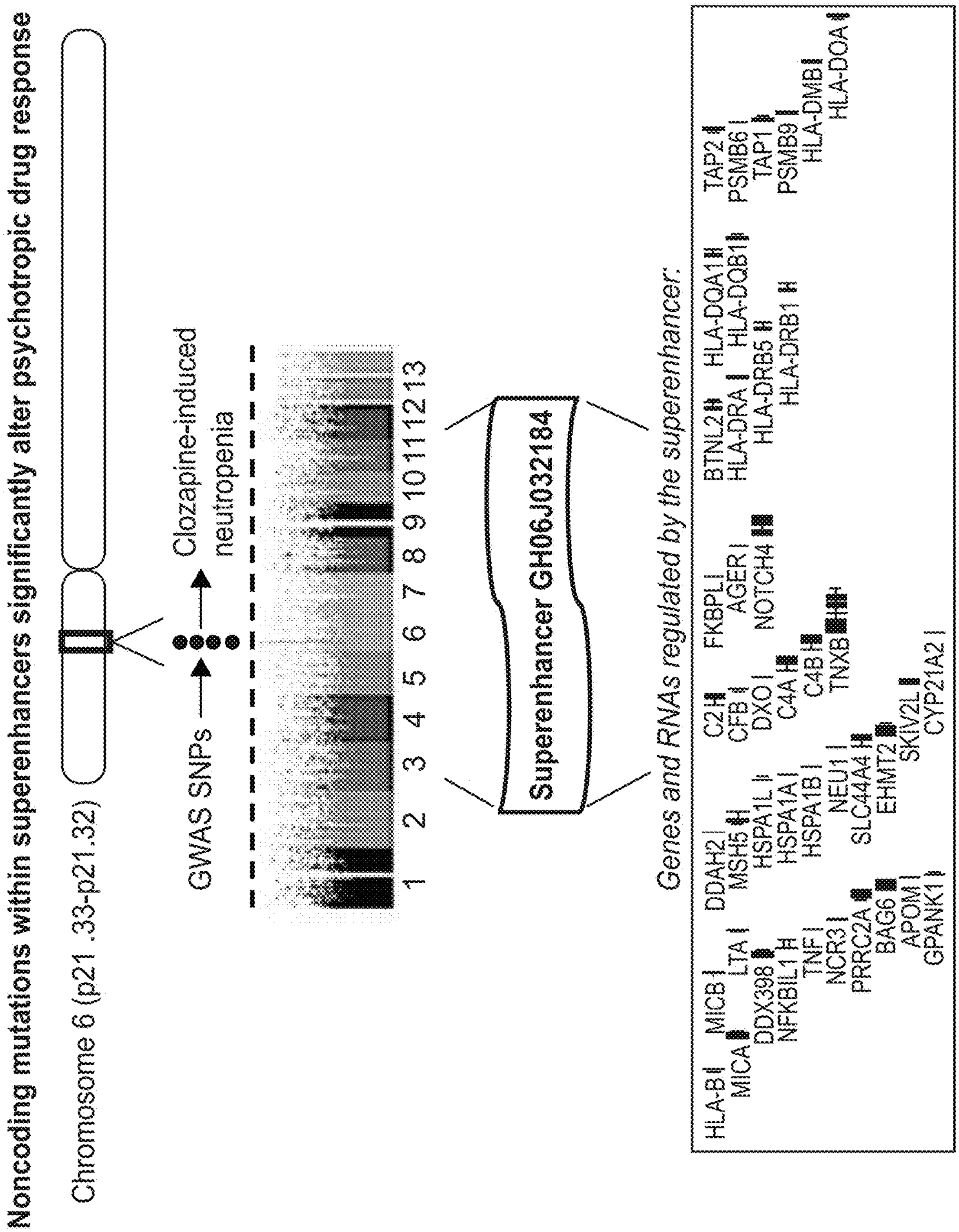
FIG. 8B shows the association between noncoding variations within super enhances which can significantly alter psychotropic drug response.

As shown in FIG. 8, the nature of these interactions include significant association of genes that encode proteins involved in absorption, distribution, metabolism and excretion (ADME) of xenobiotic drugs—one example consists of known mutations within the super enhancer GH06J032184, responsible for occurrence of the adverse drug event called neutropenia, in certain individuals following treatment with the antipsychotic medication clozapine.

The reconstructed drug pharmacogenomic networks described herein are inextricable from those that mediate disease etiology, providing another avenue in which to investigate pharmacological mechanisms of action. The drug pharmacogenomic networks adapt over time to intrinsic and extrinsic stimuli based on the reactivity chromatin plasticity in which they are embedded, which accounts for pharmacogenomic variation among humans. This determines an individual patient's response to a medication, including adverse drug events, and examples of this variation resulting from different proportional representation of sub-networks within a drug's pharmacogenomic network among patients, will be provided as instances of the output of this system and its methods.

Generally speaking, techniques for identifying a pharmacogenomic network of a drug may be implemented in one or several client devices, one or several network servers, or a system that includes a combination of these devices. However, for clarity, the examples below focus primarily on an embodiment in which a drug pharmacogenomic network server obtains SNPs from human clinical studies that have been demonstrated as having significant association with response and adverse events with regard to the particular drug of interest, or they may include disease or trait risk SNPs. The drug pharmacogenomic network server compares the SNPs to SNPs reported from genome-wide association studies (GWAS), biobanks, phenome-wide association studies (PheWAS), and other candidate gene studies to identify additional SNPs linked to the SNPs using characteristics of three-dimensional (3D) genome topology to generate a set of permissive candidate variants.

Then the drug pharmacogenomic network server performs a bioinformatics analysis on the each of the permissive candidate variants to filter the set of SNPs into a subset of intermediate candidate variants based on regulatory function, variant dependence, a presence of target gene relationships for the permissive candidate variants, and/or whether the permissive candidate variants are non-synonymous or synonymous coding variants that do not impact protein, but are involved in the regulation of gene expression. Furthermore, the drug pharmacogenomic network server performs a pathway analysis on target genes associated with the subset of intermediate candidate variants to filter the target genes to identify a set of genes which are causally related to the particular drug.

The drug pharmacogenomic network server then identifies a drug pharmacogenomic network for the particular drug of interest based on the identified set of genes and provides an indication of the drug pharmacogenomic network for display to a client device. For example, the indication of the drug pharmacogenomic network may include the name of the drug of interest, names and/or graphical depictions of each of the genes in the pharmacogenomic network, and names and/or graphical depictions of each of the sub-networks within the pharmacogenomic network and the genes within each sub-network.

The drug pharmacogenomic network server may analyze data described herein such as genomic data and spatial contact data using various machine learning techniques, including, but not limited to regression algorithms (e.g., ordinary least squares regression, linear regression, logistic regression, stepwise regression, multivariate adaptive regression splines, locally estimated scatterplot smoothing, etc.), instance-based algorithms (e.g., k-nearest neighbors, learning vector quantization, self-organizing map, locally weighted learning, etc.), regularization algorithms (e.g., Ridge regression, least absolute shrinkage and selection operator, elastic net, least-angle regression, etc.), decision tree algorithms (e.g., classification and regression tree, iterative dichotomizer 3, C4.5, C5, chi-squared automatic interaction detection, decision stump, M5, conditional decision trees, etc.), clustering algorithms (e.g., k-means, k-medians, expectation maximization, hierarchical clustering, spectral clustering, mean-shift, density-based spatial clustering of applications with noise, ordering points to identify the clustering structure, etc.), association rule learning algorithms (e.g., apriori algorithm, Eclat algorithm, etc.), Bayesian algorithms (e.g., naïve Bayes, Gaussian naïve Bayes, multinomial naïve Bayes, averaged one-dependence estimators, Bayesian belief network, Bayesian network, etc.), artificial neural networks (e.g., perceptron, Hopfield network, radial basis function network, etc.), deep learning algorithms (e.g., multilayer perceptron, deep Boltzmann machine, deep belief network, convolutional neural network, stacked auto-encoder, generative adversarial network, etc.), dimensionality reduction algorithms (e.g., principal component analysis, principal component regression, partial least squares regression, Sammon mapping, multidimensional scaling, projection pursuit, linear discriminant analysis, mixture discriminant analysis, quadratic discriminant analysis, flexible discriminant analysis, factor analysis, independent component analysis, non-negative matrix factorization, t-distributed stochastic neighbor embedding, etc.), ensemble algorithms (e.g., boosting, bootstrapped aggregation, AdaBoost, stacked generalization, gradient boosting machines, gradient boosted regression trees, random decision forests, etc.), reinforcement learning (e.g., temporal difference learning, Q-learning, learning automata, State-Action-Reward-State-Action, etc.), support vector machines, mixture models, evolutionary algorithms, probabilistic graphical models, etc.

Figure 1A:
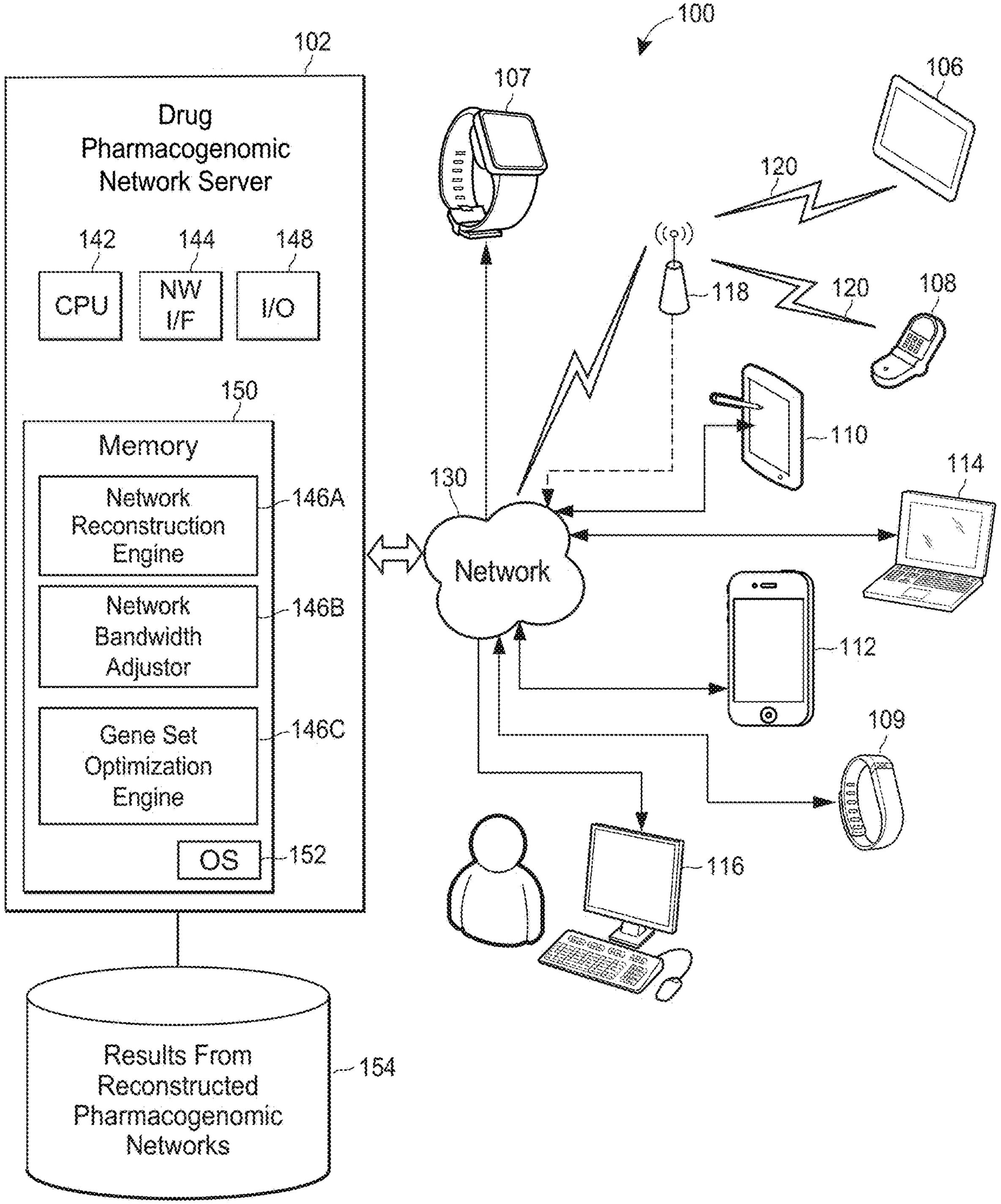
FIG. 1A illustrates a block diagram of a computer network and system on which an exemplary drug pharmacogenomic network identification system may operate in accordance with the presently described embodiments.

Referring to FIG. 1A, an example pharmacogenomic network identification system 100 identifies pharmacogenomic networks for various drugs. The pharmacogenomic network identification system 100 includes a drug pharmacogenomic network server 102 and a plurality of client devices 106-116 which may be communicatively connected through a network 130, as described below. In an embodiment, the drug pharmacogenomic network server 102 and the client devices 106-116 may communicate via wireless signals 120 over a communication network 130, which can be any suitable local or wide area network(s) including a WiFi network, a Bluetooth network, a cellular network such as 3G, 4G, Long-Term Evolution (LTE), 5G, the Internet, etc. In some instances, the client devices 106-116 may communicate with the communication network 130 via an intervening wireless or wired device 118, which may be a wireless router, a wireless repeater, a base transceiver station of a mobile telephony provider, etc. The client devices 106-116 may include, by way of example, a tablet computer 106, a smart watch 107, a network-enabled cell phone 108, a wearable computing device such as Google Glass™ or a Fitbit® 109, a personal digital assistant (PDA) 110, a mobile device smart-phone 112 also referred to herein as a “mobile device,” a laptop computer 114, a desktop computer 116, wearable biosensors, a portable media player (not shown), a phablet, any device configured for wired or wireless RF (Radio Frequency) communication, etc. Moreover, any other suitable client device that records genomic data for subjects, receives pharmacogenomics datasets, or displays indications of pharmacogenomic networks and/or sub-networks may also communicate with the drug pharmacogenomic network server 102.

Figures 1, 15:
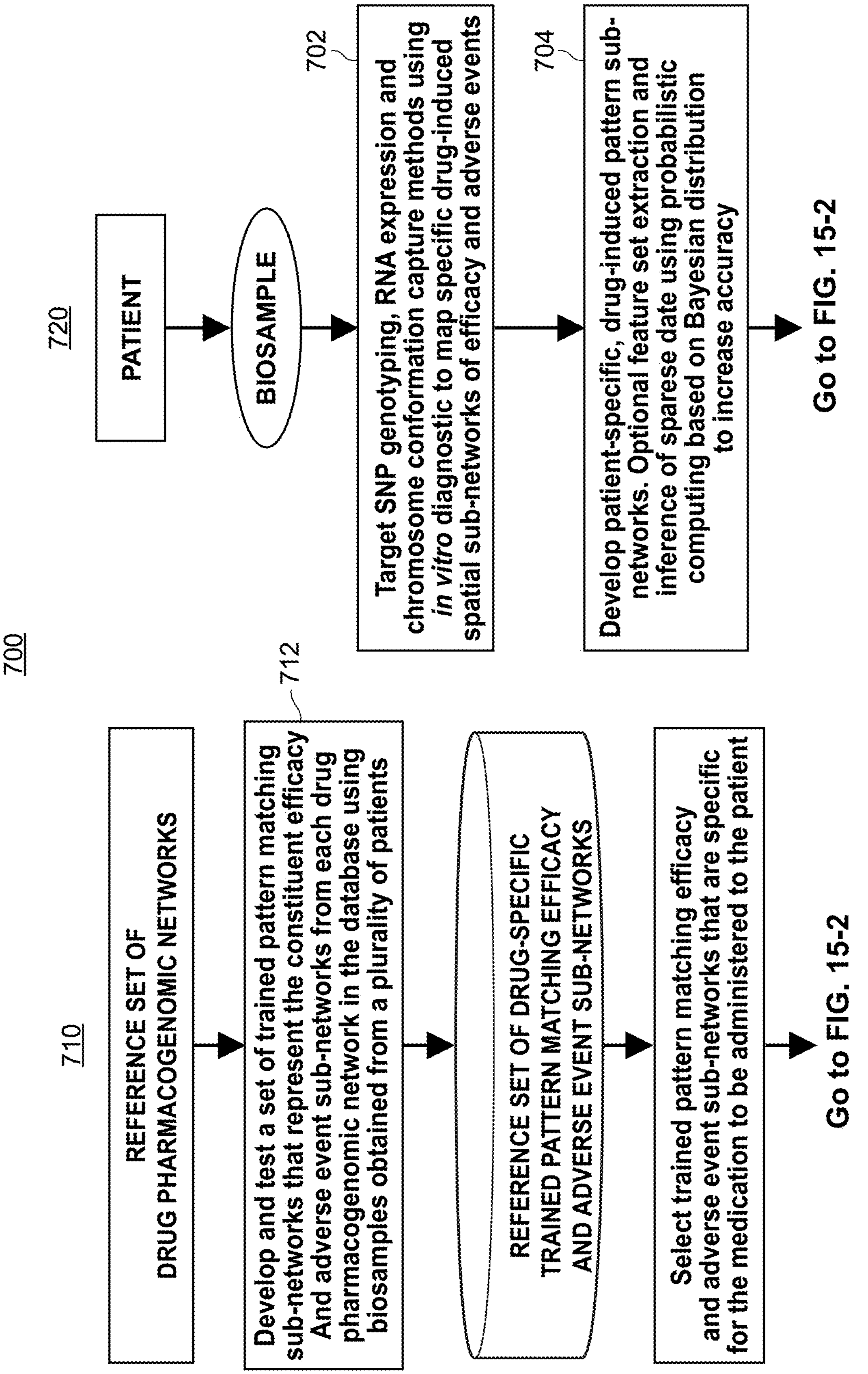
Figures 2, 15:
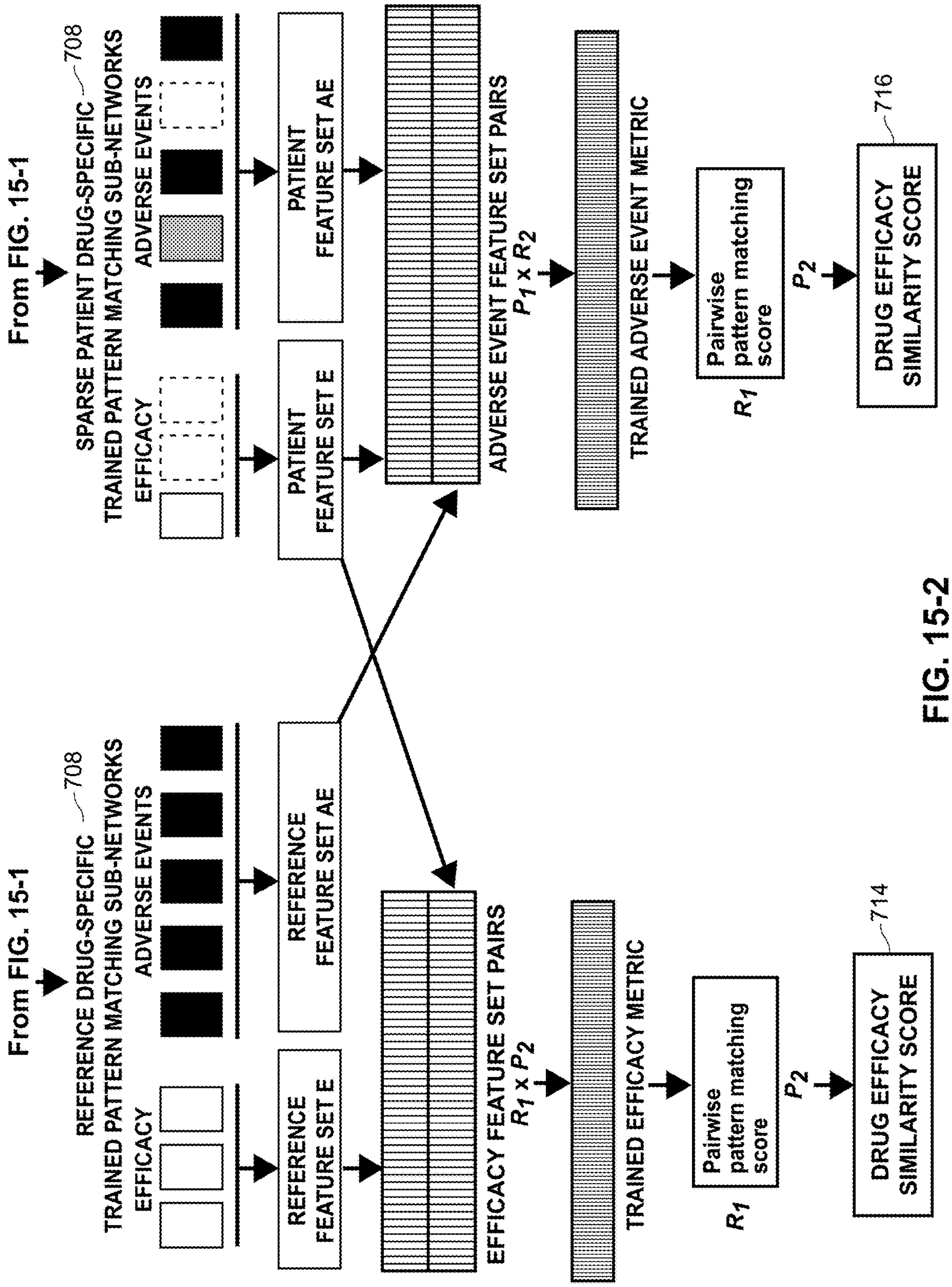

Each of the client devices 106-116 may interact with the drug pharmacogenomic network server 102 to identify a drug of interest for determining a corresponding pharmacogenomic network. Each client device 106-116 may also interact with the drug pharmacogenomic network server 102 to receive an indication of a pharmacogenomic network and/or several pharmacogenomic sub-networks within the pharmacogenomic network for the drug of interest. The client device 106-116 may present the indication via a user interface for display to a health care professional or researcher, such as a display exhibiting the degree of overlap of drug-specific topology maps based on what is shown in FIG. 17, or as similarity scores as shown in FIG. 15.

In an example implementation, the drug pharmacogenomic network server 102 may be a cloud based server, an application server, a web server, etc., and includes a memory 150, one or more processors (CPU) 142 such as a microprocessor coupled to the memory 150, a network interface unit 144, and an I/O module 148 which may be a keyboard or a touchscreen, for example.

The drug pharmacogenomic network server 102 may also be communicatively connected to a database 154 of genomic data including data from human clinical studies, biobanks, GWAS, and PheWAS studies.

The memory 150 may be tangible, non-transitory memory and may include any types of suitable memory modules, including random access memory (RAM), read only memory (ROM), flash memory, other types of persistent memory, etc. The memory 150 may store, for example instructions executable of the processors 142 for an operating system (OS) 152 which may be any type of suitable operating system such as modem smartphone operating systems, for example. The memory 150 may also store, for example instructions executable on the processors 142 for a network reconstruction engine 146A, a drug pharmacogenomic network bandwidth adjustor 146B, and a gene set optimization engine 146C. The drug pharmacogenomic network server 102 is described in more detail below with reference to FIG. 1B. In some embodiments, the network reconstruction engine 146A, drug pharmacogenomic network bandwidth adjustor 146B, and gene set optimization engine 146C may be a part of one or more of the client devices 106-116, the drug pharmacogenomic network server 102, or a combination of the drug pharmacogenomic network server 102 and the client devices 106-116.

In any event, the network reconstruction engine 146A may receive a request to identify a drug pharmacogenomic network for a particular drug of interest from a client device 106-116 or from a database of pre-existing reconstructed drug pharmacogenomic networks. The client device 106-116 may also provide SNPs from human clinical studies, GWAS studies, PheWAS studies, etc., that have been demonstrated as having significant association with response and adverse events with regard to the particular drug of interest, or disease risk SNPs from GWAS that discriminate a drug's pharmacogenomic sub-networks. In other embodiments, the network reconstruction engine 146A may obtain the SNPs from the database 154. The network reconstruction engine 146A then generates a set of permissive candidate variants based on the obtained SNPs and additional SNPs linked to the obtained SNPs according to a TAD boundary, within adjacent TADs regulated by a super enhancer, or distant trans-interactions determined from chromosome conformation capture methods. Moreover, the network reconstruction engine 146A performs a bioinformatics analysis on the each of the permissive candidate variants to filter the set of SNPs into a subset of intermediate candidate variants and performs a pathway analysis on target genes associated with the filtered set to identify a set of genes which are causally related to the particular drug. The network reconstruction engine 146A identifies a drug pharmacogenomic network for the particular drug of interest based on the identified set of genes and provides an indication of the drug pharmacogenomic network for display via a user interface of the client device 106-116.

The drug pharmacogenomic network server 102 may communicate with the client devices 106-116 via the network 130. The digital network 130 may be a proprietary network, a secure public Internet, a virtual private network and/or some other type of network, such as dedicated access lines, plain ordinary telephone lines, satellite links, combinations of these, etc. Where the digital network 130 comprises the Internet, data communication may take place over the digital network 130 via an Internet communication protocol.

Figure 1B:
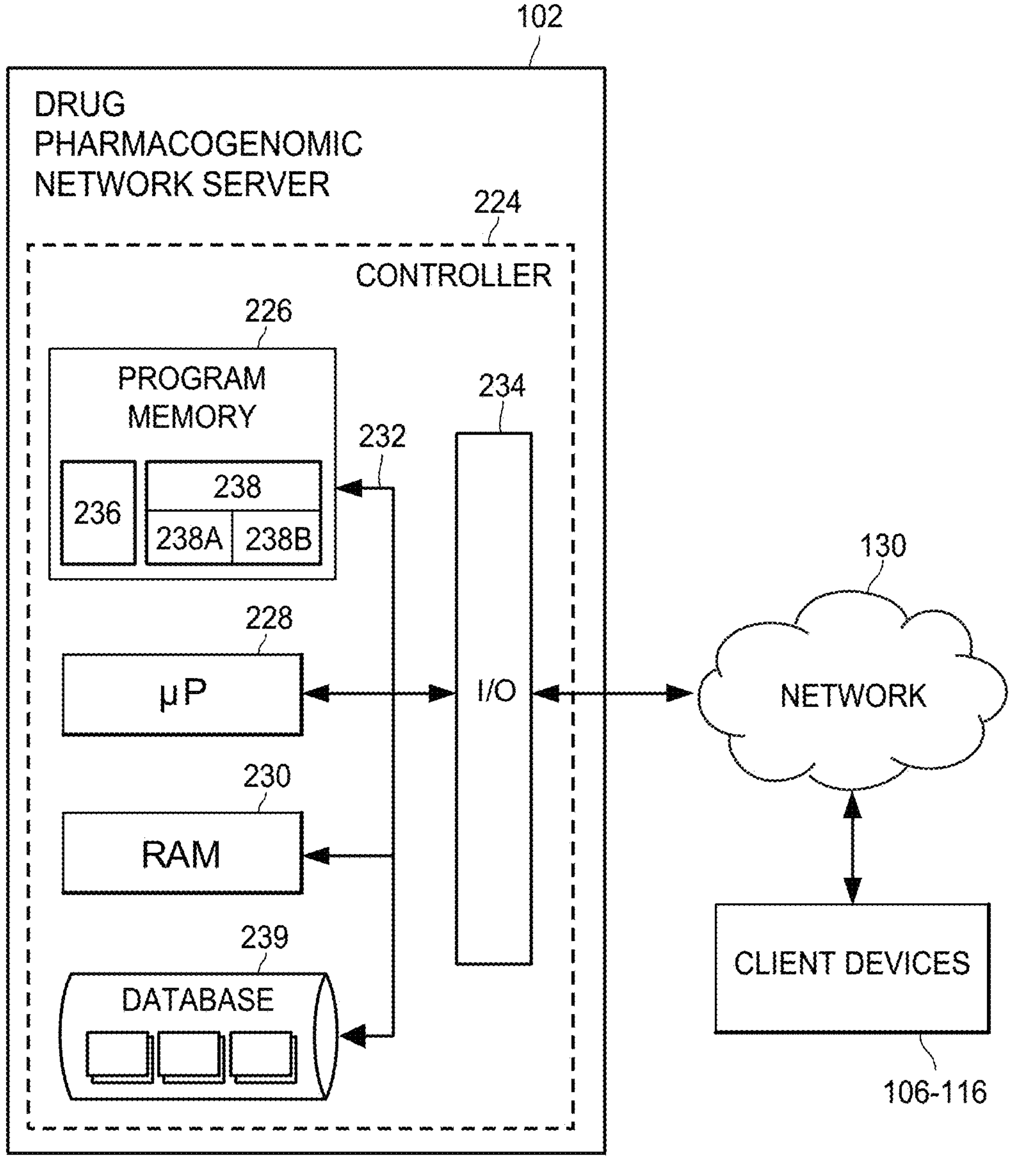
FIG. 1B is a block diagram of an exemplary drug pharmacogenomic network server that can operate in the system of FIG. 1A in accordance with the presently described embodiments.

Turning now to FIG. 1B, the drug pharmacogenomic network server 102 may include a controller 224. The controller 224 may include a program memory 226, a microcontroller or a microprocessor (MP) 228, a random-access memory (RAM) 230, and/or an input/output (I/O) circuit 234, all of which may be interconnected via an address/data bus 232.

In some embodiments, the controller 224 may also include, or otherwise be communicatively connected to, a database 239 or other data storage mechanism (e.g., one or more hard disk drives, optical storage drives, solid state storage devices, etc.). The database 239 may include data such as genomic data, pharmacogenomic network display templates, web page templates and/or web pages, and other data necessary to interact with users through the network 130. The database 239 may include similar data as the database 154 described above with reference to FIG. 1A.

It should be appreciated that although FIG. 1B depicts only one microprocessor 228, the controller 224 may include multiple microprocessors 228. Similarly, the memory of the controller 224 may include multiple RAMs 230 and/or multiple program memories 226.

Although FIG. 1B depicts the I/O circuit 234 as a single block, the I/O circuit 234 may include a number of different types of I/O circuits. The controller 224 may implement the RAM(s) 230 and/or the program memories 226 as semiconductor memories, magnetically readable memories, and/or optically readable memories, for example.

As shown in FIG. 1B, the program memory 226 and/or the RAM 230 may store various applications for execution by the microprocessor 228. For example, a user-interface application 236 may provide a user interface to the drug pharmacogenomic network server 102, which user interface may, for example, allow a system administrator to configure, troubleshoot, or test various aspects of the server's operation. A server application 238 may operate to receive a request to identify a drug pharmacogenomic network for a particular drug of interest, identify a drug pharmacogenomic network and pharmacogenomics sub-networks for the particular drug, and transmit an indication of the drug pharmacogenomic network to a client device 106-116. The server application 238 may be a single module 238 or a plurality of modules 238A, 238B, such as the network reconstruction engine 146A, the drug pharmacogenomic network bandwidth adjustor 146B, and the gene set optimization engine 146C.

While the server application 238 is depicted in FIG. 1B as including two modules, 238A and 238B, the server application 238 may include any number of modules accomplishing tasks related to implementation of the drug pharmacogenomic network server 102. Moreover, it will be appreciated that although only one drug pharmacogenomic network server 102 is depicted in FIG. 1B, multiple drug pharmacogenomic network servers 102 may be provided for the purpose of distributing server load, serving different web pages, etc. These multiple drug pharmacogenomic network servers 102 may include a web server, an entity-specific server (e.g. an Apple® server, etc.), a server that is disposed in a retail or proprietary network, etc.

Figure 1C:
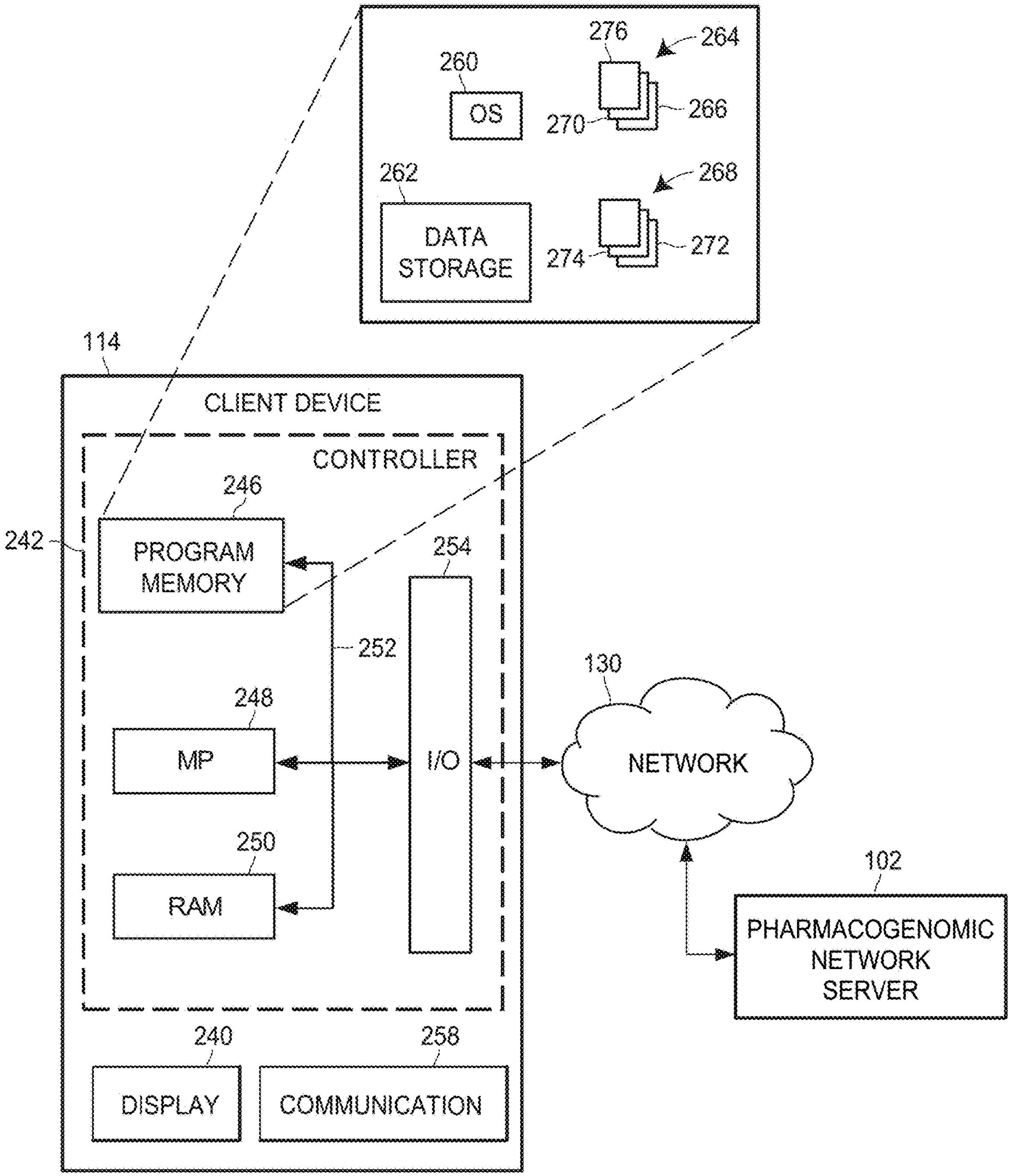
FIG. 1C is a block diagram of an exemplary client device that can operate in the system of FIG. 1A in accordance with the presently described embodiments.

Referring now to FIG. 1C, the laptop computer 114 (or any of the client devices 106-116) may include a display 240, a communication unit 258, a user-input device (not shown), and, like the drug pharmacogenomic network server 102, a controller 242. Similar to the controller 224, the controller 242 may include a program memory 246, a microcontroller or a microprocessor (MP) 248, a random-access memory (RAM) 250, and/or an input/output (I/O) circuit 254, all of which may be interconnected via an address/data bus 252. The program memory 246 may include an operating system 260, a data storage 262, a plurality of software applications 264, and/or a plurality of software routines 268. The operating system 260, for example, may include Microsoft Windows®, OS X®, Linux®, Unix®, etc. The data storage 262 may include data such as application data for the plurality of applications 264, routine data for the plurality of routines 268, and/or other data necessary to interact with the drug pharmacogenomic network server 102 through the digital network 130. In some embodiments, the controller 242 may also include, or otherwise be communicatively connected to, other data storage mechanisms (e.g., one or more hard disk drives, optical storage drives, solid state storage devices, etc.) that reside within the laptop computer 114.

The communication unit 258 may communicate with the drug pharmacogenomic network server 102 via any suitable wireless communication protocol network, such as a wireless telephony network (e.g., GSM, CDMA, LTE, etc.), a Wi-Fi network (802.11 standards), a WiMAX network, a Bluetooth network, etc. The user-input device (not shown) may include a "soft" keyboard that is displayed on the display 240 of the laptop computer 114, an external hardware keyboard communicating via a wired or a wireless connection (e.g., a Bluetooth keyboard), an external mouse, a microphone for receiving voice input or any other suitable user-input device. As discussed with reference to the controller 224, it should be appreciated that although FIG. 1C depicts only one microprocessor 248, the controller 242 may include multiple microprocessors 248. Similarly, the memory of the controller 242 may include multiple RAMs 250 and/or multiple program memories 246. Although the FIG. 1C depicts the I/O circuit 254 as a single block, the I/O circuit 254 may include a number of different types of I/O circuits. The controller 242 may implement the RAM(s) 250 and/or the program memories 246 as semiconductor memories, magnetically readable memories, and/or optically readable memories, for example.

The one or more processors 248 may be adapted and configured to execute any one or more of the plurality of software applications 264 and/or any one or more of the plurality of software routines 268 residing in the program memory 246, in addition to other software applications. One of the plurality of applications 264 may be a client application 266 that may be implemented as a series of machine-readable instructions for performing the various tasks associated with receiving information at, displaying information on, and/or transmitting information from the laptop computer 114.

One of the plurality of applications 264 may be a native application and/or web browser 270, such as Apple's Safari®, Google Chrome™, Microsoft Internet Explorer®, and Mozilla Firefox® that may be implemented as a series of machine-readable instructions for receiving, interpreting, and/or displaying web page information from the drug pharmacogenomic network server 102 while also receiving inputs from a user such as a health care professional or researcher. Another application of the plurality of applications may include an embedded web browser 276 that may be implemented as a series of machine-readable instructions for receiving, interpreting, and/or displaying web page information from the drug pharmacogenomic network server 102.

One of the plurality of routines may include a pharmacogenomic network display routine 272 which obtains an indication of a pharmacogenomic network including the name of the drug of interest, names and/or graphical depictions of each of the genes in the pharmacogenomic network, and names and/or graphical depictions of each of the sub-networks within the pharmacogenomic network and the genes within each sub-network and presents the indication on the display 240. Another routine in the plurality of routines may include a pharmacogenomic network request routine 274 which obtains a request to identify a pharmacogenomic network for a particular drug of interest and transmits the request to the drug pharmacogenomic network server 102.

Preferably, a user may launch the client application 266 from a client device, such as one of the client devices 106-116 to communicate with the drug pharmacogenomic network server 102 to implement the pharmacogenomic network identification system 100. Additionally, the user may also launch or instantiate any other suitable user interface application (e.g., the native application or web browser 270, or any other one of the plurality of software applications 264) to access the drug pharmacogenomic network server 102 to realize the pharmacogenomic network identification system 100.

Figures 1, 11:
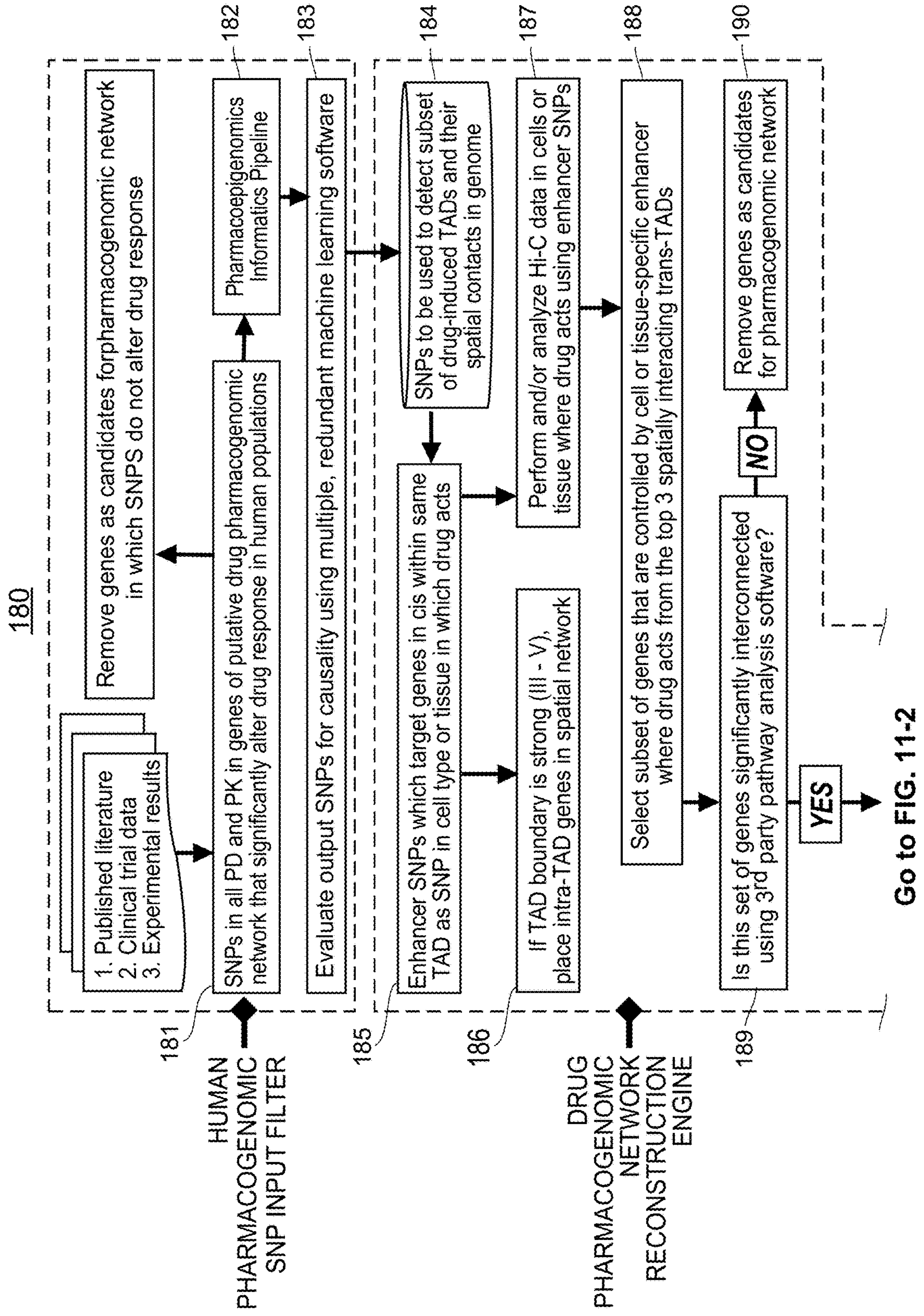
Figures 2, 11:
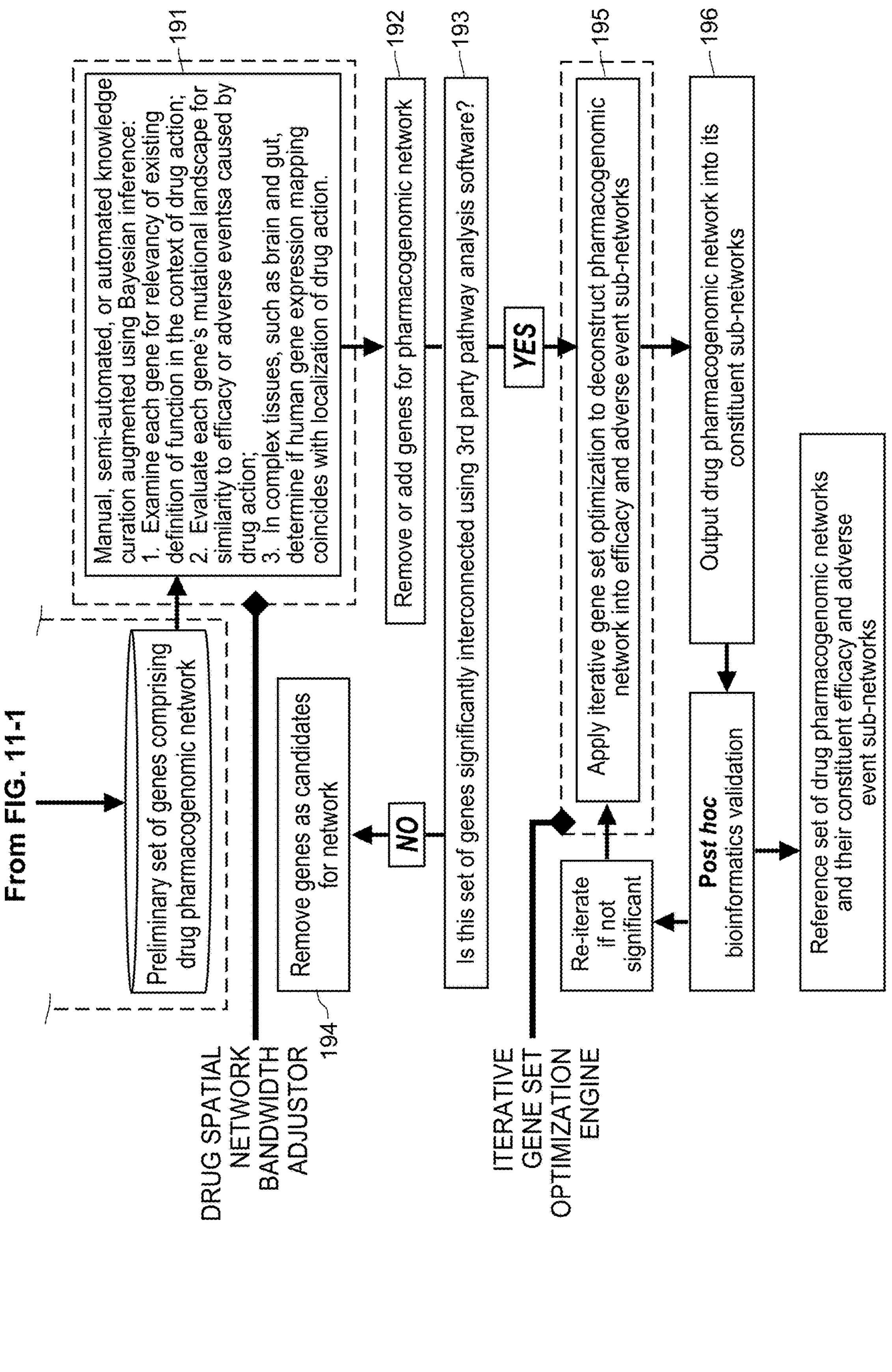

To identify a pharmacogenomic network for a particular drug of interest, the drug pharmacogenomic network server 102 executes the general method 180 as illustrated in FIG. 11. In some embodiments, the method 180 may be implemented in a set of instructions stored on a non-transitory computer-readable memory and executable on one or more processors on the drug pharmacogenomic network server 102. For example, the method 180 may be performed by the network reconstruction engine 146A, the drug pharmacogenomic network bandwidth adjustor 146B, and the gene set optimization engine 146C.

Figure 2:
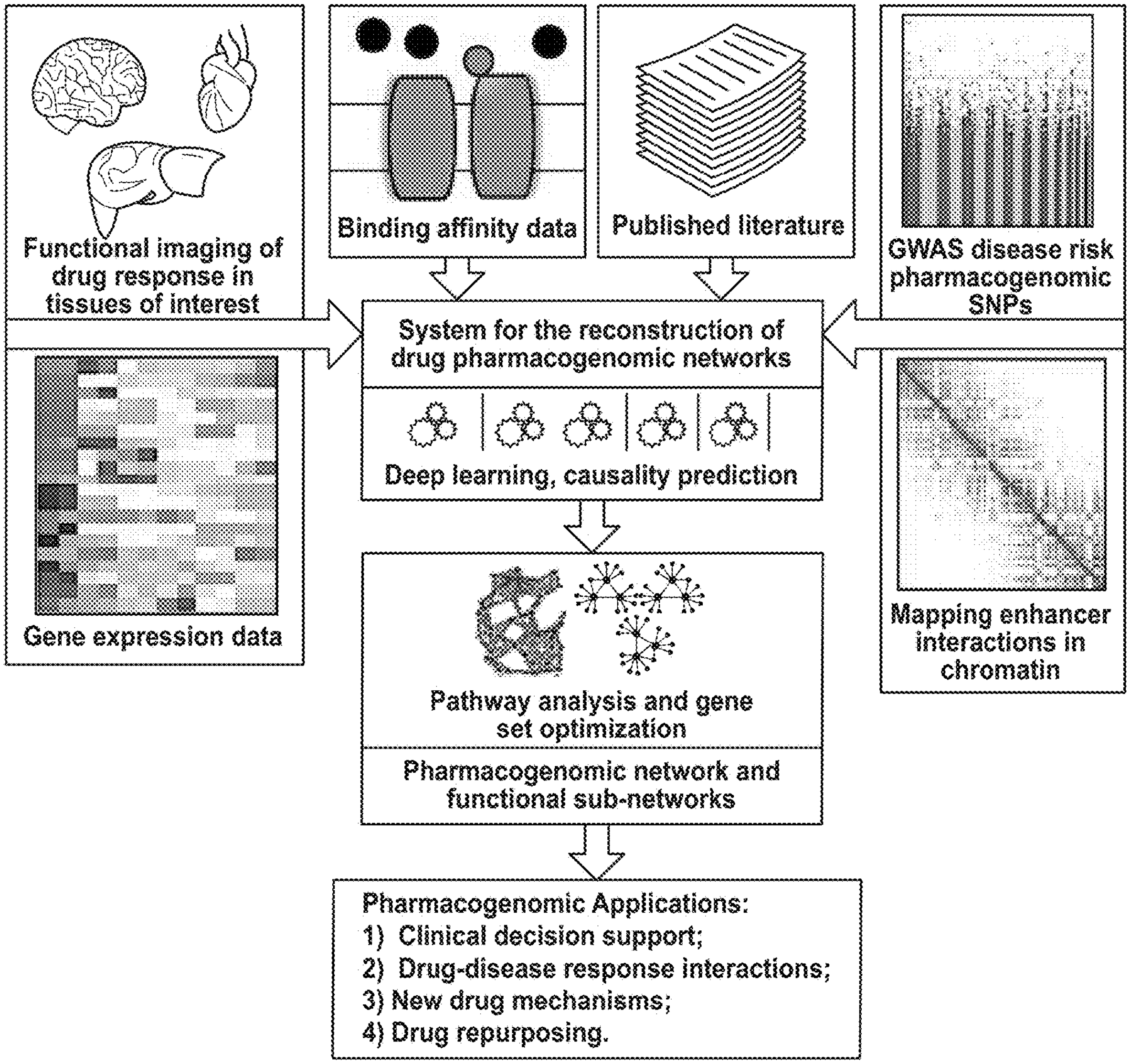
FIG. 2 illustrates an exemplary model for how the system integrates and processes multi-scale data using machine learning and deep learning for pharmacogenomic network reconstruction. This strategy for mapping drug networks provides insight into the mechanistic on- and off-target effects, laying a foundation for subsequent preclinical studies.

FIG. 2 illustrates the integration of multi-scale data and processing by the system 100. The methods and system are based on the nature of drug pharmacogenomic networks, that consists of enhancer and super enhancer networks that are activated or suppressed in the same human cell types in which the drug first acts. This may be accomplished by matching changes in gene expression caused by a drug or other therapeutic compared to a placebo or control with higher-order structures where the drug first acts, determining whether SNPs associated with drug's pharmacogenomic network and sub-networks act in these human tissues, and assessing whether enhancer and super enhancer regulatory elements are localized to the circumscribed target anatomical substrate. Machine learning, deep learning, reinforcement learning, and other methods in artificial intelligence may be used where applicable to perform machine-executable steps in the system.

A detailed overview of one embodiment of the system 100 is shown in FIG. 11. This system combines automated executables with semi-manual curation comprising a human pharmacogenomic SNP filter, which may accept both SNPs that impact drug response or disease risk. This is followed by a drug-specific pharmacogenomic network reconstruction engine with a drug spatial network bandwidth adjustor, followed by iterative gene set optimization for deconstruction of the drug-specific pharmacogenomic network into is component functional sub-networks.

Selection of Gene Variants Using the Human Pharmacogenomic SNP Input Filter

At block 181, the drug pharmacogenomic network server 102 obtains SNPs from human clinical studies that have demonstrated significant association with response and adverse events to the drug of interest, or disease risk SNPs which can be used to discriminate the representation within a patient's regulatory genome the relative weights of the efficacy and adverse event sub-networks. Since the location of a SNP associated with the trait under study has been, in most cases, inaccurately assigned to the nearest gene or nearby candidate gene in the published literature and GWAS per the linear sequence of the reference human genome assembly, accurate localization using imputation and annotation techniques are used to determine the actual location of the reported SNP.

New research has several important implications for the drug pharmacogenomic network identification system. First, new drug target mechanisms can be identified by collecting pharmacogenomic network outputs in a training set through the use of computer vision-based alterations in 3D genome architecture caused by permissive SNPs using deep learning (machine learning) and validation using correspondence to known drug-induced genome-wide alterations in genome architecture. Second, the clustering of new drug target mechanisms in previously defined but incompletely informed biological pathways will increase the probability of success.

Third, insight gained using 3D genome architecture to determine drug targets from drug response and disease risk SNPs will lead to a next generation of drug candidates and greatly enhance the accuracy of pharmacogenomic diagnostics.

Figure 3:
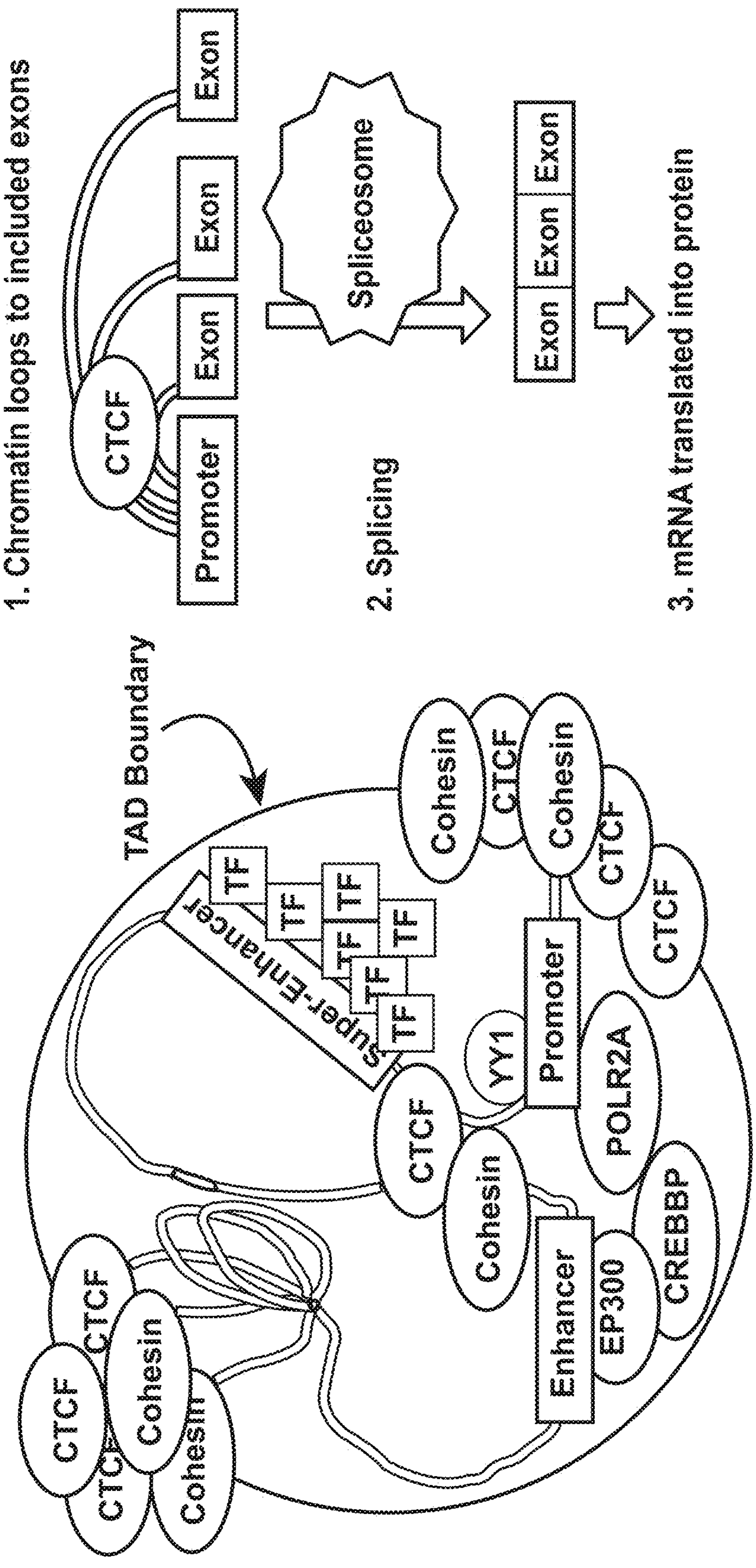
FIG. 3 illustrates an example of a TAD containing the gene promoter(s), enhancer, super enhancer, architectural proteins contained within the TAD boundary and subsequent chromatin looping of the promoter to different exons during alternative splicing of a gene.

FIG. 3 illustrates the nature of the organization of TADs, including the key enhancer and promoter transcription factors CREBBP (CEB binding protein), EP300 (E1A binding protein P300), POLR2A (RNA polymerase II subunit A), and YY1 (Yin Yang transcription factor 1) and the TAD boundary proteins and chromatin loop-binding proteins cohesion and CTCF (CCCTC-binding protein). In addition to enhancer-promoter and promoter-promoter pairs, adjacent TADs also contain super enhancers. The chromatin loop protein CTCF also is involved in pre-mRNA splicing as shown in FIG. 3.

Figure 4A:
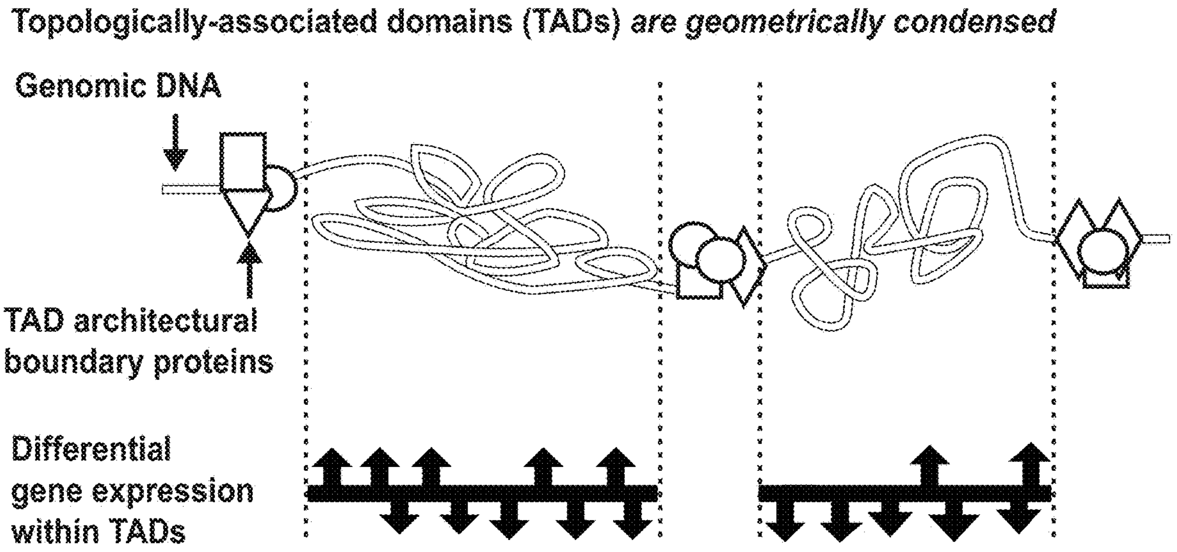
FIGS. 4A and 4B illustrates the nature of drug expansion of adjacent TADs working through activation of an enhancer and/or super enhancer results in differential gene expression.
Figure 4B:
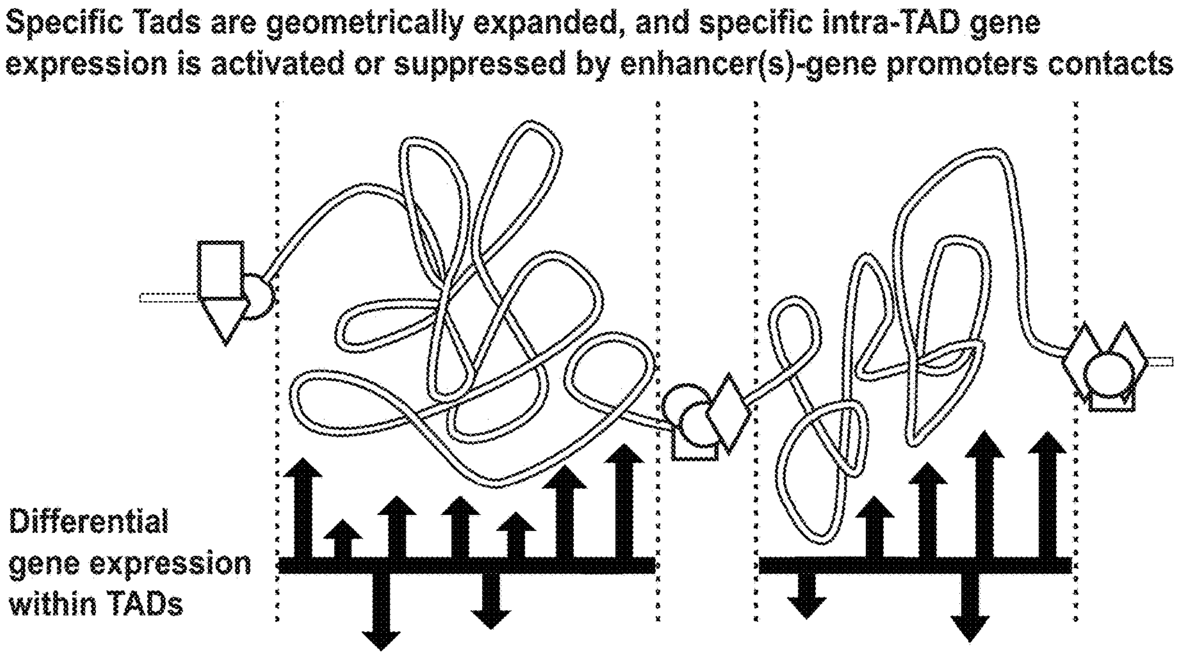
Figure 4C:
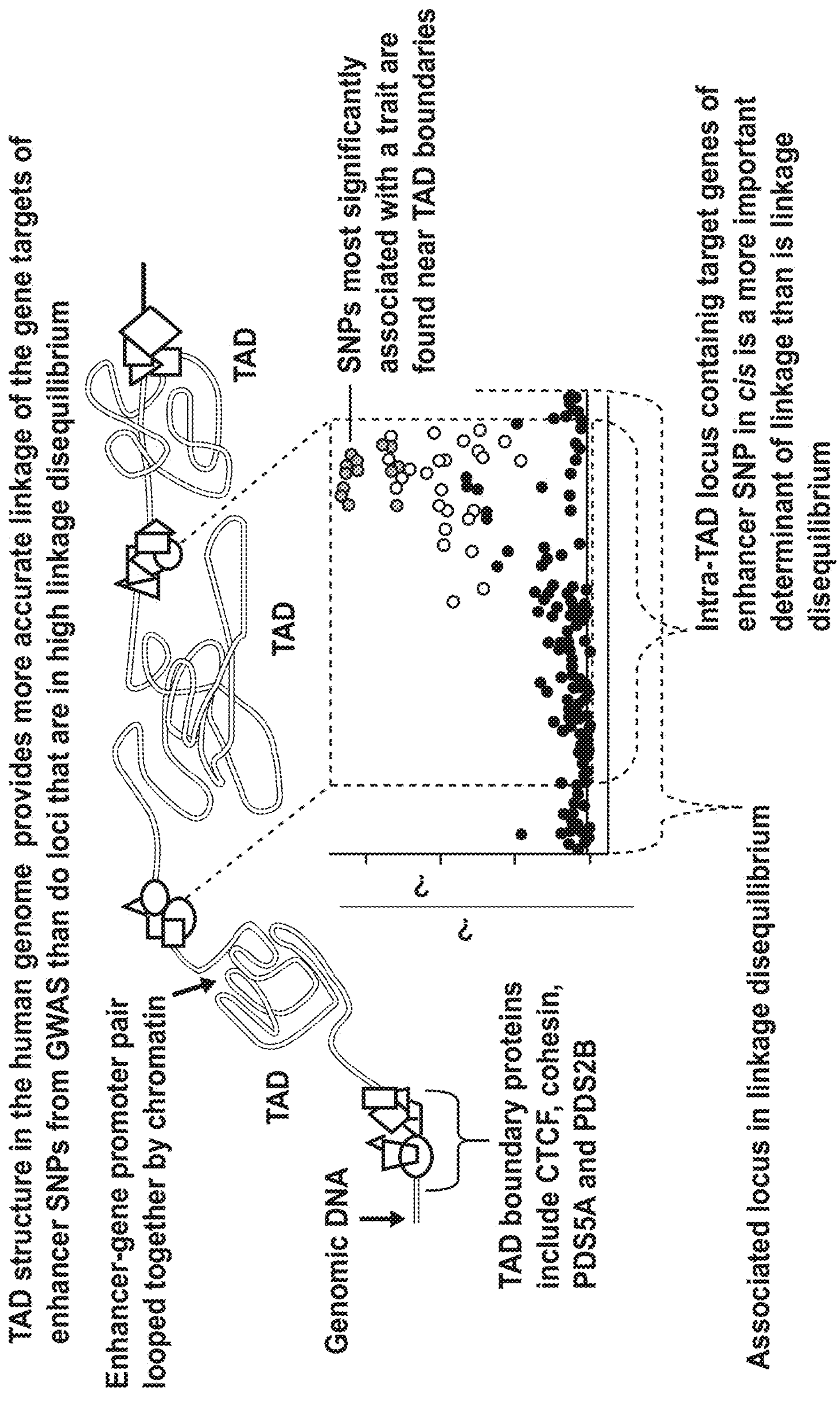
FIG. 4C illustrates that the TAD structure of the human genome provides more accurate information about the localization of the target genes of an enhancer and/or super enhancer than do traditional measures of linkage disequilibrium within human populations.

FIG. 4 illustrates the nature of drug effects on TADs regulated by super enhancers and TAD-based localization of causal SNP targets provides more accuracy than measures of linkage disequilibrium in human populations. FIG. 4A and FIG. 4B illustrates 2 adjacent TADs regulated by a super enhancer. In FIG. 4A with no drug present, the super enhancer is silent and differential gene expression within the adjacent TADs is minimal. FIG. 4B illustrates activation of a super enhancer controlling 2 adjacent TADs when a drug is present, causing geometric expansion of the TADs and concomitant increases in the expression of genes located within these expanded TADs. FIG. 4C illustrates that TAD organization in the spatial, regulatory genome provides a more accurate method to localize the gene promoter targets of causal enhancer SNPs from GWAS and other studies than those provided by traditional measures of linkage disequilibrium.

FIG. 5 shows that the human genome is organized in 3D similar to a "ball-of-yam." This three-dimensional organization changes in a dynamic manner over time, but regulatory interactions may be understood through examination of the position of TADs and their regulators the super enhancers, following drug-induced alterations.

At block 182, the drug pharmacogenomic network server 102 evaluates the candidate causal SNPs using a pharmacogenomics informatics pipeline. The pharmacogenomics informatics pipeline uses lead SNPs reported from GWAS, biobanks, PheWAS and other candidate gene studies to find genetically linked permissive candidate SNPs using TAD boundary instead of measures of linkage disequilibrium as shown in FIG. 4C. The enhancer regulatory SNP workflow evaluates the permissive candidate SNPs in disease-relevant tissues for DNA methylation, transcription factor binding, histone marks, DNase I hypersensitivity, chromatin state, quantitative trait loci (QTLs), chromatin loop-based contacts determined using techniques of chromosome conformation capture such as Hi-C, and transcription factor binding site disruption using tissue-specific omics datasets. As shown in FIG. 11, the drug pharmacogenomic network server 102 then evaluates the final output SNPs using open source machine learning algorithms to determine if the SNP is causal or not (block 183), and the causal variants are kept for further analysis in the workflow (block 184). Exon SNPs are also evaluated as splice donors or splice acceptors using the Altrans algorithm. If they found are to be involved in alternative splicing, they are stored as such.

Figure 9:
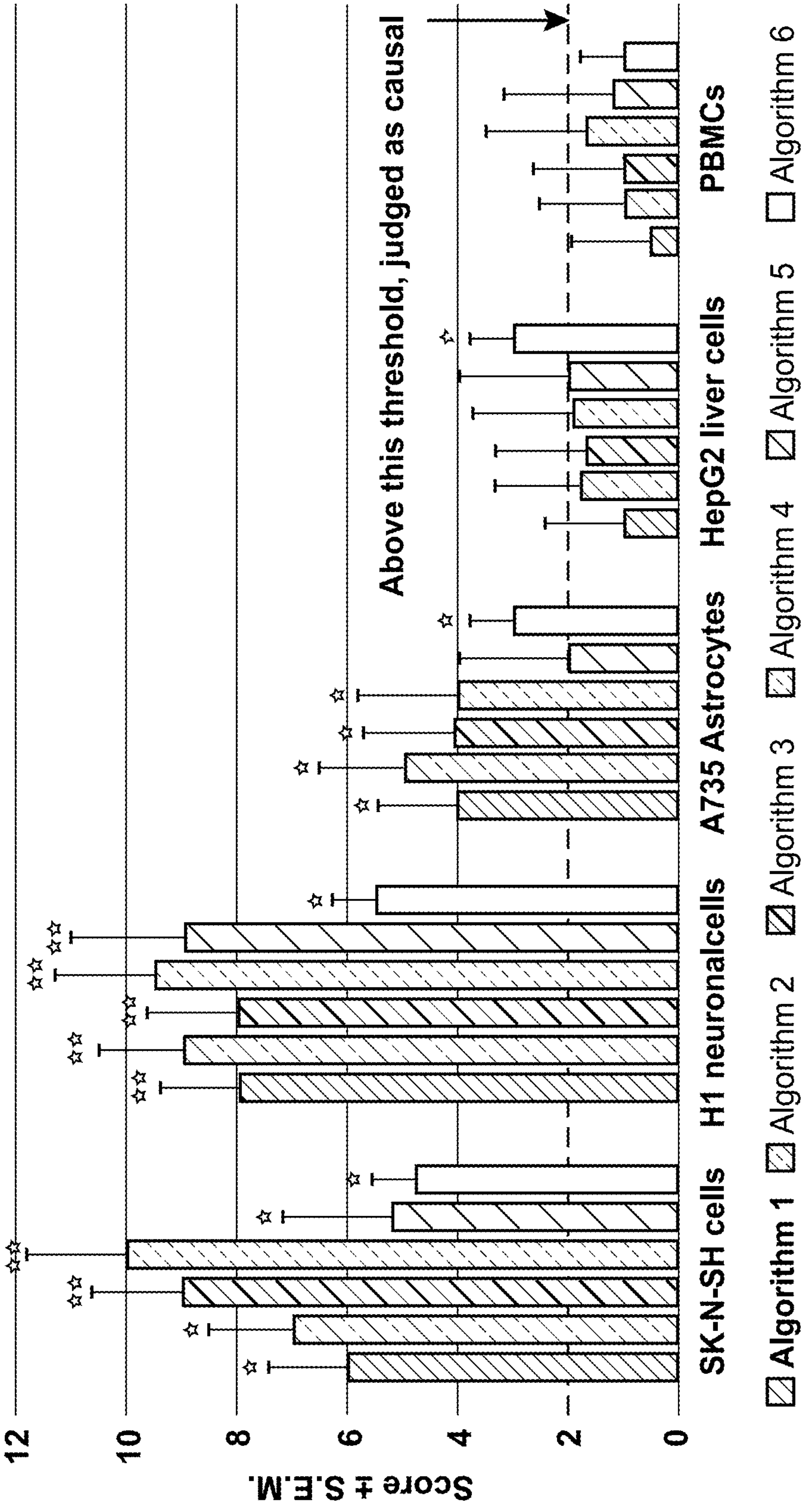
FIG. 9 illustrates an example of a comparison of the results of significance testing of the SNP rs12967143-G, an intragenic enhancer located in the TCF4 gene, versus other GWAS SNPs as described using the numerical output from six different machine learning algorithms used in the analysis and among various neural and non-neural cell types (*$p<0.05$; **$p<0.01$; ANOVA)

FIG. 9 illustrates an example of SNP selection for predicted causality using 6 different machine learning and deep learning algorithms based on tissue-specific distribution. This shows a candidate SNP, rs12967143-G, located within an intragenic enhancer located in the transcription factor 4 (TCF4) gene, versus other GWAS SNPs as described using the numerical output from the machine learning algorithms used in the analysis. *$p<0.05$; **$p<0.01$. Numerical scores from each algorithm are generated for each GWAS SNP and only in cases where each output scored the SNP as predicted to be causal in SK-N-SH cells and H1 cells, but not in HepG2 cells and PBMCs, were the SNPs retained for further analysis. The score of every predicted causal SNP was independently tested to determine if it differed significantly from the scores generated using 10 randomly selected GWAS SNPs for all human traits at $p<5E-08$ listed in the EBI-NHGRI GWAS catalogue using ANOVA. Only when the SNP met this criterion of significance, is it selected by the system for further analysis.

Use of Casual Enhancer SNPs for Interrogation of the Drug Pharmacogenomic Network At block 185, enhancer SNPs are used as probes to determine target genes as cis-interactions within the same TAD or adjacent TADs controlled by the same super enhancer, and to determine pharmacogenomic trans-interactions with other TADs using Hi-C chromosome conformation capture and ChIA-PET datasets to perform a mapping of 3D pharmacogenomic connections (block 187) generated from cell types and tissues in which the drug of interest acts. Genes, which herein includes other functional elements such as long non-coding RNAs, are located within the same TADs, or adjacent TADs controlled by the same super enhancer, or in trans-interactions, that are targets of the enhancer which significantly alters drug response in human populations are selected for the drug pharmacogenomic network, if the TADs involved in cis- and trans-interactions have strong boundaries as predicted by the amount of bound CTCF and/or significant association with super-enhancers (block 186). For trans-interactions, if the TADs including adjacent TADs controlled by the same super enhancer, which comprise the top 3 statistically significant pharmacogenomic contacts of the first set of pharmacogenomic TADs within the same cell and/or tissue type in which the drug of interest acts are then evaluated, and genes within these "trans-TADs" are chosen if they are controlled by the same cell and/or tissue-specific enhancers in which the drug of interest acts (block 188).

Figure 7:
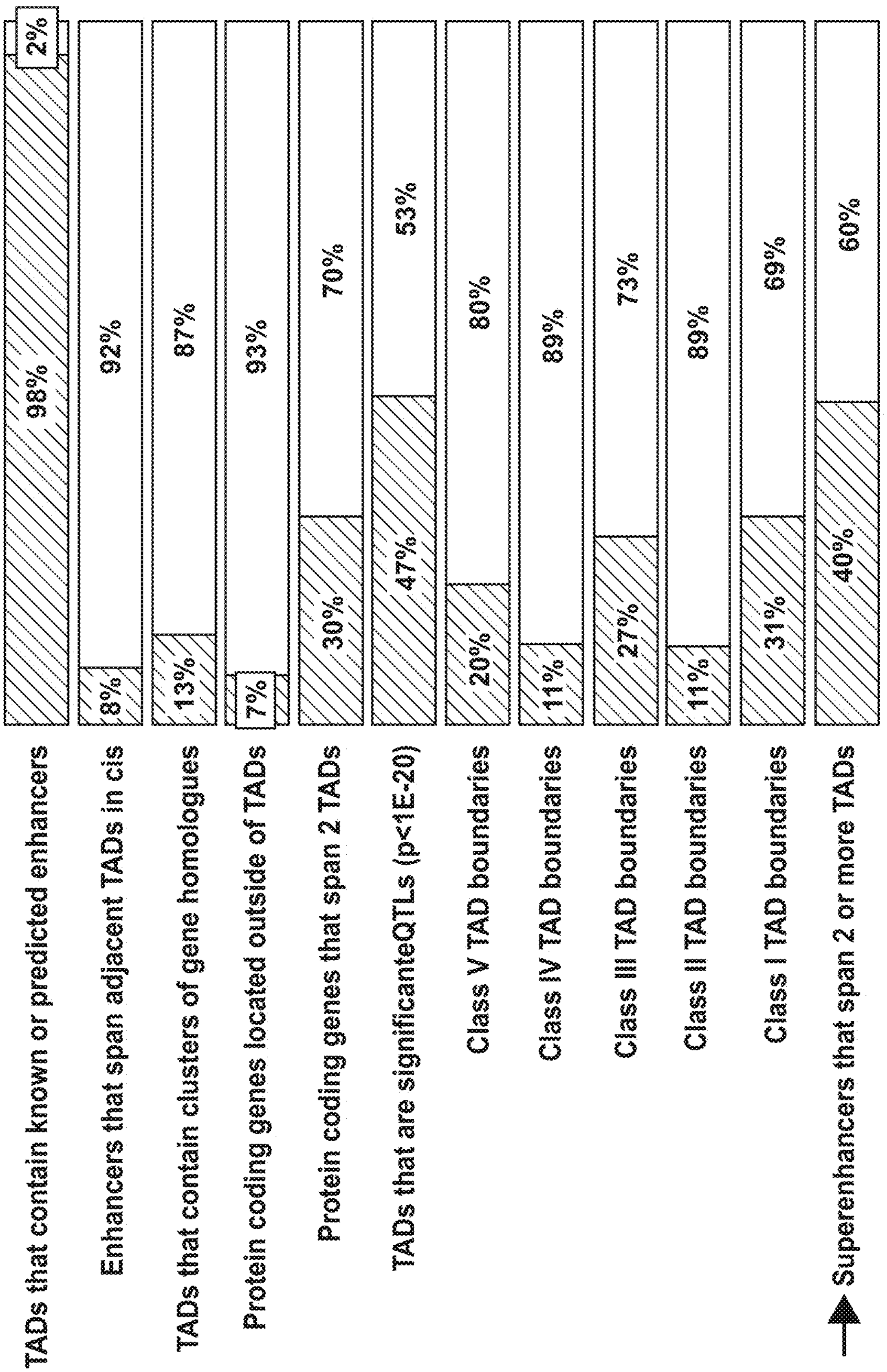
FIG. 7 illustrates characteristics of the spatial genome, including several enhancers in each TAD located within non-coding genomic DNA (i.e., intergenic or intronic) that selectively activate or repress specific functionally related genes within that TAD.

FIG. 7 illustrates the distribution of TAD characteristics in one cell type in the human genome. 98% of TADs contain known or predicted enhancers and 40% of TADs have known super enhancers that span adjacent TADs in the genome.

At block 189, the drug pharmacogenomic network server 102 evaluates the combined set of genes for inter-connectivity, where the combined set of genes are selected from the first set of TADs which harbor the pharmacogenomic SNPs and the genes selected from the "trans-TADs", comprising the genes controlled in concert with the first set of cis-interacting genes. For example, the drug pharmacogenomic network server 102 may utilize third-party software such as Ingenuity Pathway Analysis™ for examination of connectivity of the combined set of genes. Using Fisher's right-sided exact test, if the drug pharmacogenomic network server 102 determines there exists significant interconnectivity within the combined set of genes based on the published literature, then the genes are placed into the preliminary set of genes that comprise the pharmacogenomic network for the drug of interest. Any genes not forming a connected network are discarded as non-candidate genes for the pharmacogenomic network (block 190).

Knowledge-Based Revision Using the Drug Pharmacogenomic Network Bandwidth Adjustor Then at block 191, manual, semi-automated or automated curation, or a combination thereof, is performed on each gene in this gene set comprising the preliminary drug pharmacogenomic network to remove genes whose function is not related to the drug of interest in the cell and/or tissue types in which it acts, or to add other genes not part of this preliminary set of the drug pharmacogenomic network should be added to the set if they judged to be specifically impacted by the drug of interest in the cell and/or tissue types in which it acts. The interrogation steps include definition of an individual gene's function, the phenotypic consequences of mutational impairment of the gene, and the human cells and tissues in which the gene is expressed, to see if it can become a candidate for membership in the pharmacogenomics network of the specific drug of interest.

In one embodiment, these determinations can be made using a manual and semi-automated strategy, combining manual curation of each gene, its mutational profile, and its localization of expression within human tissues. These are enabled by a variety of web-based search tools, including gene definitions, genome browser annotations, the GWAS catalogue and other bioinformatics resources. For example, the drug pharmacogenomic network server 102 may invoke application programming interfaces (APIs) having executables written in R, Python, PERL or other programing languages to facilitate data access, data cleansing and data analysis. This embodiment is an enhanced model of manual curation but can become time limiting if there are many genes within a gene set of the drug pharmacogenomic networks or the gene subsets of the sub-networks, and especially in cases where functional genomic elements may include regulatory RNAs or functional RNAs such as long noncoding RNAs, or if the function of the genes are poorly understood. Listing and analysis of the mutational landscape of a given gene (+10 Kb upstream and downstream) is the easiest of the 3 interrogation steps to be performed because these databases are the most comprehensive. Other resources exist for the analysis of the tissue distribution of a gene's expression pattern. In cases where these patterns are compared to sites where the specific drug of interest acts, the pharmacogenomic network identification system 100 may leverage the results from imaging modalities including from radiological studies, light microscopic analysis in pathology and even more sophisticated methods. In some embodiments, the drug pharmacogenomic network server 102 performs this analysis using machine learning techniques, such as neural networks.

In another embodiment, the drug pharmacogenomic network server 102 may use a Bayesian probabilistic classifier, either based on machine learning or using Bayesian probabilistic computing. The automated methods can be used to reduce the complexity of data analyzed from disparate data resources in which a gene's function knowledge profile, its mutational landscape and its tissue expression mapping are inputs to a learning machine that has been trained on a number of such instances and tested independently on another set of instances for determination of accuracy. Predictive features selected by the trained neural network can be implemented on a support vector machine classifier to construct a gene's function and mutational prediction model, where subsequent machine states determine the adequacy of statistical fit to the drug pharmacogenomic network.

In some scenarios, machine learning is subject to over-fitting, outputting false positives or false negatives. In another embodiment, the drug pharmacogenomic network server 102 may perform semi-automated and naïve Bayesian classification using machine learning in parallel to sharpen the accuracy of the final output.

The drug pharmacogenomic network server 102 and more specifically, the drug pharmacogenomic network bandwidth adjustor 146B may perform the knowledge-based curation with the following steps. First, the drug pharmacogenomic network server 102 examines the gene definition from multiple databases to understand if it is specifically, but not generically, impacted by the drug of interest. In addition, the published literature, including text word strings containing the gene name or precursor gene name or equivalent protein name plus any function related to the drug of interest is evaluated following thorough internet searches using for example, Google Scholarm and/or PubMed. These may include binding affinity studies which have reproducibly found molecules which bind with an affinity that is within 10-fold that of the affinity of which the drug of interest binds to the same pharmacodynamic target. Second, the drug pharmacogenomic network server 102 examines each gene for all mutations, including SNPs, variable number of tandem repeats, duplications and all other known mutational alterations, extending in linear sequence+10 kb from the transcription start site(s) and stop codon(s) of the gene as examined in a genome browser such as the UCSC genome browser or the Ensembl genome browser. If any of these mutations are found in either the published literature or sources such as unpublished clinical trial data, and they are involved in the action of the drug of interest, including efficacy, adverse events or first pass metabolism, then they are added to the preliminary set of genes comprising the pharmacogenomic network (block 192). Third, especially for complex tissues such as the brain, skin and the cardiovascular system, the drug pharmacogenomic network server 102 performs concordance mapping qualitatively to compare the expression of all genes in this final set to where the drug of interest exerts its action, if known. Genes whose expression does not match the pharmacodynamic substrate of the drug of interest are discarded (block 192). Finally, third-party software such as Ingenuity Pathway Analysis™ is used for examination of connectivity of this gene set (block 193). Using Fisher's right-sided exact test, if the drug pharmacogenomic network server 102 determines there exists significant interconnectivity based on the published literature, then they are placed into the preliminary set of genes that comprise the pharmacogenomic network for the drug of interest. Any genes not forming a connected network are discarded as non-candidate genes for the pharmacogenomic network (block 194).

Figure 38:
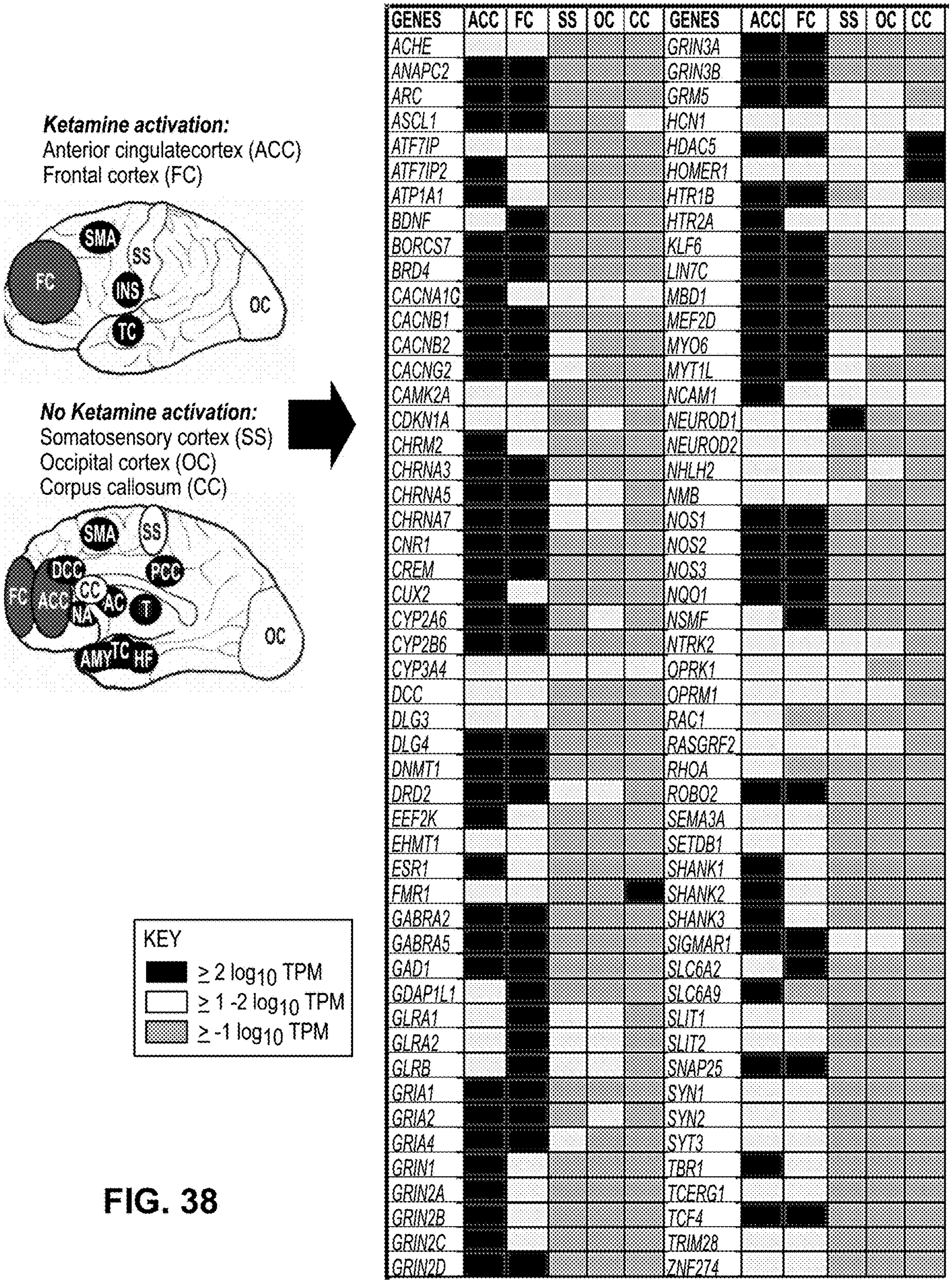
FIG. 38 illustrates the significant overlap between the neuroanatomical distribution of gene expression data within the ketamine pharmacogenomic network with the localization results from a consensus brain-map showing which brain regions are first impacted by ketamine obtained from 24 neuroimaging studies.

The drug pharmacogenomic network server 102 may perform the knowledge-based curation using gene expression patterns where overlap suggests functional correspondence. Such an example is shown in FIG. 38, which may exist where the genes of the ketamine pharmacogenomic network exhibit statistically significant overlap (P<1E-56; Fisher's exact test) where the drug exerts its rapid action in the human brain, including anterior cingulate cortex (ACC) and frontal cortex (FC), but no overlap in somatosensory cortex (SSC), occipital cortex (OC) or the corpus callosum (CC).

The Drug Pharmacogenomic Network Reconstruction Engine

Figure 6B:
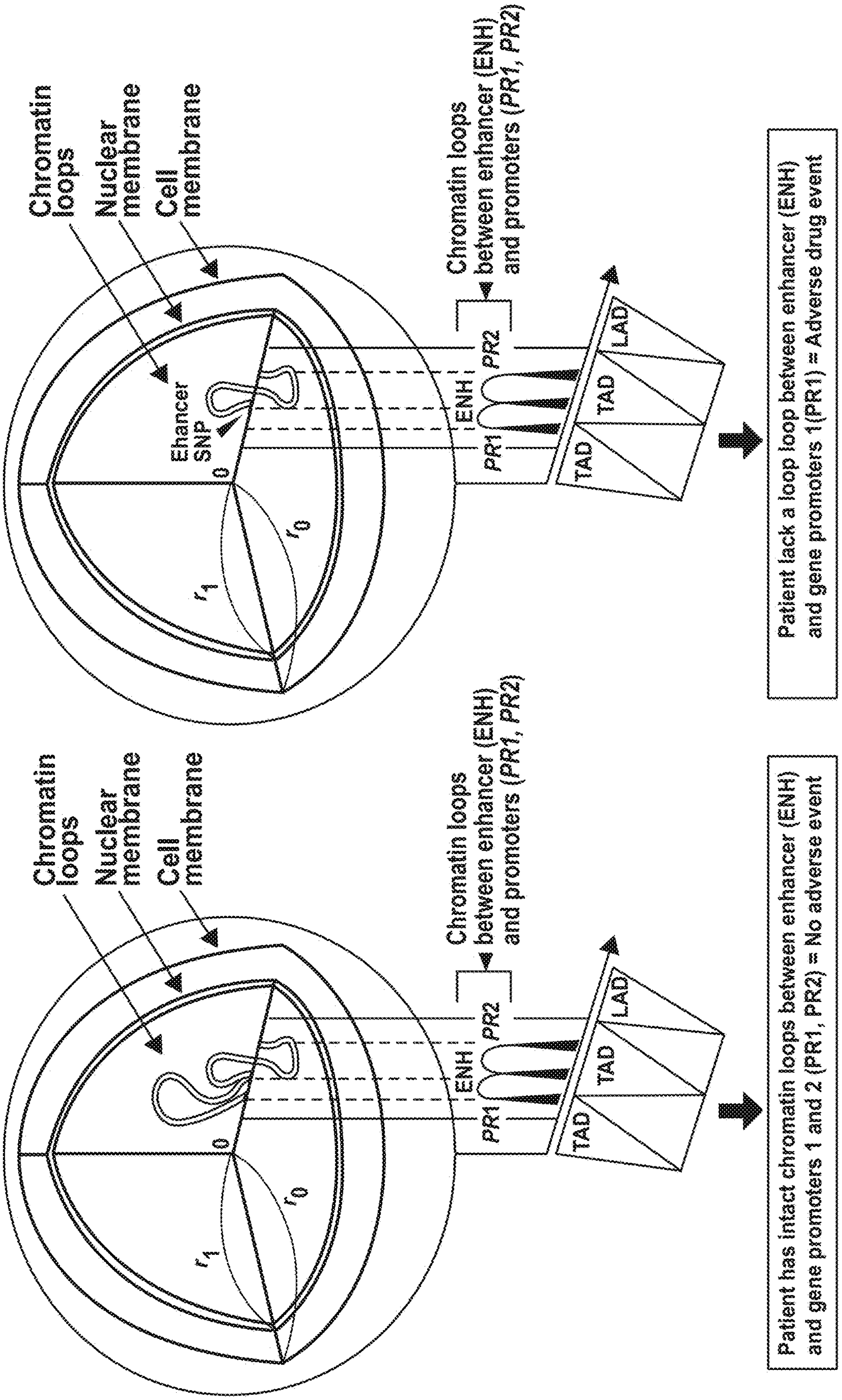

FIG. 11 shows the composition of the drug pharmacogenomic network reconstruction engine 146A that uses proprietary and public knowledge of the 3D human genome, previously defined TADs, super enhancers and other characteristics of the regulatory genome as provided in a spreadsheet look-up table for either the original version in human genome build 19 (hg19) or the more recent sparse human genome build 38 (hg38). This is a key component of the network reconstruction engine 146A. All experimental data generated from chromosome conformation capture methods undergoes evaluation, where the chromosome conformation capture methods may be performed in vivo, generated from causal SNP probing of chromatin datasets in cell types in which the drug of interest is active as shown in FIG. 22 and FIG. 33, or from public sources or other private sources. A parsimonious model of drug-induced alterations in the 3D regulatory genome including TAD matrices, enhancer-promoter pairs, promoter-promoter pairs, and super enhancers is developed in either 2D or 3D using the SNPs or candidate variants identified above based on a chosen method such as the method illustrated in FIG. 6, including 3D modeling of human genome architecture in Euclidian space, high resolution light microscopy using FISH, and/or a combination of measures of gene expression (e.g., RNA sequencing, promoter capture Hi-C). Following evaluation of the drug's pharmacogenomic interactome in chromatin, the resulting pharmacogenomic network is defined in a preliminary manner. To determine whether network elements are significantly inter-connected based on existing biomedical knowledge, third party pathway analysis software is used to provide a significance score. Commonly used programs used in gene pathway analysis include Ingenuity Pathway Analysisrm, Panther Gene Ontology pathway mapping and KEGG (Kyoto Encyclopedia of Genes and Genomes). In this manner, the network reconstruction engine 146A determines interconnections between SNPs and target genes correlated with drug response or adverse events for the particular drug of interest.

The Iterative Gene Set Optimization Engine

Figure 12:
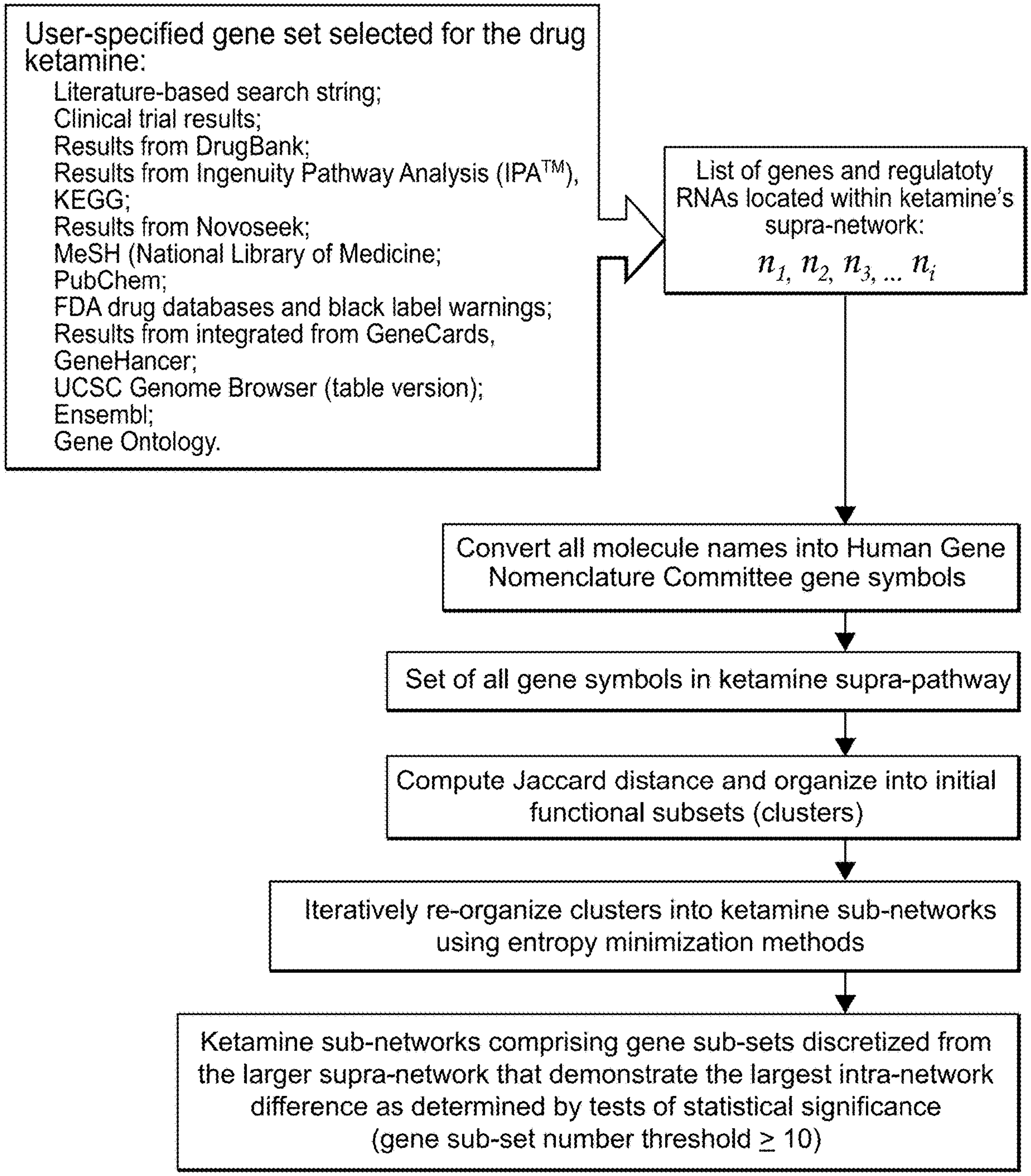
FIG. 12 illustrates a flow diagram representing an exemplary method for iterative gene set optimization to deconstruct a drug pharmacogenomic network into sub-networks.

At block 195, the drug pharmacogenomic network server 102 and more specifically, the gene set optimization engine 146C performs iterative gene set optimization on the identified set of candidate genes in the pharmacogenomic network for the particular drug of interest. An example method for iterative gene set optimization to deconstruct a drug pharmacogenomic network into sub-networks is illustrated in the flow diagram of FIG. 12. Iterative gene set optimization may be performed to identify sub-networks of the pharmacogenomic network. More specifically, iterative gene set optimization includes converting all input molecule terms into gene or long non-coding RNA names from for example, the Human Gene Nomenclature Committee (HGNC) names using their API. The iterative gene set optimization differs from gene set enrichment methods, by not only combining a variety of statistical methods, but also not acting in a hierarchal manner ranking genes as in threshold-dependent methods, and iterative gene set optimization does not rely on comparisons of experimental results, such as in whole-distribution tests. Instead, the iterative gene set optimization groups genes or long noncoding RNAs using the Jaccard distance to first measure the similarity between two genes or long noncoding RNAs based on the dissimilarity of user-selected terms, where the Jaccard distance is as the ratio of the size of the symmetric difference Gene A Δ Gene B=$A \cap B - A \cup B$ to the union. This is extensible into clusters of related dissimilar gene names. The drug pharmacogenomic network server 102 then automatically sorts these sets, or using user-defined numbers of clusters, into subsets of clustered subsets of functionally related genes using a minimal entropy sorting algorithm, such as the COOLCAT algorithm. Following gene subset optimization using entropy minimization, the drug pharmacogenomic network identification system 100 may employ manual curation to assign efficacy, adverse event or functional mechanistic sub-networks based on known attributes of the drug's mechanism of actions under consideration.

Post-Hoc Validation Using Third Party Bioinformatics Tools

Figure 13:
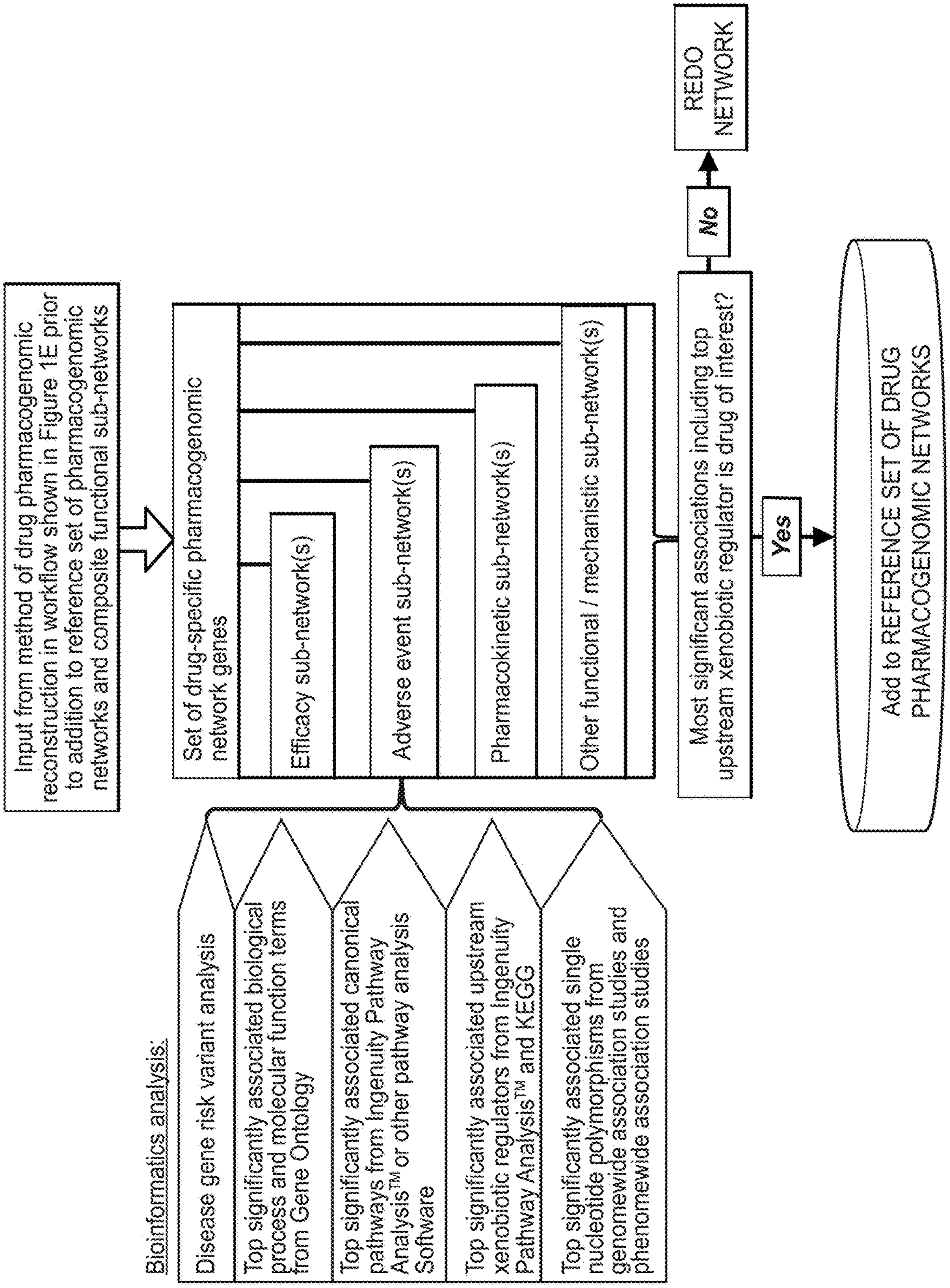
FIG. 13 illustrates a flow diagram representing an exemplary method for post hoc validation of drug pharmacogenomic networks and their constituent sub-networks using a standardized bioinformatics analysis.

For scientific validation of the deconstruction of the drug pharmacogenomic network into mechanistic sub-networks based on functional gene subset optimization, the drug pharmacogenomic network server 102 assesses each drug pharmacogenomic network's sub-networks post hoc for top Gene Ontology terms (molecular function and biological processes), top terms from a medications database, top canonical pathways for example, as determined using other proprietary or open source pathway analysis software, disease risk gene variant analysis for example, as determined using other proprietary or open source pathway analysis software, and determination of upstream xenobiotic regulators using different bioinformatics resources (block 196). The upstream xenobiotic regulators are compared to the particular drug of interest to ensure that the particular drug of interest is the most significantly associated drug to the drug pharmacogenomic network. More specifically, the upstream xenobiotic regulators may be ranked according to their respective associations to the drug pharmacogenomic network using the different bioinformatics resources. For example, the upstream xenobiotic regulator having the lowest p-value with respect to the drug pharmacogenomic network may have the strongest association. Then the drug pharmacogenomic network server 102 may determine whether the particular drug of interest is the top ranked upstream xenobiotic regular or is ranked above a threshold ranking (e.g., ranked in the top three or ranked in the top five). In addition, the GWAS catalogue of the European Bioinformatics Institute, the National Human Genome Research Institute, and the National Institutes of Health may be searched to find significant SNP-trait associations for each gene of the gene sets for each sub-network. By providing examples of SNPs from GWAS that are statistically significant, additional evidence may be provided that mutational impairment of the genes included in each sub-network provides insight into the normal, unimpaired function of the sub-network. An example method for performing post hoc validation of pharmacogenomic networks and their constituent sub-networks is illustrated in the flow diagram of FIG. 13.

In some embodiments, after post hoc validation is performed, the resulting pharmacogenomic network and constituent sub-networks for the particular drug of interest are stored, for example, in the database 154 as shown in FIG. 1A. In some embodiments, the drug pharmacogenomic network server 102 may provide an indication of the pharmacogenomic network and constituent sub-networks to the client device 106-116 for display to a health care professional or researcher. The client device 106-116 may then present the pharmacogenomic network and constituent sub-networks in a graphical display.

Error Correction of the Drug Pharmacogenomic Network and Sub-Networks

In some embodiments, the drug pharmacogenomic network server 102 may adjust or tune the pharmacogenomic network and constituent sub-networks for a particular drug to provide an accurate model for measuring human drug response phenotypes for use in real world clinical applications. From studies of population structure using principal component analysis, allele-sharing distance and other measures, it has been presumed that distribution of pharmacogenomic phenotypes can be modeled using a normal distribution, albeit with some outliers. For example, previously it was thought that cytochrome P450 gene variation, producing differences in CYP450 isoform activity was the primary major determinant of the variability of drug response among humans.

One embodiment of this disclosure comprises SNPs within enhancer networks that regulate PK gene expression as well as other genes located within the same TADs. In a drug and patient-dependent context, variation within these networks impact tissue-specific metabolism which extends beyond missense codons. For patients in which the TAD boundaries of PK genes may be compromised as shown in the example of PK genes, the trans-interactions of enhancers which are less constrained to the TADs in which they are located may result in adverse drug events.

FIG. 10 shows that drug metabolizing genes, and human leukocyte antigen (HLA) genes that are involved in immune-related adverse drug responses, have strong boundaries. Of the 13 gene clusters shown here, 12 have the strongest TAD boundaries (class V) in the human genome. These include most of the genes that encode the cytochrome P450 enzymes (CYP genes), genes of the glucuronosyltransferase (UGT) superfamily, genes of the sulfotransferase (SULT) superfamily, genes of the N-acetyltransferase (NAT) family, and HLA genes. Mutations such as SNPs that are located in the TAD boundaries of these genes have deleterious effects on drug metabolism and drug response variation including the occurrence of adverse drug events in human populations.

It is also recognized that additional variables play a role in human drug response, including the impact of sociological status and other environment factors, which are often difficult variables to measure.

Figure 17A:
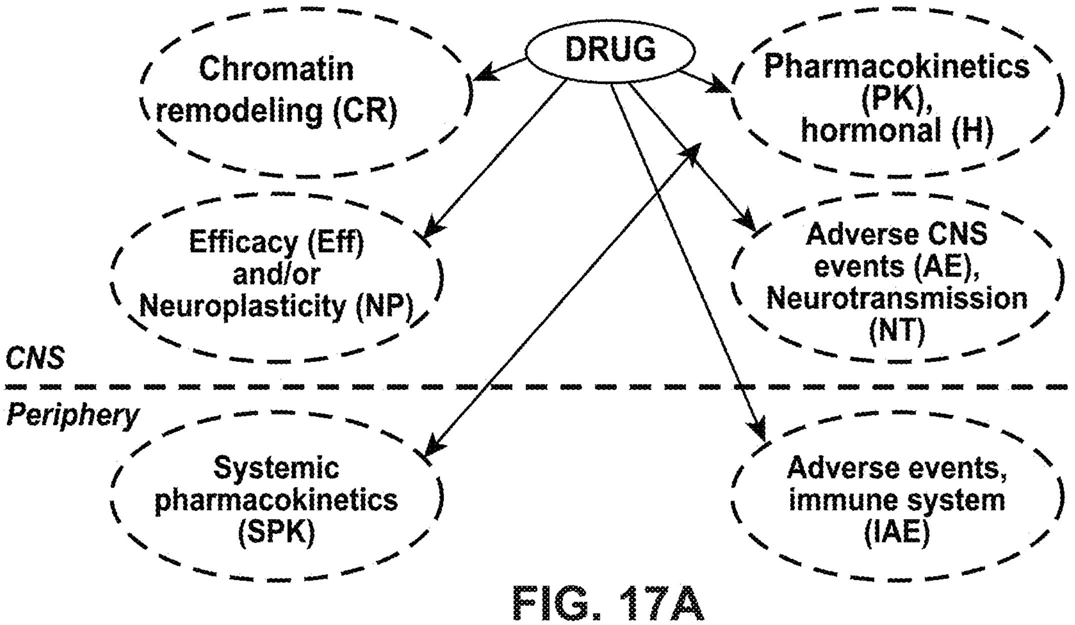
FIG. 17A illustrates the general topological model for CNS and Peripheral drug response, including chromatin remodeling, PK/Hormonal modulation, Efficacy, Adverse Event (AE), systemic PK, and systemic AE and immune systems response.
Figure 17B:
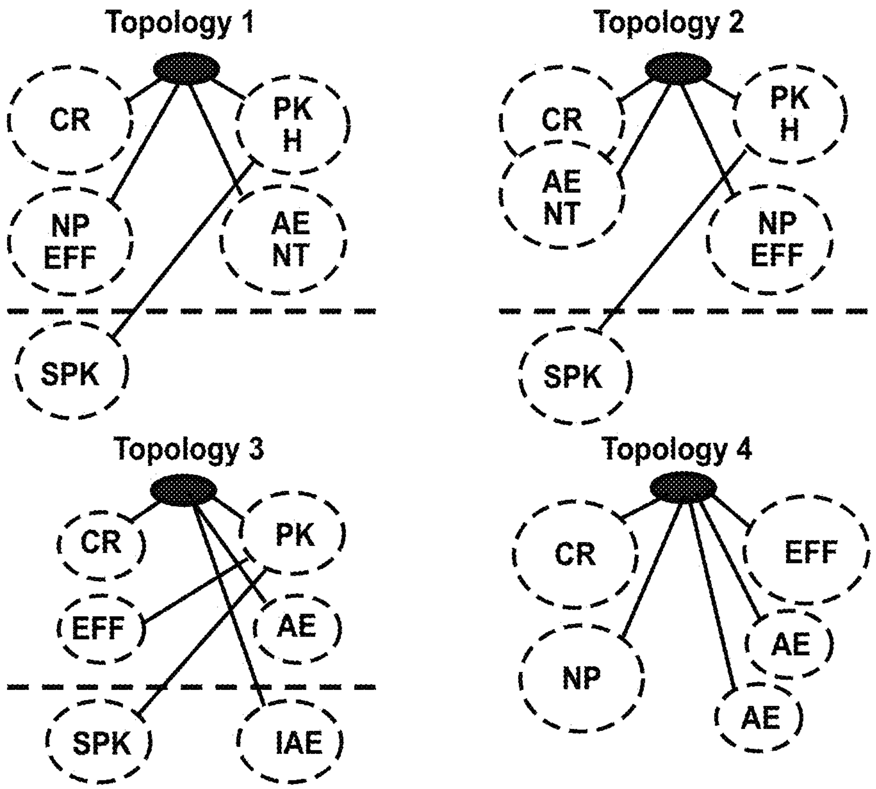
FIG. 17B shows an exemplary set of four pharmacogenomic network topology models and their constituent sub-networks that define the psychotropic and antineoplastic drug response, and example medications that conform to those topologies. These topologies are used by the system described herein.

FIG. 17 illustrates the pharmacogenomic network topology that may be used by the system as a model of the action of the majority of psychotropic drugs. In FIG. 17A, the template model of the central nervous system (CNS) includes the drug, and boxes that include: (1) chromatin remodeling, (2) efficacy (EFF) and/or neuroplasticity (NP), (3) Adverse CNS events (AE), and (4) centrally-active pharmacokinetic enzymes (PK) and hormones (H). For some drugs, systemic pharmacokinetics (SPK) are primary determinants of human drug response variation, and peripheral adverse drug events involving the immune system (IAE) are problematic. In FIG. 17B, different pharmacogenomic network topologies are shown for psychotropic drugs with examples of the different biological profiles that fit the different two-dimensional topologies. Accordingly, drug pharmacogenomic networks may be deconstructed into constituent sub-networks using the topology of sub-network types shown in FIG. 17, where the sub-network types for the majority of psychotropic drugs may include two or more of: (1) chromatin remodeling, (2) efficacy (EFF) and/or neuroplasticity (NP), (3) Adverse CNS events (AE), (4) centrally-active pharmacokinetic enzymes (PK) and hormones (H), (5) systemic pharmacokinetics (SPK), and (6) peripheral adverse drug events involving the immune system (IAE).

Figure 14:
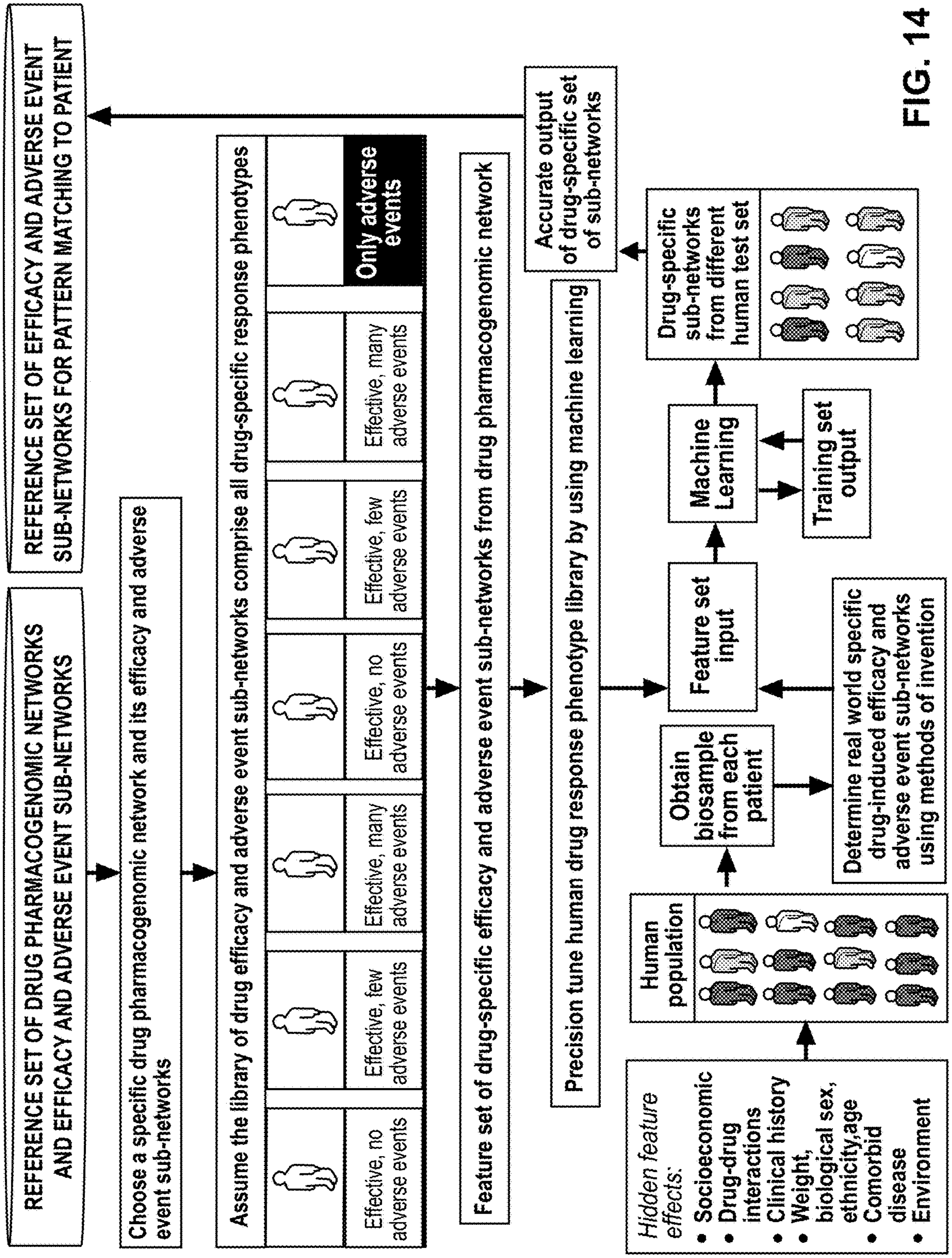
FIG. 14 illustrates a flow diagram representing an exemplary method for error correction of the drug pharmacogenomic networks and their constituent efficacy and adverse event sub-networks leveraging individualized patient response data.

FIG. 14 illustrates a machine learning-based method 600 by which computationally predicted efficacy and adverse event sub-network measures of a drug pharmacogenomic network are tuned in human populations, including a training set and a test set, to obtain an accurate discretization of response phenotype. In some embodiments, the drug pharmacogenomic network server 102 executes the method 600 illustrated in FIG. 14. Also, in some embodiments, the method 600 may be implemented in a set of instructions stored on a non-transitory computer-readable memory and executable on one or more processors on the drug pharmacogenomic network server 102. In any event, the method 600 increases the accuracy of the presumed distribution of human response phenotypes for a specific drug that has been developed from computational analysis through training such drug-specific sub-networks using the drug pharmacogenomic network identification system 100, where the human drug response phenotypes are derived from efficacy and adverse event sub-networks. In this manner, the drug pharmacogenomic network server 102 improves the utility of the distribution of human response phenotypes for use in real world clinical applications, making them useful for any reference-based comparative measures to be performed in medicine or the life sciences.

Matching a Reference Drug's Pharmacogenomic Network to a Patient

The learning architecture for training the pattern matching sub-networks includes pre-training the reference set (ref. no. 710) as illustrated in FIG. 15. This is further described with reference to the method 700 illustrated in FIG. 15 which may also be executed by the drug pharmacogenomic network server 102. More specifically, at block 704, the drug pharmacogenomic network server 102 develops the patient's pattern matching sub-networks derived from the patient input biosample, and co-develops separate trained pattern metrics (block 712), which contain the features of the efficacy and adverse event sub-networks, to a joint feature representation metric. For determination of similarity to the reference set (blocks 706, 708), the two different pairs of reference-patient metrics include an accurate measurement of similarity and outputs similarity scores for each of the efficacy and adverse events (blocks 714, 716). At block 702, the biosample obtained from a patient, which may be a cheek swab, blood or urine sample, undergoes targeted enhancer SNP genotyping, as well as combined chromosome conformation capture and RNA-seq. Then at block 704, the drug pharmacogenomic network server 102 performs analysis necessary to build the input patient-specific map of efficacy and adverse event sub-networks for a specific drug of interest. These patient-specific, drug-induced sub-network patterns could be further processed using Bayesian probabilistic computing to fill in sparse or missing data. As a new patient enters as an input, the pretrained reference set of drug-specific efficacy and adverse event sub-networks for pattern matching is once again optimized for subsequent patients, producing a more accurate measure of pharmacogenomic variability among humans with enhanced clinical utility. This matching task assumes that patches go through the same feature encoding before computing and outputting a similarity score, greatly increasing efficiency while reducing computational requirements.

Each set of inputs (reference set (ref. no. 710) and patient set (ref. no. 720)) are thus constructed differently with feature set extraction and inference of sparse data using probabilistic computing based on Bayesian distribution to increase the accuracy of reference and patient maps. The trained feature network is based on a "Siamese" network approach, with the constraint that the two sets must share the same parameters. When completed, the patient's drug-induced trained pattern networks are coupled with that obtained from the reference database, pairing efficacy feature set pairs and adverse event feature set pairs. These provide the basis for the development of a trained efficacy metric and a trained adverse event metric that attempt to match all the features from the patient and the reference set for the drug of interest. These pairwise matching scores yield separate efficacy and adverse event similarity scores between reference and patient.

A further elaboration of this embodiment is to develop a reference pattern matching set for each patient, that could be used to create a patient-specific database of such reference maps, and updated in a periodic manner as additional biosamples are obtained from the patient in a longitudinal manner, obtained in a clinical setting or outpatient pharmacy over time.

Method of in Silico Drug Target Identification

Figure 16A:
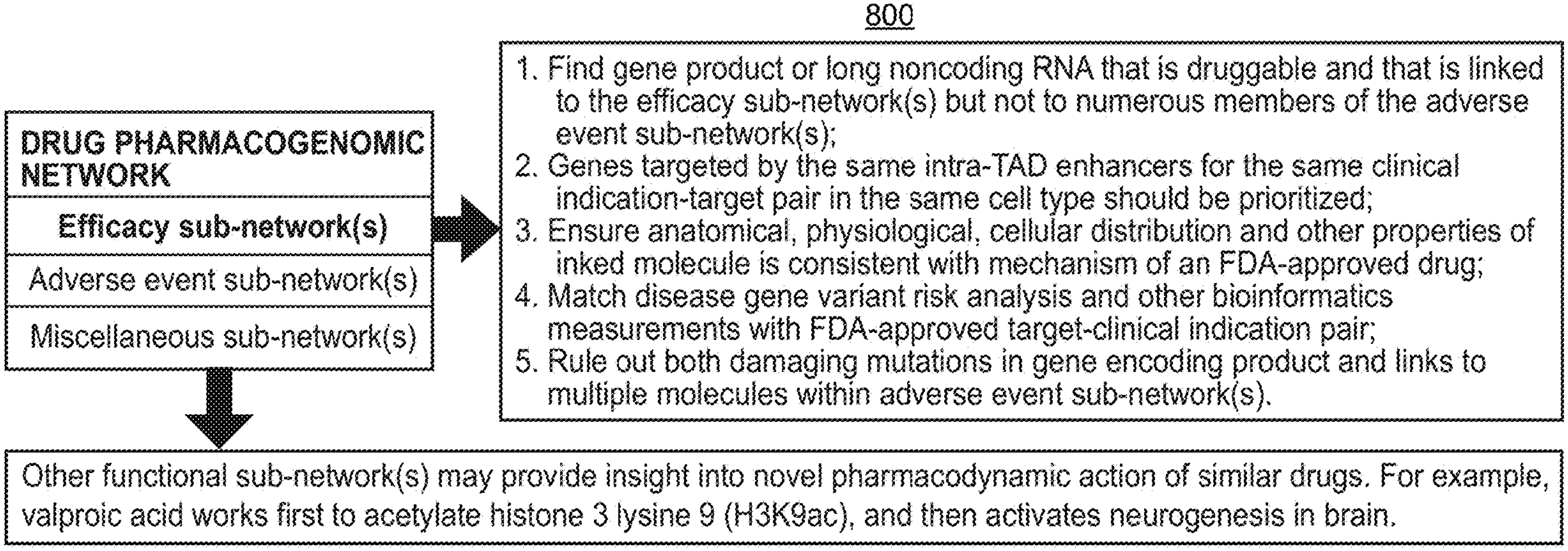
FIG. 16A illustrates a flow diagram representing an exemplary method of in silico drug target identification and drug repurposing for the druggable target PPP1R1B.
Figure 16B:
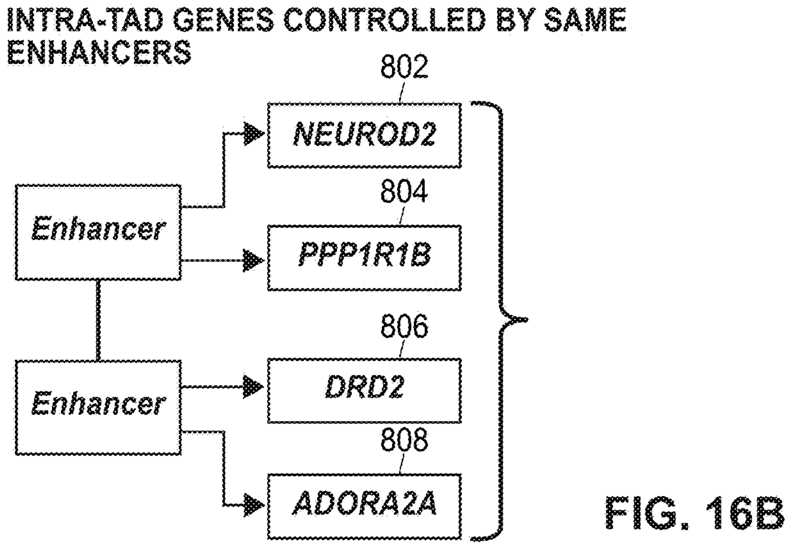
FIGS. 16B and 16C also show an illustration of some the characteristics of the druggable target PPP1R1B within the neuronal development and antidepressant mechanistic sub-network 2 of the ketamine spatial network illustrates traits of the ketamine pharmacogenomic network as determined from a post hoc validation of the ketamine pharmacogenomic network and its efficacy and adverse event sub-networks.

FIG. 16A and FIG. 16B illustrate another method 800 utilizing the pharmacogenomics network and efficacy and adverse event sub-networks for a particular drug of interest to develop a molecule as a druggable pharmacodynamic target. In some embodiments, the drug pharmacogenomic network server 102 executes the method 800 illustrated in FIG. 16A. Also in some embodiments, the method 800 may be implemented in a set of instructions stored on a non-transitory computer-readable memory and executable on one or more processors on the drug pharmacogenomic network server 102.

Figure 16C:
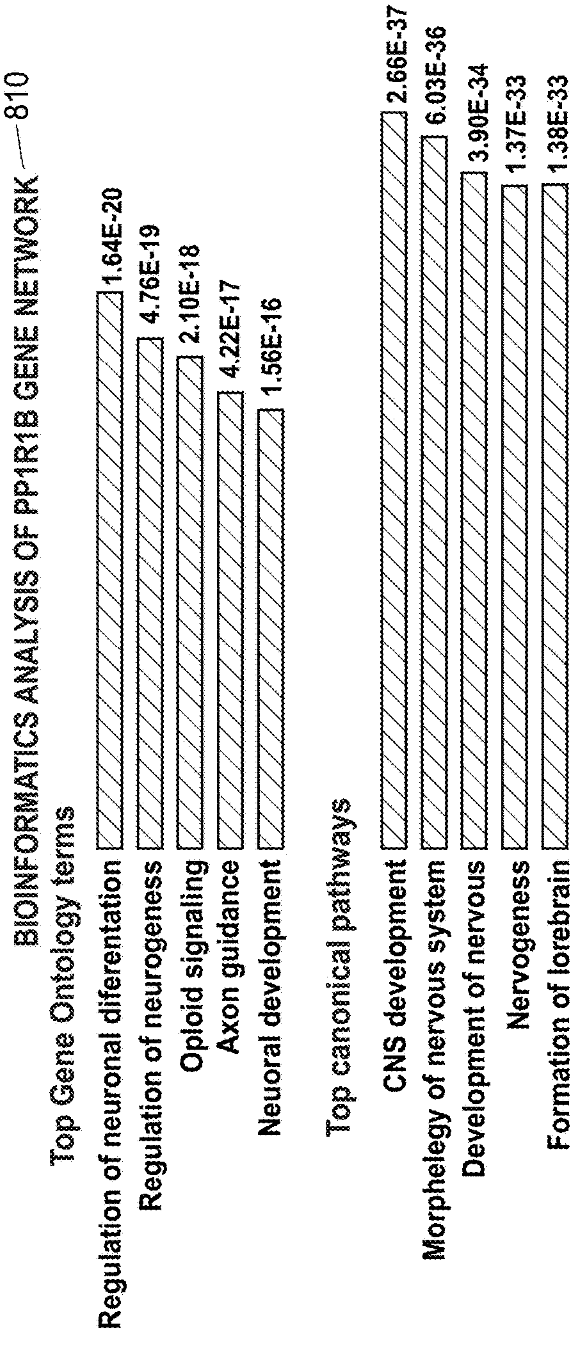
Figure 16D:
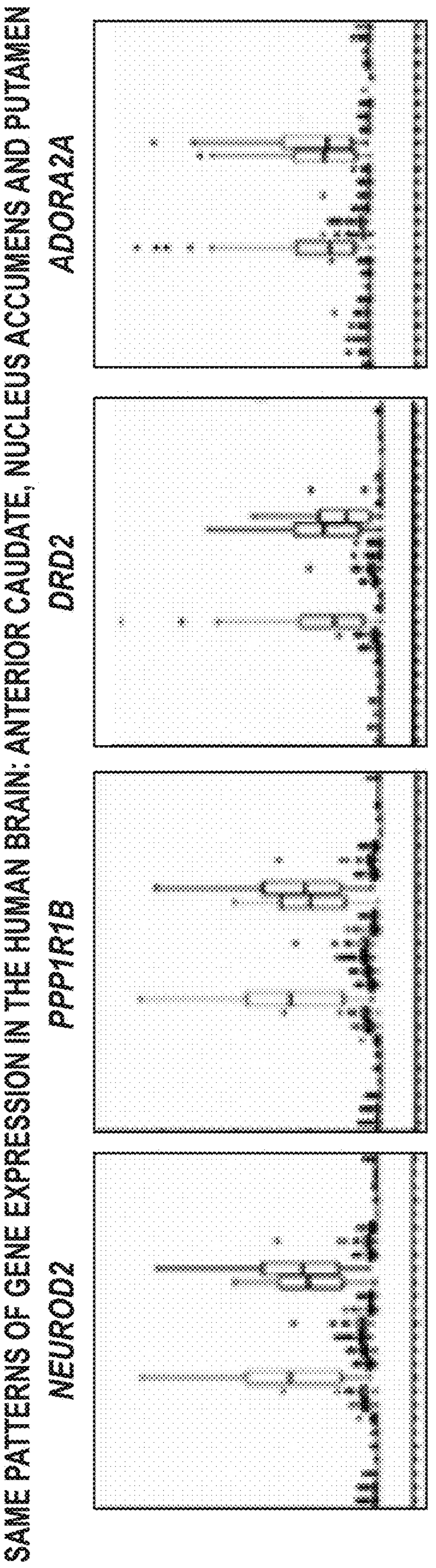
FIG. 16D illustrates gene expression data for key pharmacogenomic efficacy genes in relevant brain tissue regions.

In any event, a previously unrecognized gene that encodes a druggable pharmacodynamic target may be linked to the efficacy sub-network of a particular drug's pharmacogenomic network, with minimal connectivity with multiple genes in the adverse event sub-network of the particular drug's pharmacogenomic network at the pharmacogenomic regulatory level. In the example illustrated in FIGS. 16A and 16B, the ketamine pharmacogenomic network is used, and the druggable target is PPP1R1B (Protein Phosphatase 1 Regulatory Inhibitor Subunit 1B) (ref. no. 804), a bi-directional signal transduction molecule that is regulated by the neurotransmitter dopamine. The PPP1R1B gene 804 is located within the same TAD as the NEUROD2 (Neuronal differentiation 2) gene 802, and the same enhancer in both neuronal and astrocytic cell lines regulates both genes. Additionally, the TAD that contains these genes makes trans-interactions with TADs containing the DRD2 (Dopamine receptor D2) 806 and ADORA2A (Adenosine A2a receptor) genes 808, which are also controlled by the same neuronal and astrocytic enhancers in their respective TADs. Following use of methods described herein, the PPP1R1B pathway, although not a known drug pharmacogenomic network, is significantly interconnected in the human brain (p=1E-88), and seven of these genes are contained within the ketamine pharmacogenomic network, including BDNF, DRD2, GRIA1, GRIN1, GRIN2A and KLF6, as well as PPP1R1B. Four genes are contained with the ketamine neuroplasticity sub-network of the ketamine pharmacogenomic network as shown in FIG. 29 and FIG. 16C, while the other four are contained within the glutamate receptor sub-network of the ketamine pharmacogenomic network. Comparing the location of gene expression among different human brain regions of the different genes within the PPPR1B pathway, only 14 are expressed at detectable levels in the human brain. With the exception of GRIA1, GRIN), and GRIN2A, which are more broadly expressed within human brain, the expression of the remaining 11 genes in this pathway, as determined by RNA-seq data in humans, show a remarkably circumscribed pattern of gene expression, limited to the anterior caudate, nucleus accumbens and putamen (FIG. 16D).

Figure 18:
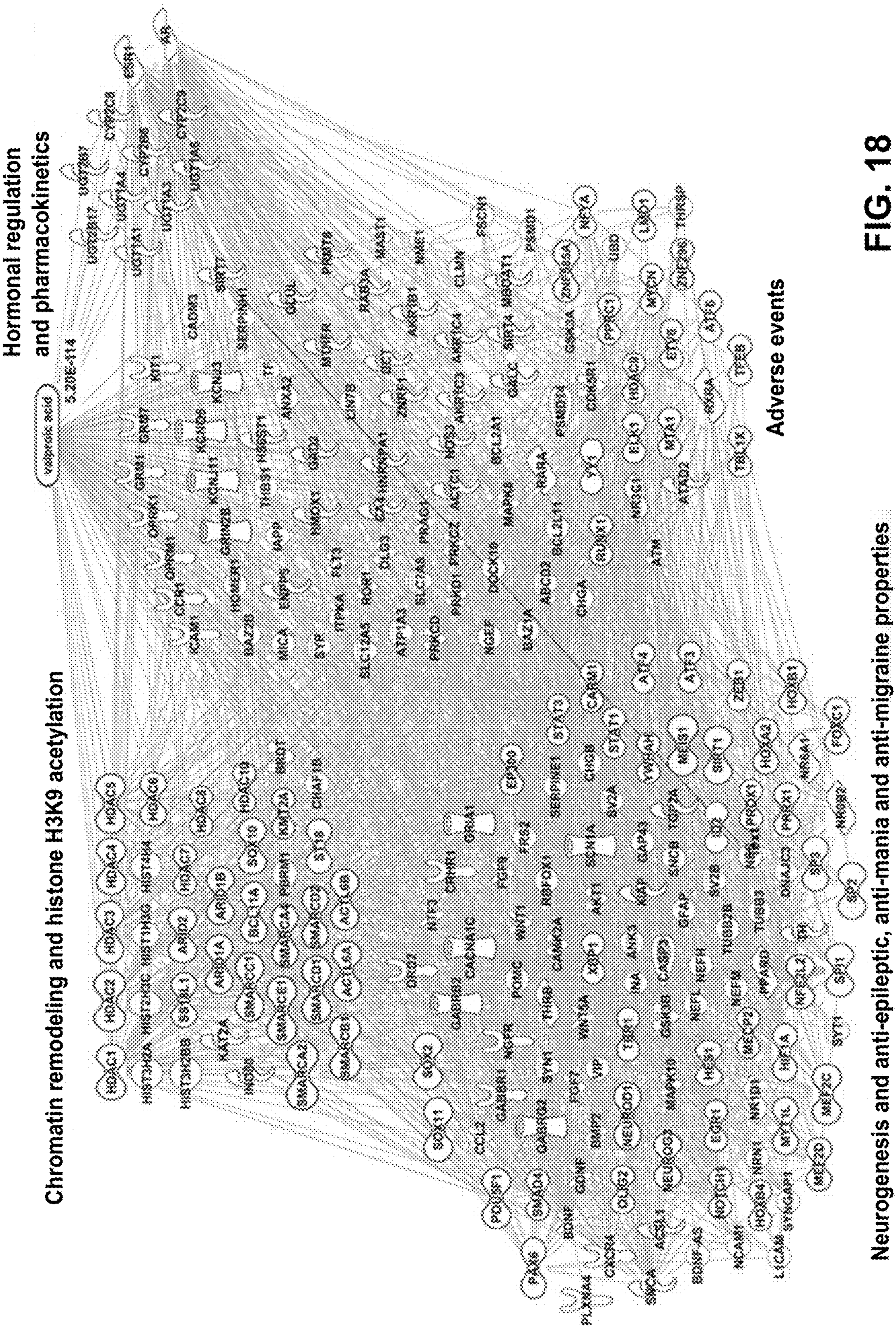
FIG. 18 illustrates a graphical depiction of the valproic acid pharmacogenomic network and its constituent sub-networks, including chromatin remodeling, efficacy, adverse events and hormonal control and pharmacokinetics, in human brain using the methods and systems of this invention.
Figure 21:
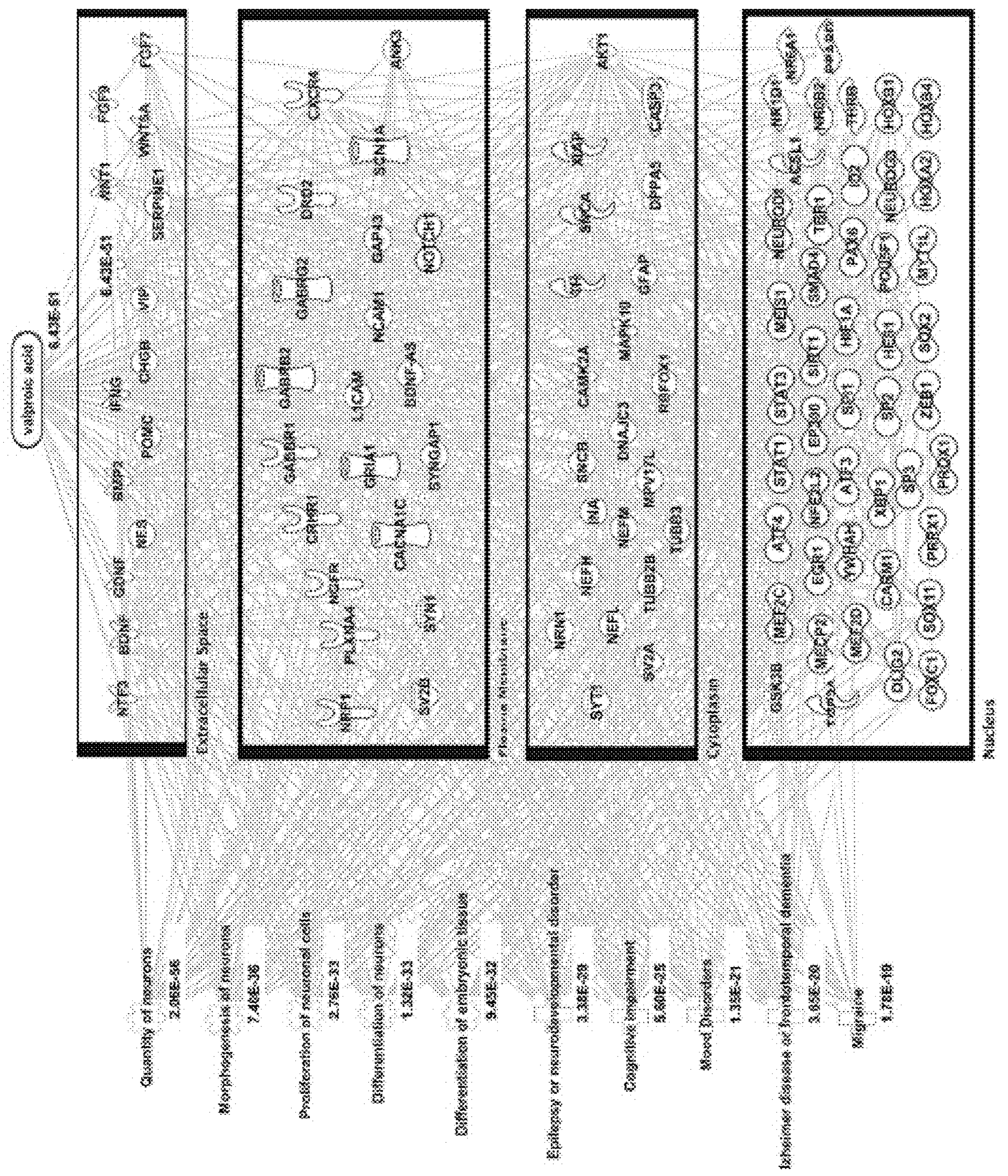
FIG. 21 illustrates an example of the valproic acid pharmacogenomic neurogenesis sub-network, and post-hoc bioinformatics analysis demonstrates that the valproic acid pharmacogenomic neurogenesis is significantly associated with quantity of neurons, morphogenesis, proliferation of neuronal cells, differentiation of neurons, differentiation of embryonic tissue, epilepsy or neurodevelopmental disorder, cognitive impairment, mood disorders, Alzheimer's disease or frontotemporal dementia, and migraine.
Figure 32:
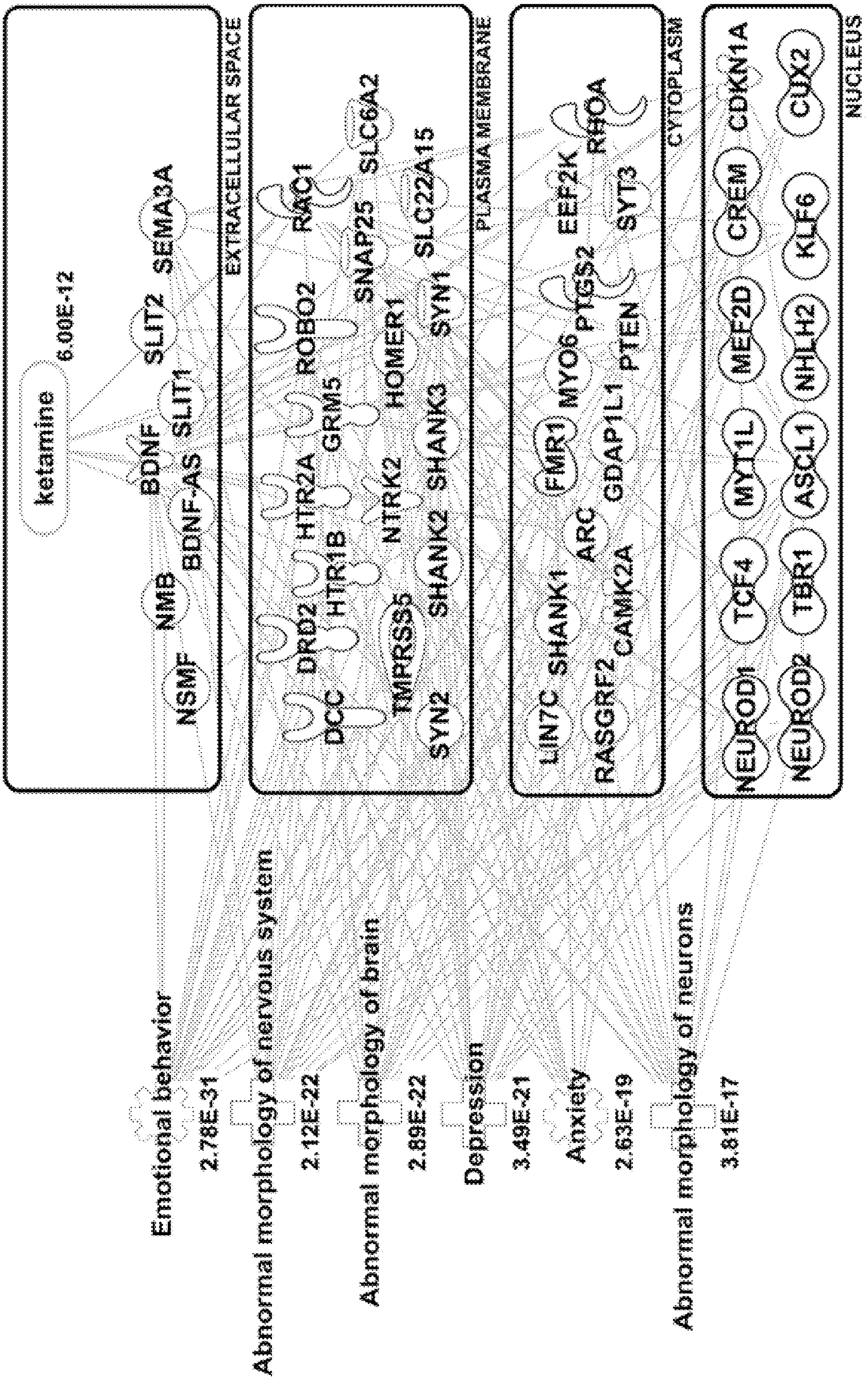
FIG. 32 illustrates an example of the ketamine pharmacogenomic neuroplasticity sub-network, and post-hoc bioinformatics analysis demonstrates that the ketamine pharmacogenomic neuroplasticity sub-network is significantly associated with emotional behavior, abnormal morphology of the nervous system, abnormal morphology of brain, depression, anxiety, and abnormal morphology of neurons.
Figure 43:
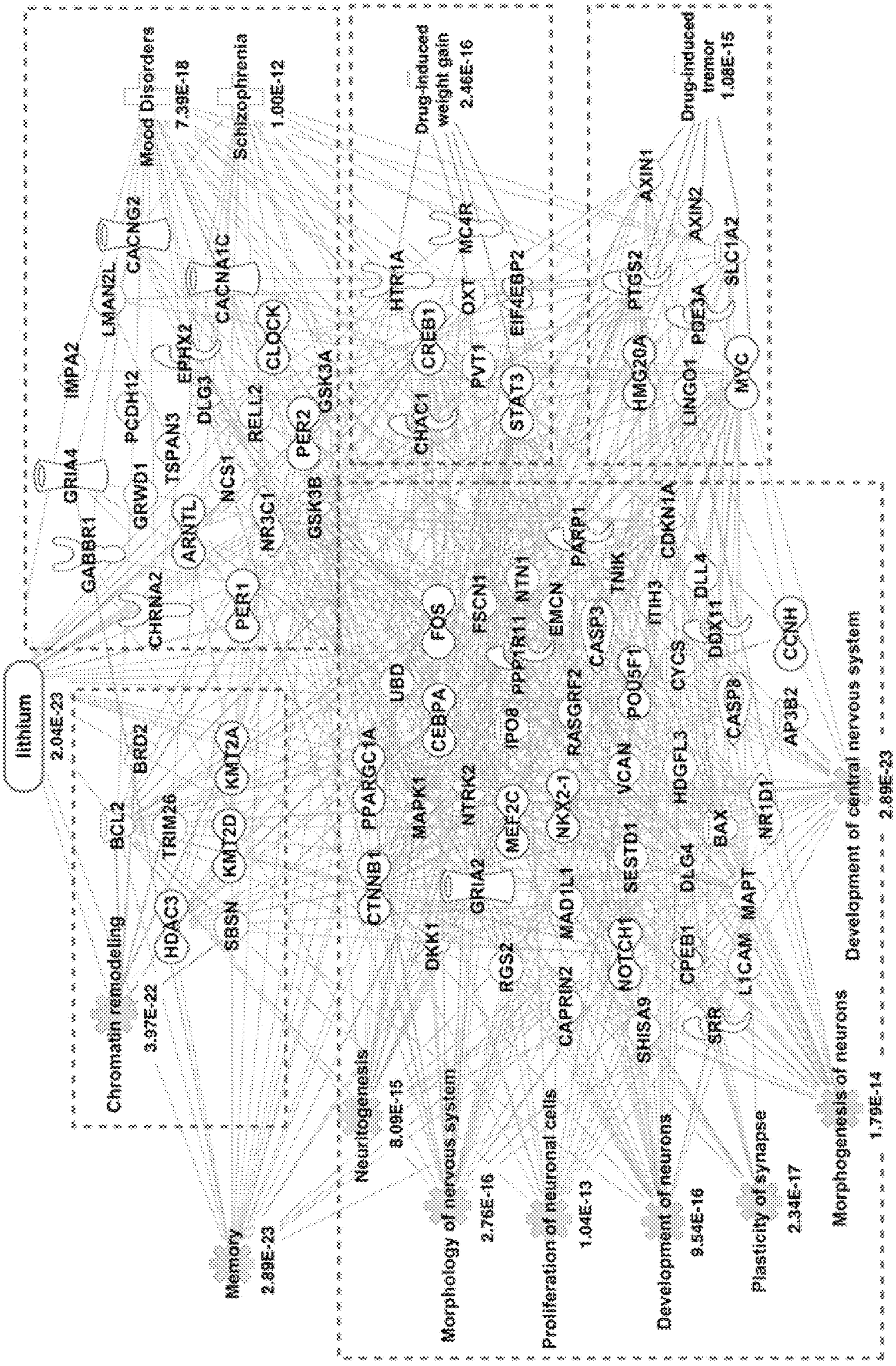
FIG. 43 illustrates a high-resolution compartmentalization of gene set sub-networks as an example of one output using this system for the lithium pharmacogenomic network.

At block 810, the drug pharmacogenomic network server 102 performs a bioinformatics analysis of the PPP1R1B pathway limited to those 14 genes expressed in the human brain. The bioinformatics analysis shows that the 14 genes are significantly associated with neuronal differentiation, neuronal development and regulation of neurogenesis and CNS development, as well as opioid drug signaling. These characteristics are shared with the neuroplasticity sub-network of the valproic acid pharmacogenomic network as shown in FIGS. 18 and 21, the neuroplasticity sub-network of the ketamine pharmacogenomic network as shown in FIG. 32, and the lithium pharmacogenomic network as shown in FIG. 43.

Figure 39:
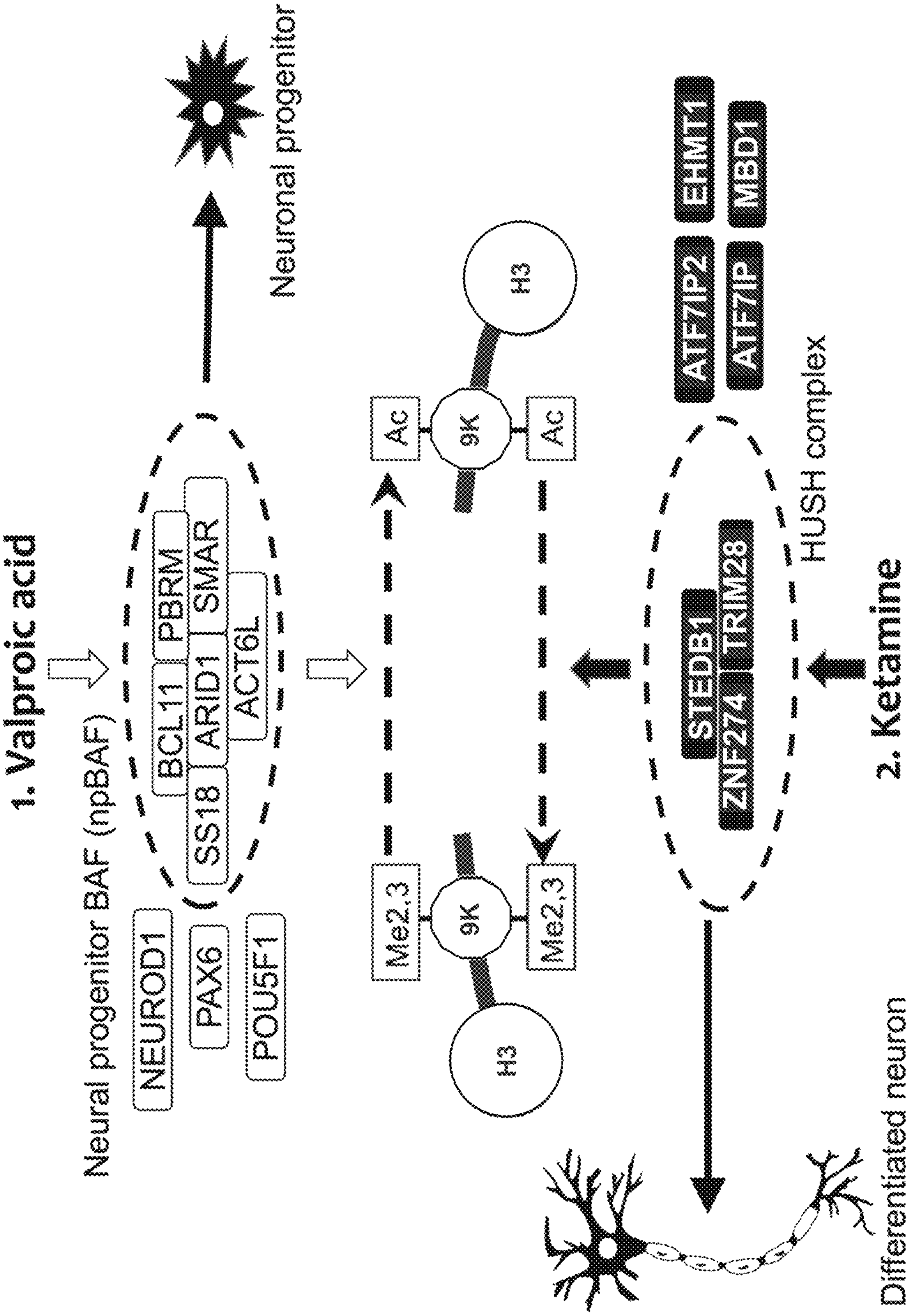
FIG. 39 illustrates an example of beneficial combinatorial mechanisms and therapeutics discovered using methods of this system using valproic acid and ketamine in H3K9 acetylation and deacetylation respectively, leading to neurogenesis and neuro-differentiation, in combination.
Figure 40A:
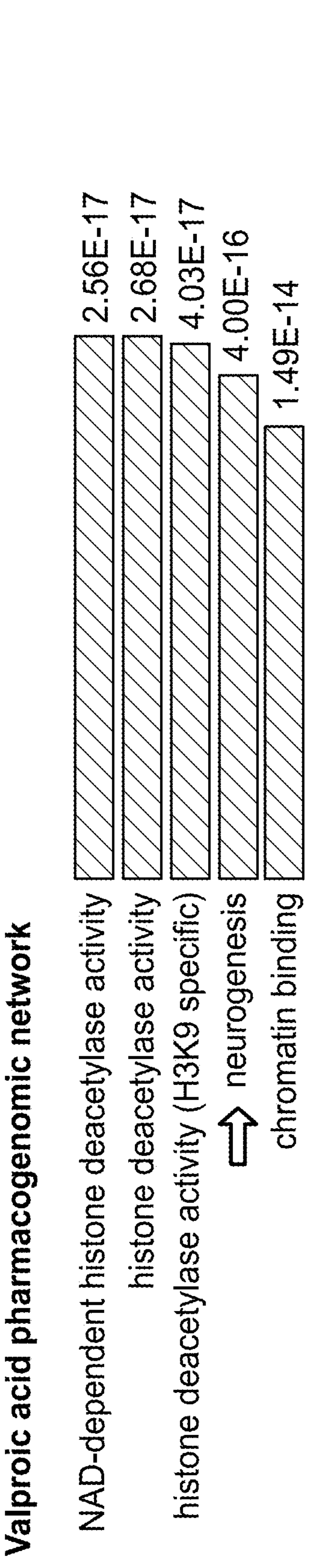
FIGS. 40A-40B illustrate the complementary pharmacogenomic network of valproic acid, FIG. 40A, and the pharmacogenomic network of ketamine, FIG. 40B, showing neurogenesis and neuro-differentiation, respectively.
Figure 40B:
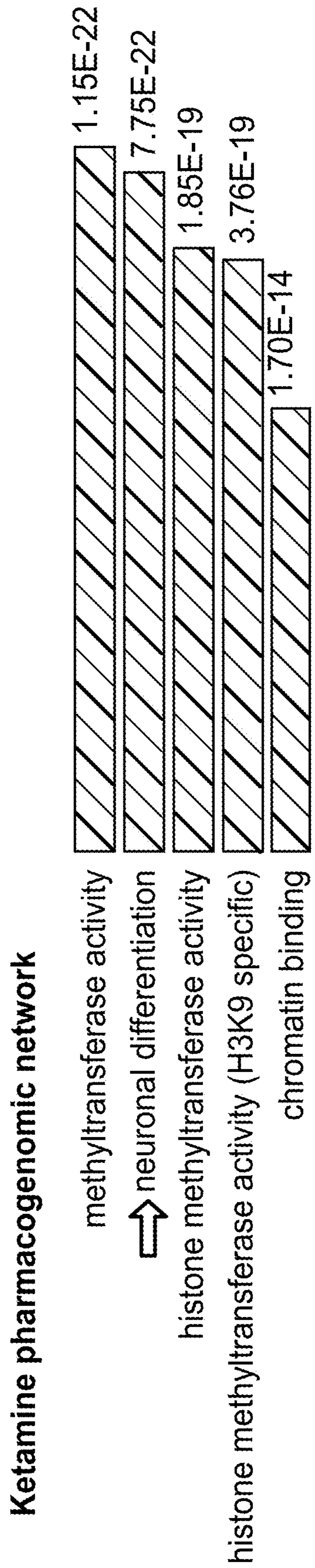
Figure 41:
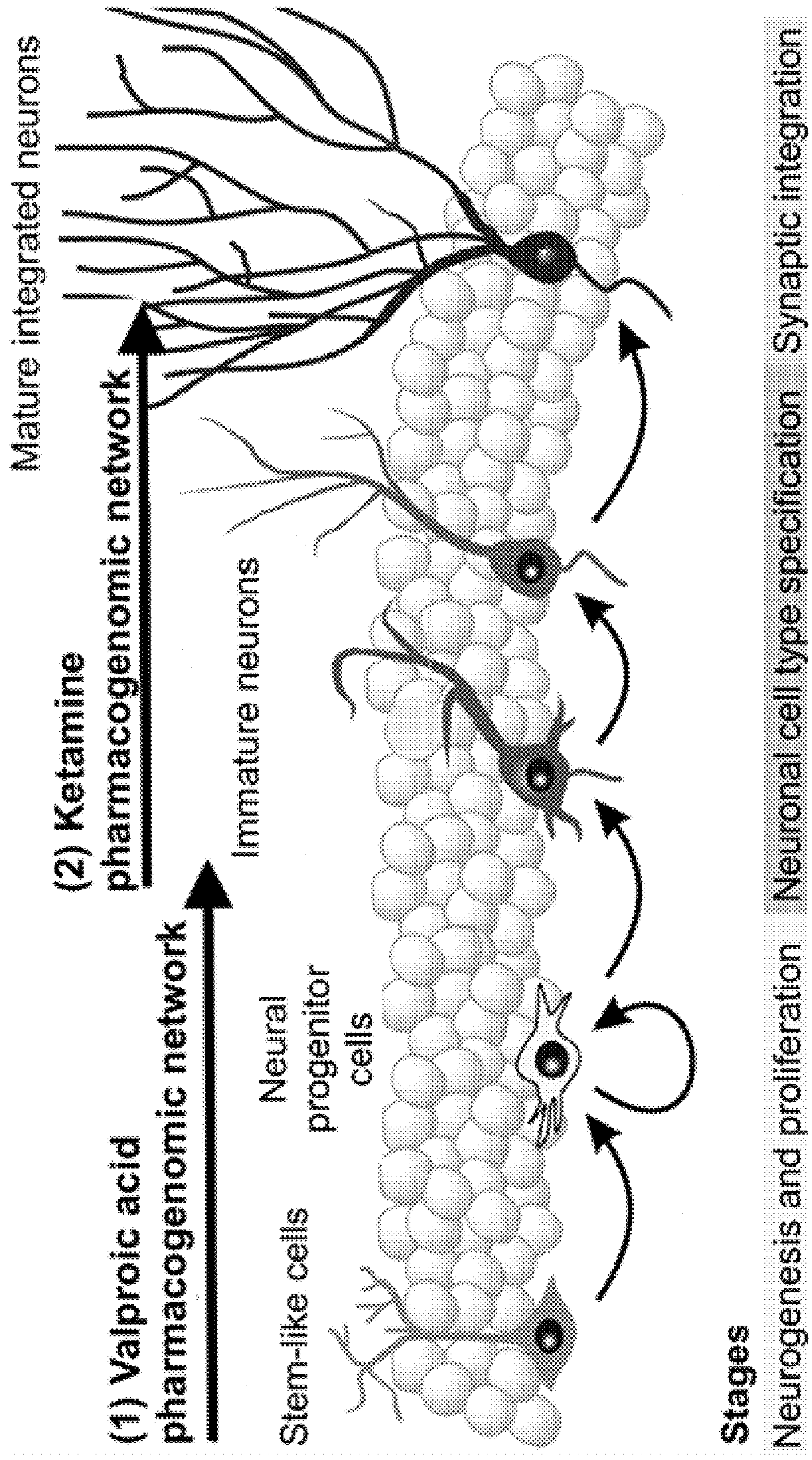
FIG. 41 illustrates the combinatorial actions of valproic acid and ketamine pharmacogenomic networks in neurogenesis, neuronal proliferation and terminal neuronal differentiation.

As shown in FIGS. 39, 40, and 41, the pharmacogenomic network identification system 100 may reveal complementary properties of existing medications that may be combined together as a new drug compound, may be administered sequentially, or similar combinations of drugs from the same drug class may be identified to provide a more comprehensive therapy for a given clinical indication. FIG. 41 illustrates that the valproic acid neurogenesis pharmacogenomic sub-network is enriched to stimulate early neurogenesis and the ketamine neuroplasticity sub-network is responsible for late neurogenesis. FIG. 39 shows that one mechanism through which this combination of therapeutics operates is through sequential acetylation and deacetylation of the histone lysine 9 (H3K9) moiety. Thus, valproic acid combines histone deacetylation inhibition with induction of the neural progenitor BAF chromatin remodeling complex for conversion of pluripotent neuronal precursor cells into committed neuronal progenitors as shown in FIG. 39 (top), and ketamine converts committed neuronal progenitor cells into terminally differentiated neurons through activation of the HUSH (human silencing complex) and H3K9 methylation (FIG. 39, bottom).

FIG. 40 illustrates gene set enrichment of the nuclear genes contained within the valproic acid pharmacogenomic network (FIG. 40A) and the ketamine pharmacogenomic network (FIG. 40B). FIG. 40A illustrates that analysis of the valproic acid pharmacogenomic network is enriched both for H3K9 histone deacetylase activity and neurogenesis, and FIG. 40B shows that the ketamine pharmacogenomic network is enriched both for H3K9 histone methyltransferase activity and neuronal differentiation.

Thus, as shown in FIG. 41, it may be possible to combine these approved drugs in clinical use to provide a comprehensive solution to provide both early and mid to late neurogenesis, including mechanisms of neurogenesis, neuronal proliferation, neuronal differentiation and synaptic integration. For example, a first drug such as valproic acid may be administered to the patient at a first point in time and then a second drug such as ketamine may be administered to the patient at a second point in time later than the first point in time. Thus, this combination of FDA-approved therapeutics may not only be used in disease states in which neuronal cell loss is a characteristic feature of the disorder, but also in the aging human brain to sustain the integrity of gray matter. Disease states might include neurological disorders, neurodegenerative disorders such as frontotemporal dementia, Alzheimer's disease and Parkinson's disease, as well as neuropsychiatric disorders including bipolar disorder and schizophrenia, and acute brain injury.

For example, a method for treating a patient with a neurodegenerative disorder may include administering valproic acid to the patient and administering ketamine to the patient. In some embodiments, the method may include obtaining a biological sample of a patient and comparing or having compared the biological sample to one or more SNPs in the valproic acid pharmacogenomic network which are associated with neurogenesis. The method may also include comparing or having compared the biological sample to one or more SNPs in the ketamine pharmacogenomic network which are associated with neuronal differentiation. In response to determining that the biological sample of the patient includes both SNPs in the valproic acid pharmacogenomic network which are associated with neurogenesis and SNPs in the ketamine pharmacogenomic network which are associated with neuronal differentiation, valproic acid and ketamine may be administered to the patient to treat the patient's neurogenerative disorder.

More generally, the pharmacogenomic network identification system 100 may identify pharmacogenomic networks for any number of drugs. Then for a first and second drug, the pharmacogenomic network identification system 100 may compare properties (e.g., drug response phenotypes) associated with the genes within the pharmacogenomic network and/or constituent sub-networks for the first drug to properties (e.g., drug response phenotypes) associated with the genes within the pharmacogenomic network and/or constituent sub-networks for the second drug to identify complementary properties between the first and second drugs. When complementary properties for a set of drugs, such as early stage neurogenesis and late stage neurogenesis, are identified, the set of drugs may be re-purposed to test as a therapeutic for a particular disease or disease state.

FIG. 18 shows the valproic pharmacogenomic network in the human central nervous system and its constituent sub-networks as outputs of the system. The gene subnetworks consist of: (1) chromatin remodeling and H3K9 acetylation, (2) neurogenesis and anti-epileptic, anti-mania, and anti-migraine properties, (3) adverse events, and (4) hormonal regulation and pharmacokinetics.

Figures 19A, 19B, 19C:
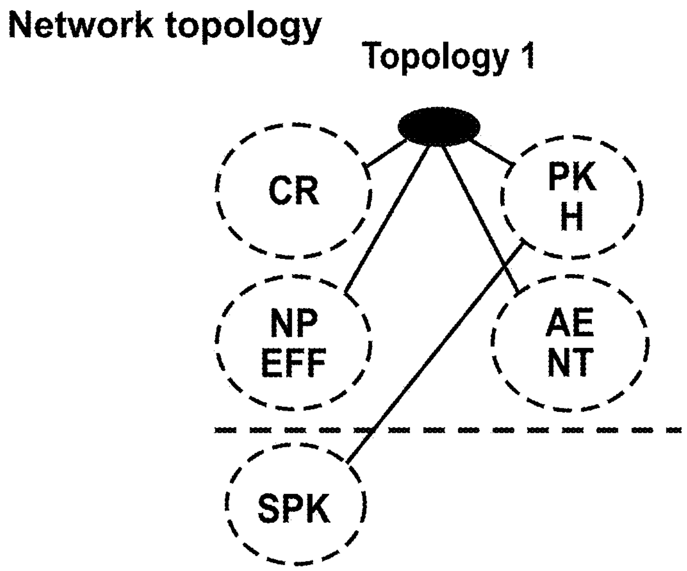
FIG. 19A illustrates the most significant disease annotations of the valproic acid pharmacogenomic network.
FIG. 19B illustrates the top 10 drugs that are upstream regulators of the valproic acid pharmacogenomic network.
FIG. 19C illustrates the topology model that most accurately fits the valproic acid pharmacogenomic network.

FIG. 19 shows the results of post-hoc bioinformatics analysis of the valproic acid pharmacogenomic network and its concomitant network topology model. FIG. 19A shows that the most significant disease annotations of the gene contained in the valproic acid pharmacogenomic network are epilepsy or neurodevelopmental disorder, cognitive impairment, mood disorders, migraine, and mania. It should be noted that valproic acid is indicated for sole and adjunctive therapy in the treatment of simple and complex absence seizures, and adjunctively in patients with multiple seizure types which include absence seizures, in the treatment of mania in bipolar disorder and other mood disorders, and to prevent and alleviate migraine headache. A common adverse event of valproic acid is cognitive clouding (cognitive impairment).

FIG. 19B shows the most significant drugs that act as upstream regulators of the valproic acid pharmacogenomic network, including valproic acid (p value=5.20E-114; Fisher's exact test), the HDAC inhibitor Trichostatin A (p=3.21E-35), and nicotine (p=5.57E-21).

FIG. 19C shows that the valproic acid pharmacogenomic network fits the model network topology label 1, with deconstructed gene set sub-networks that comprise chromatin remodeling (CR). neuroplasticity and drug efficacy (NP. EFF). adverse events and neurotransmission (AE, NT), and pharmacokinetics and hormonal regulation (PK, H). The non-CNS, peripheral systematic pharmacokinetic (SPK) sub-network of the valproic acid pharmacogenomic network cannot be determined from the output of this system.

FIG. 28 illustrates examples of trans-interactions in the 3D chromatin space of the valproic acid pharmacogenomic network as output of the methods and systems described herein. Whole genome, Hi-C data mapping performed using SNPs as data probes, the probes including SNPs contained within the valproic acid sub-networks and obtained from the GWAS catalog, including those which has been significantly associated with disease risk and valproic acid response variation and dissociation. These results were used to detect both cis- and trans-interactions with other members of the valproic acid pharmacogenomic pathway within human neurons. FIG. 28A shows a whole genome plot that is the key for understanding the gene-gene interactions shown in FIG. 28B-28I as determined by the Hi-C method. FIG. 28B shows Hi-C contacts between GABBR1, a gene that encodes a receptor for gamma-aminobutyric acid (GABA), which is the main inhibitory neurotransmitter in the human CNS, and enhancer mutations in this gene underlie brain disorders such as epilepsy, and CRHR1 and CRHR1-IT1, genes important for neural progenitor cell differentiation under the control of several super enhancers, corticotropin hormone binding in the adult brain, and mutations associated with anxiety and mania. FIG. 28C shows spatial Hi-C contacts in human neurons between GABRG2, a gene that encodes a GABA receptor in which mutations are significantly associated with febrile and infantile epilepsy, and KCNJ3. a gene that encodes a potassium channel in the human CNS in which mutations have been significantly associated with cognition and epilepsy. FIG. 28C shows spatial Hi-C contacts in human neurons between RUNX1, a transcription factor, and HDAC9, a member of the histone deacetylase superfamily. Mutations in the enhancers and super enhancers of both genes are significantly associated with alopecia and minor hair loss, an adverse event associated with valproic acid therapy. FIG. 28E shows spatial Hi-C contacts in human neurons between GABRB2, GABRG2. genes that encode GABA receptors and in which mutations have been associated with ataxia and epilepsy, and KCNQ5, a potassium channel gene in which mutations of the super enhancer have been significantly associated with autosomal mental retardation and intellectual disability. FIG. 28F shows spatial Hi-C contacts in human neurons between NEUROD1, a master transcription factor involved in neurogenesis and implicated in valproic acid response in humans, and NEUROG3, a transcription factor involved in the cell lineage commitment of neural progenitors to neurons. FIG. 28G shows spatial Hi-C contacts in human neurons between GRIN2A, a gene that encodes a member of the N-methyl-D-aspartate (NMDA) receptor in which mutations have been significantly associated with schizophrenia, bipolar disorder, and mania, and ANK3, a gene that encodes a member of the synaptic cytoskeleton and in which mutations have been significantly associated with bipolar disorder, chronotype, and schizophrenia. FIG. 28H shows spatial Hi-C contacts in human neurons between GRIN2B, a gene that encodes a member of the NMDA receptor, and SNCA, a pre-synaptic protein and in which mutations of its super enhancer are significantly associated with late onset Parkinson's disease. FIG. 28I shows spatial Hi-C contacts in human neurons between PAX6, a gene that encodes a master transcription factor responsible for early development of the human central nervous system, eye and nose, and SOX2, a gene related to PAX6 that controls the neural progenitor BAF remodeling complex responsible for neurogenesis.

Figure 20:
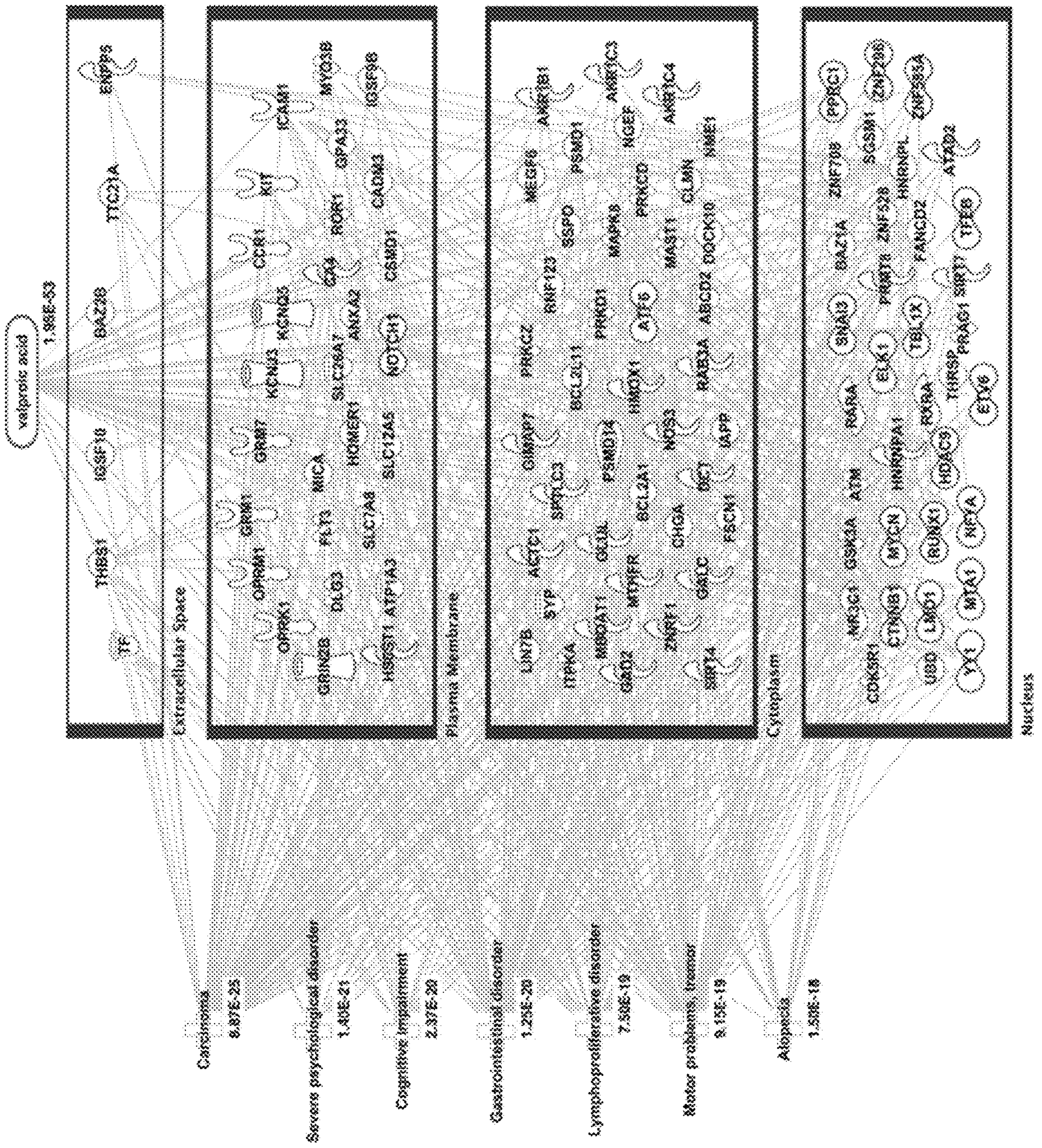
FIG. 20 illustrates an example of the valproic acid pharmacogenomic adverse event sub-network, and post-hoc bioinformatics analysis demonstrates that the valproic acid pharmacogenomic adverse event sub-network is significantly associated with carcinoma, severe psychological disorder, cognitive impairment, gastrointestinal disorder, lymphoproliferative disorder, motor problems, including tremor, and alopecia.

FIG. 20 illustrates the valproic acid pharmacogenomic adverse event sub-network and post hoc bioinformatics analysis shows that the valproic acid adverse event sub-network is significantly associated with cancer, severe psychological disorders, gastrointestinal disorders, tremor, and alopecia.

FIG. 21 illustrates the valproic acid pharmacogenomic neuroplasticity sub-network and post hoc bioinformatics analysis shows that the glutamate receptor sub-network is significantly associated with neurogenesis, neuronal differentiation, and neuronal proliferation, as well as disease states including epilepsy, mood disorders, and migraine.

FIG. 22 illustrates examples from 237 unique GWAS disease risk and pharmacogenomic SNPs that can be used to discriminate an individual patient's efficacy and adverse event profile in response to the anti-epileptic, anti-mania, and anti-migraine properties of valproic acid. FIG. 22A shows that multiple GWAS disease risk SNPs located within the valproic acid adverse event sub-network can be annotated as enhancers and super enhancers associated with alopecia, gastrointestinal disorders mediated by the CNS, and the reduced efficacy of the mixed antidepressant bupropion in bipolar depression. FIG. 22B shows that the valproic acid pharmacogenomic neuroplasticity sub-network contains multiple GWAS disease risk and pharmacogenomic SNPs that can be annotated as enhancers and super enhancers significantly associated with chronic migraine, epilepsy, bipolar disorder (International Classification of Disease (ICD) codes F31.0-F31.64), and the efficacy of valproic acid in bipolar mania.

Figure 23:
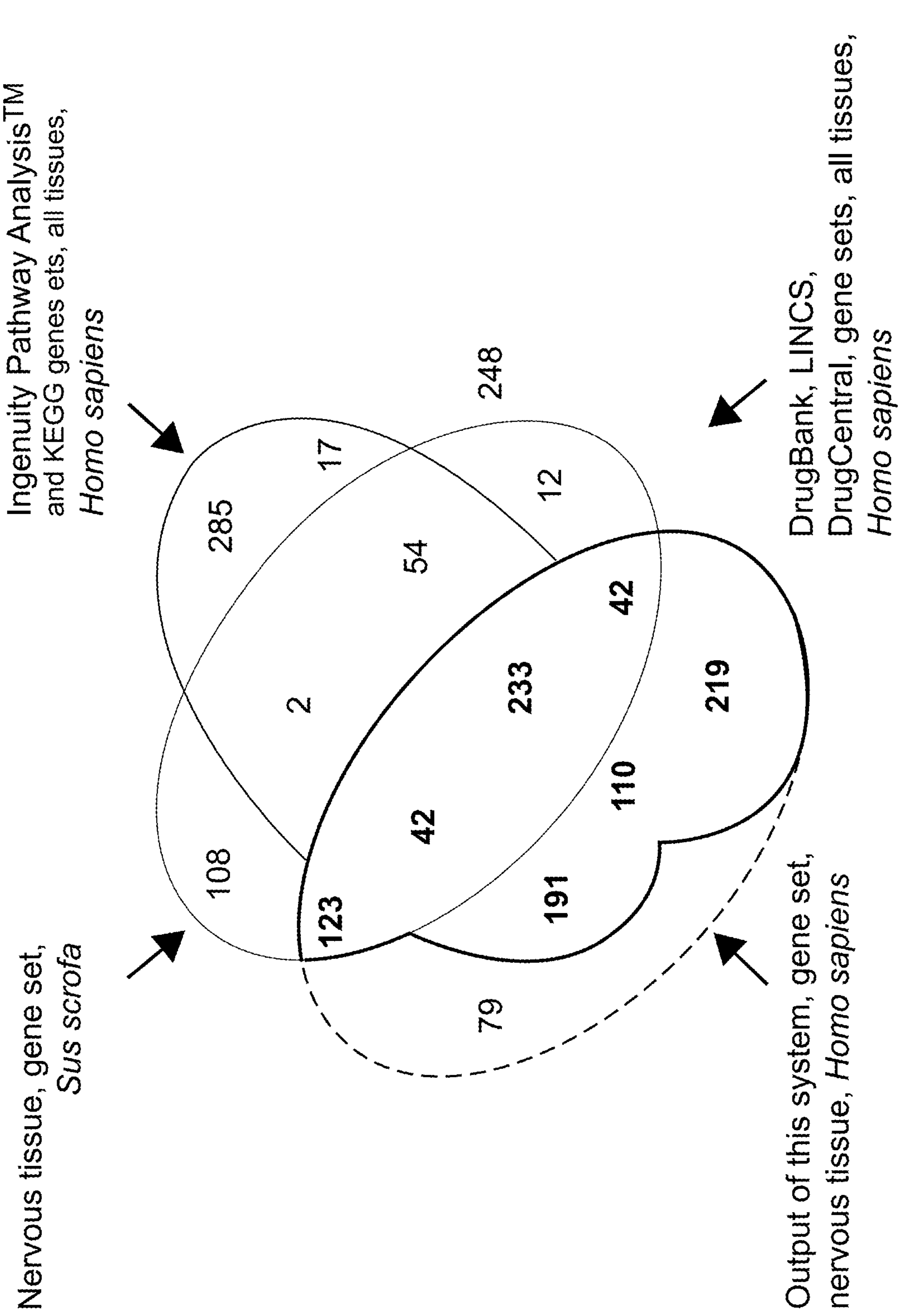
FIG. 23 illustrates the overlap of the output using this system and methods with 4 other experimental and existing data sources, including genes that are significantly differentially-expressed from pig (*Sus scrofa*) brain following peripheral administration of 150 mg/kg of valproic acid, and drug databases including Ingenuity Pathway Analysis™, KEGG, DrugCentral, DrugBank, and LINCS. Note that this system outputs the greatest number of shared valproic acid-induced genes than any other 2 comparisons.
Figure 28A:
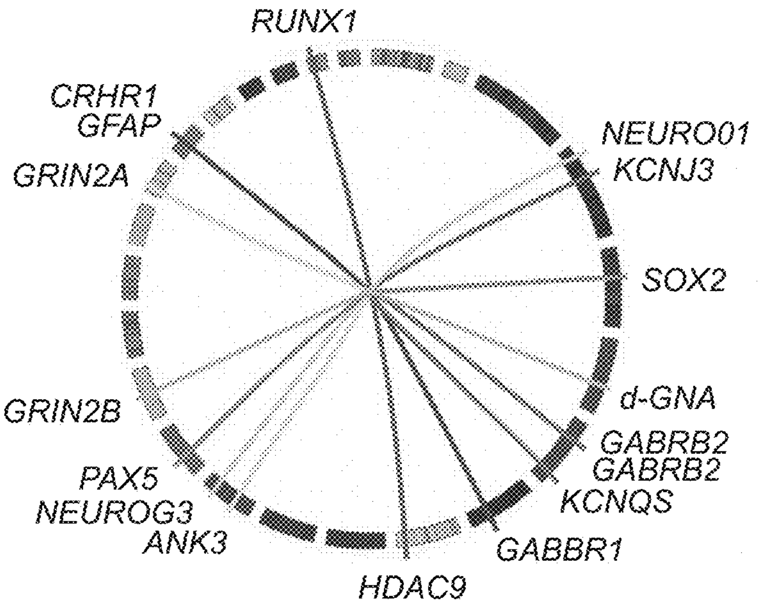
FIGS. 28A-28I illustrate selected chromatin spatial contacts of the valproic acid pharmacogenomic network and its functional networks determined by chromosome conformation capture using the Hi-C method in human neurons.
Figure 28B:
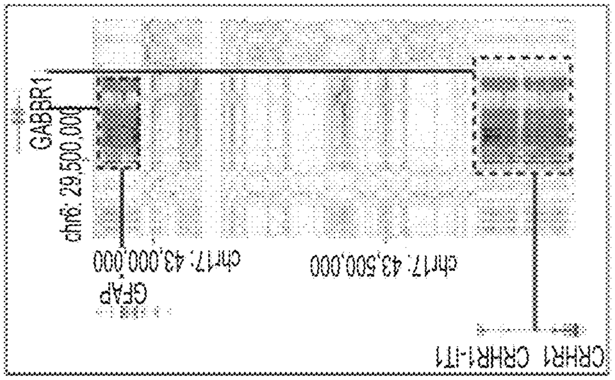
Figure 28C:
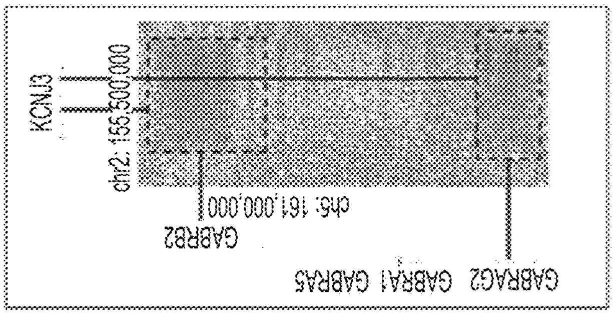
Figure 28D:
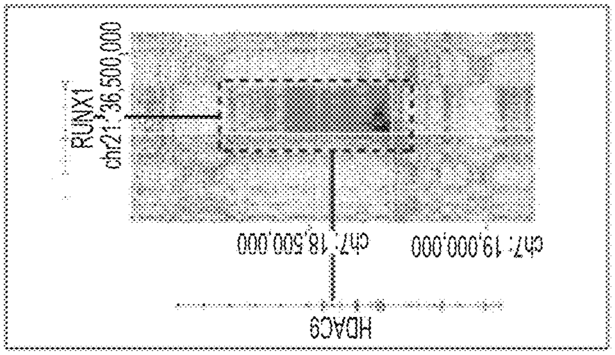
Figure 28E:
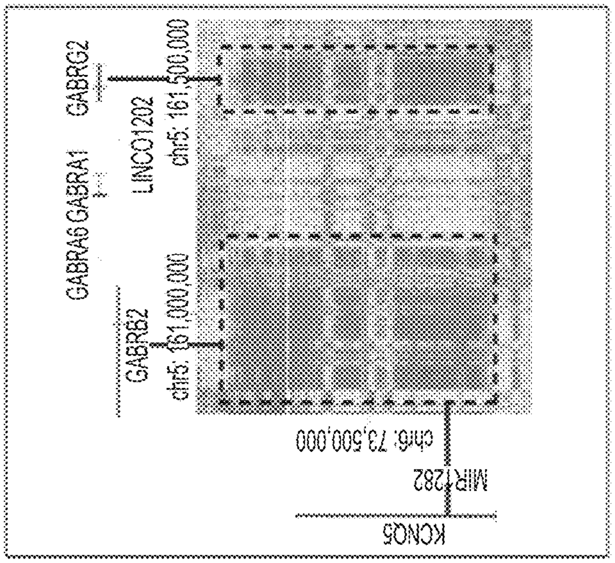
Figure 28F:
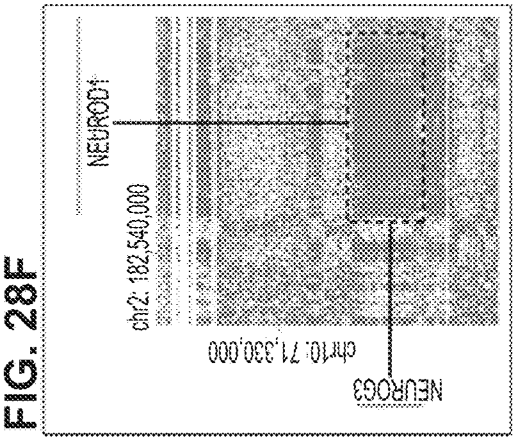
Figure 28G:
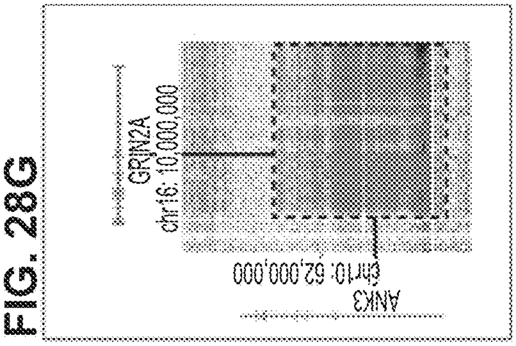
Figure 28H:
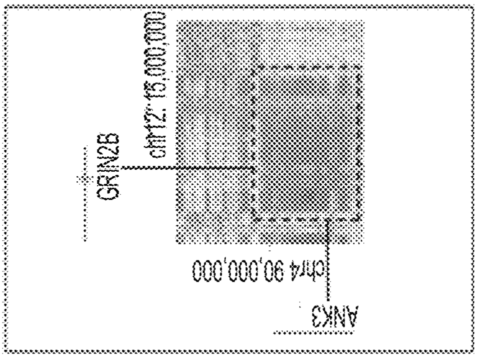
Figure 28I:
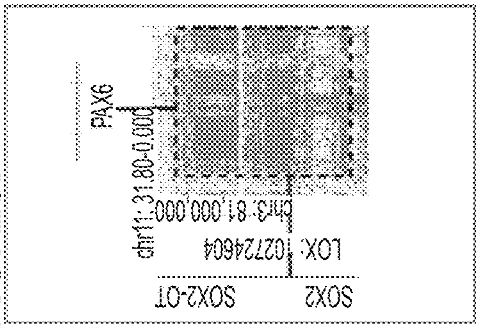

FIG. 23 illustrates validation of the system by comparison to results of experimental results and public data contained in the most widely used open source and commercial drug databases. The Venn diagram is a graphical depiction of the output of this invention for the valproic acid pharmacogenomic network genes in human nervous tissue compared to the differentially-regulated genes by valproic acid following administration of the drug to the control brain of the pig (*Sus scrofa*), and finite sets of genes that are considered to be regulated by valproic acid in all human tissues using the Ingenuity Pathway Analysis™ (IPA; Qiagen; GmBH) and the Kyoto Encyclopedia of Genes (KEGG), and DrugBank, the LINCS database from the National Institutes of Health, and DrugCentral. The set of genes of the valproic acid pharmacogenomic network as output from the system described herein demonstrate the highest degree of overlap in all of the one-on-one comparisons of the results and the data from all of these sources.

FIG. 24 is a list of all of the genes contained in the chromatin remodeling (CR) sub-network of the valproic acid pharmacogenomic network in the human brain.

FIG. 25 is a list of all of the genes contained in the neuroplasticity and drug efficacy (NP, EFF) sub-network of the valproic acid pharmacogenomic network in the human brain.

FIG. 26 is a list of all of the genes contained in the adverse events and neurotransmission (AE, NT) sub-network of the valproic acid pharmacogenomic network in the human brain.

FIG. 27 is a list of all of the genes contained in the pharmacokinetics and hormonal regulation (PK. H) sub-network of the valproic acid pharmacogenomic network in the human brain.

Figures 29A, 29B, 29C:
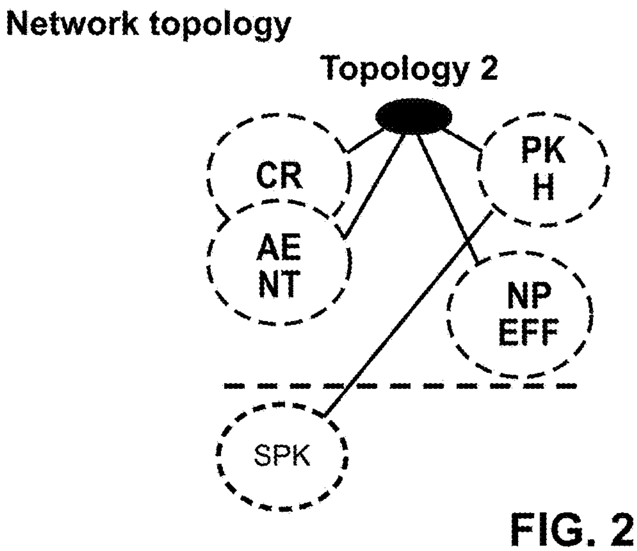
FIG. 29A illustrates the most significant disease annotations of the ketamine pharmacogenomic network.
FIG. 29B illustrates the top 5 drugs that are upstream regulators of the ketamine pharmacogenomic network.
FIG. 29C illustrates the topology model that most accurately fits the ketamine pharmacogenomic network.

FIG. 29 shows the results of post-hoc bioinformatics analysis of the ketamine pharmacogenomic network and its concomitant network topology model. FIG. 29A shows that the most significant disease annotations of the gene contained in the ketamine pharmacogenomic network are schizophrenia, refractory depression, bipolar disorder, post-operative delirium, and postoperative pain.

FIG. 29B shows the most significant drugs that act as upstream regulators of the ketamine pharmacogenomic network, including ketamine (p value=6.26E-33 ketamine; Fisher's exact test), morphine (p=1.97E-17), and nicotine (p=6.62E-17).

FIG. 29C shows that the ketamine pharmacogenomic network fits the model network topology label 2, with deconstructed gene set sub-networks that comprise chromatin remodeling (CR), adverse events (AE), and neurotransmission (NT), neuroplasticity and drug efficacy (NP, EFF), and pharmacokinetics and hormonal regulation (PK, H). The non-CNS, peripheral systematic pharmacokinetic (SPK) sub-network of the ketamine pharmacogenomic network cannot be determined from the output of this system.

Figure 37A:
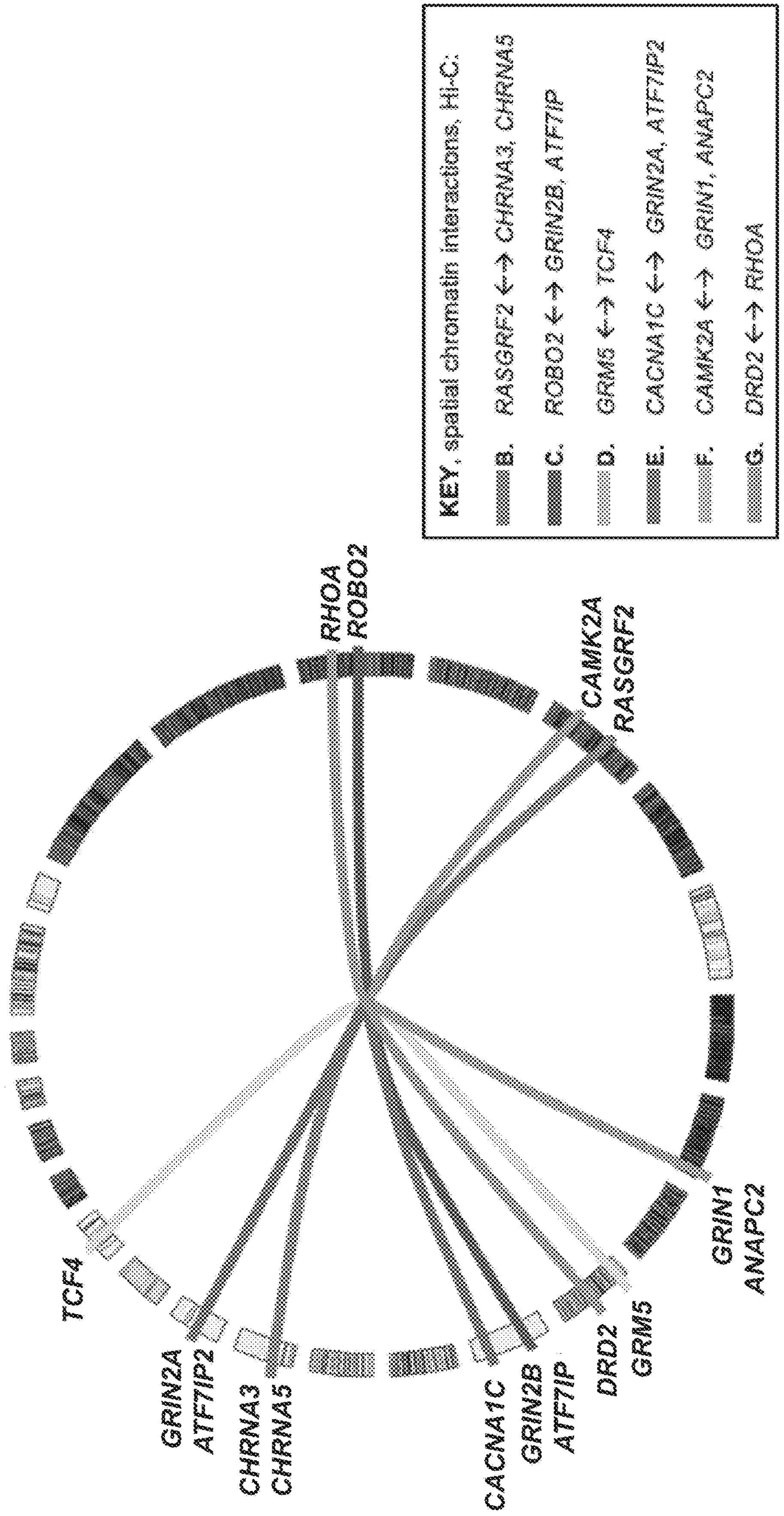
FIGS. 37A-37G illustrate selected chromatin spatial contacts of the entire ketamine pharmacogenomic network determined by chromosome conformation capture using the Hi-C method in human neurons.
Figures 37B, 37C, 37D, 37E, 37F, 37G:
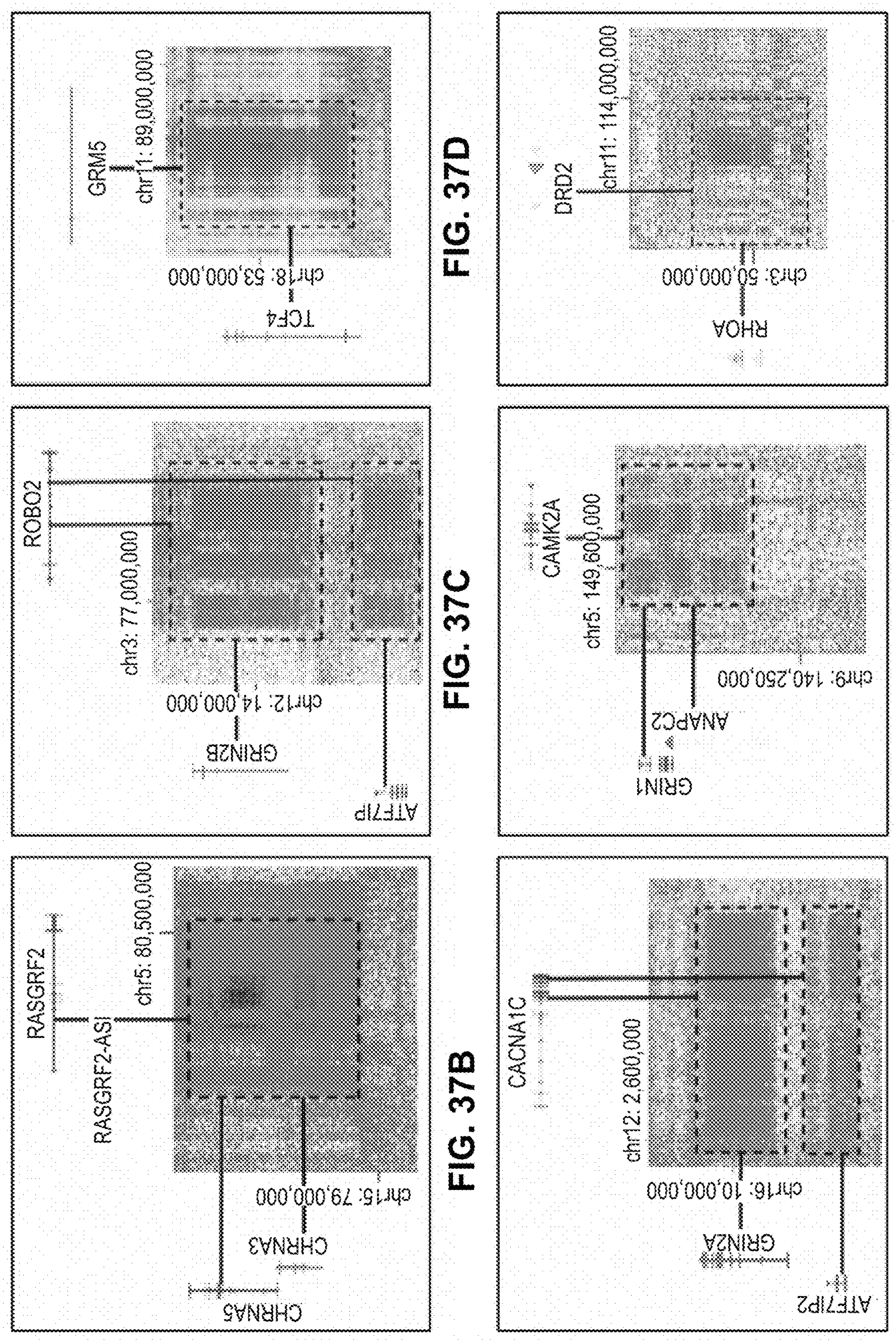

FIG. 37 illustrates examples of trans-interactions in the 3D chromatin space of the ketamine pharmacogenomic network as output of the methods and systems described herein. Whole genome, Hi-C data mapping performed using SNPs as data probes, the probes including SNPs contained within the ketamine sub-networks and obtained from the GWAS catalog, including those which has been significantly associated with disease risk and ketamine antidepressant response variation and dissociation. These results validated pathway analysis and demonstrated both cis- and trans-interactions with other members of the ketamine pharmacogenomic pathway within human neurons. These pharmacogenomic contacts are significantly enriched for association with specific super enhancers from cingulate cortex and frontal cortex. FIG. 37A shows a whole genome plot that is the key for understanding the gene-gene interactions shown in FIG. 37B-37G. FIG. 37B shows Hi-C contacts between RASGRF2, a gene associated with synaptic plasticity and alcoholism, with the co-localized nicotinic receptor genes CHRNA3 and CHRNA5 that contain SNPs significantly associated with smoking status in GWAS). FIG. 37C shows trans-interactions between the ROBO2 gene, which contains a number of SNPs associated with both unipolar depression and dissociative and antidepressant responses to ketamine in GWAS, and both the GRIN2B gene and the ATF7IP gene. The ATF7IP gene encodes a chromatin remodeling protein responsible for HUSH-mediated heterochromatin formation and gene silencing as part of the stabilization of the SETDB1 complex, required for methylation of histone 3 lysine 9 (H3K9me3). FIG. 37D demonstrates a pharmacogenomic contact between TCF4 and the GRMS gene, which encodes a member of the glutamate metabotropic receptor family and contains enhancers significantly associated with depression in GWAS. FIG. 37E shows a Hi-C map of interactions between CACNA1C and the GRIN2A and the ATF7IP2 genes. In FIG. 37F, Hi-C pharmacogenomic contacts obtained from human glutamatergic neurons shows trans-interactions between the CAMK2A gene located on chromosome 5 with the genes GRIN1 and ANAPC2 located on chromosome 9. The ANAPC2 protein is part of a complex that controls the formation of synaptic vesicle clustering at the active zone to the presynaptic membrane in postmitotic neurons, and this complex also degrades NEUROD2 as a primary component of pre-synaptic differentiation during neuronal differentiation. FIG. 37G shows pharmacogenomic contacts in neurons between the DRD2 gene and the RHOA gene, which encodes a signaling protein that regulates the cytoskeleton during synaptic transmission in neurons.

FIG. 38 illustrates the overlap between genes of the ketamine pharmacogenomic network in postmortem human brain and human brain regions where ketamine first exerts its rapid antidepressant response. This provides additional evidence in support of the ketamine pharmacogenomic network and is demonstrable by comparing the neuroanatomical distribution of gene expression data within the ketamine sub-networks with the localization results from a consensus brain-map showing which brain regions are first impacted by ketamine obtained from 24 neuroimaging studies. The consensus map emphasizes the anterior cingulate cortex (ACC), dorsolateral and dorsomedial prefrontal cortex (PFC), and the supplementary motor area (SMA) as consistently the first human brain regions to be activated by the drug. However, other CNS regions have been reported in neuroimaging studies to be rapidly impacted by ketamine in humans following administration of the drug. These are shown in black in FIG. 12A but did not comprise the clear majority of brain regions reported to be first impacted by ketamine in the neuroimaging studies that we examined during our research. To serve as controls, adjacent human brain regions were chosen which are not impacted by ketamine in the neuroimaging studies, including the corpus callosum (CC), occipital cortex (OC) and somatosensory cortex (SS). As shown in FIG. 12B, genes in the ketamine network are expressed at significantly higher levels in the ACC and PFC than in the neighboring CC, SS and OC, where there is no evidence that ketamine exerts rapid antidepressant effects. The ACC is part of the cingulate cortex, and the PFC is part of the frontal cortex.

Figure 30A:
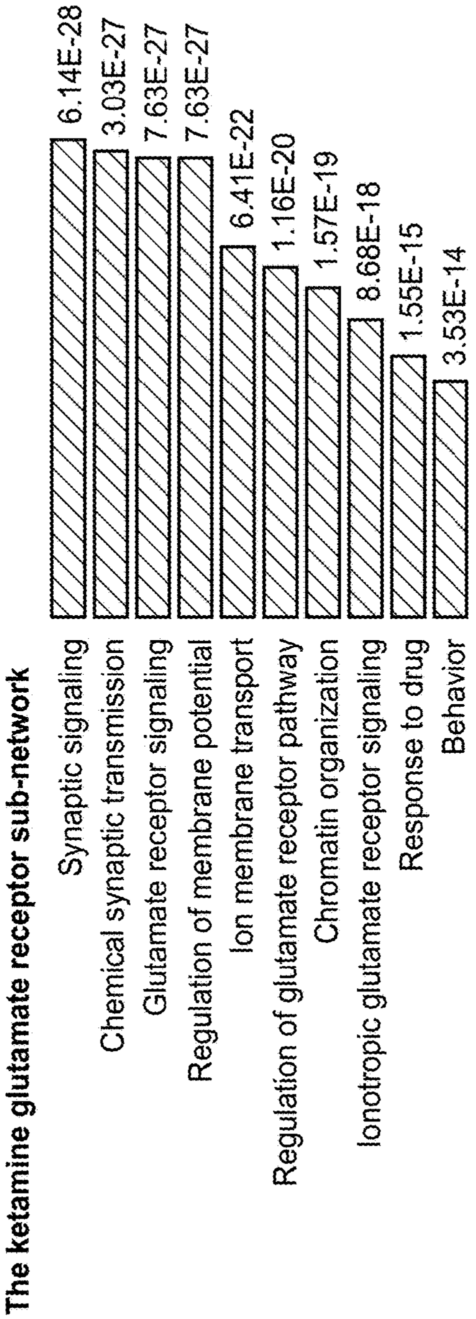
FIGS. 30A-30B illustrate an example gene set enrichment of the output of the gene set optimization engine that discriminated 2 significantly different sub-networks within the 3 sub-networks that comprise the ketamine pharmacogenomic network in human brain.
Figure 30B:
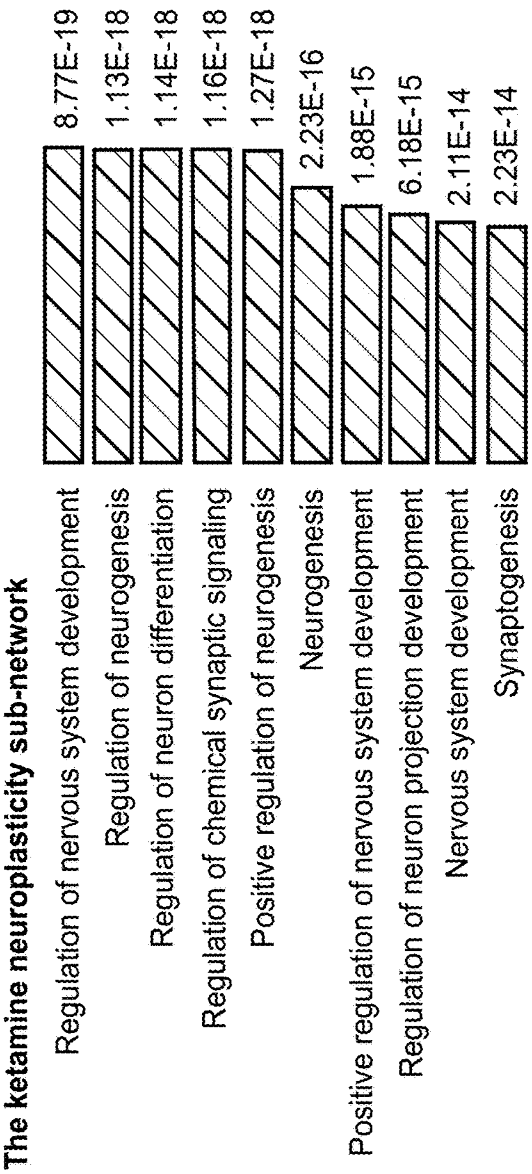

FIG. 30 illustrates the output of the iterative gene set optimization analysis of the ketamine pharmacogenomic network in human brain. The larger ketamine pharmacogenomic network contains 3 sub-networks, resulting in 2 distinctly different sub-networks. The glutamate receptor sub-network is enriched for synaptic signaling, glutamate receptor signaling, glutamate pathway regulation and chromatin organization. The top xenobiotic (chemical-drug) upregulator of the glutamate receptor sub-network is ketamine at p=2.1E-09 (FIG. 13A). In contrast, the neuroplasticity sub-network is enriched for regulation of nervous system development, regulation of neurogenesis, regulation of neuronal differentiation, neurogenesis and nervous system development (FIG. 13B). The neuroplasticity sub-network exhibits significant overlap with the "cardiovascular disease, neurological disease and organismal injury abnormalities" network category as determined by Ingenuity Pathway Analysis™ atp=1E-59 and its top xenobiotic up-regulator is also ketamine at p=6E-12.

Figure 31:
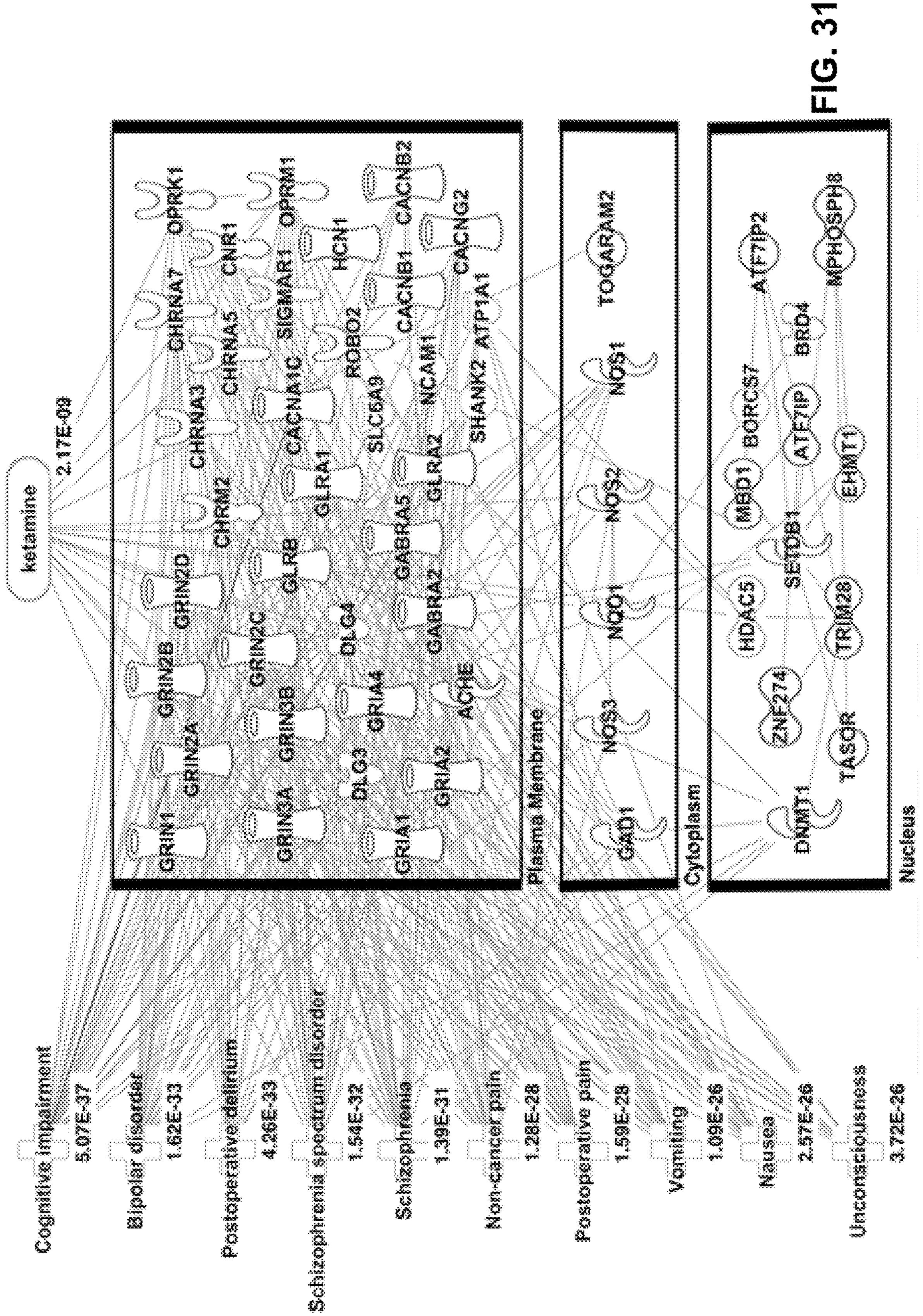
FIG. 31 illustrates an example of the ketamine pharmacogenomic glutamate receptor sub-network, and post-hoc bioinformatics analysis demonstrates that the ketamine pharmacogenomic glutamate receptor sub-network is significantly associated with the following adverse events (AEs): cognitive impairment, bipolar disorder, postoperative delirium, schizophrenia affective disorder, schizophrenia, non-cancer pain, postoperative pain, vomiting, nausea, and unconsciousness.

FIG. 31 illustrates the ketamine pharmacogenomic glutamate receptor sub-network and post hoc bioinformatics analysis shows that the glutamate receptor sub-network is significantly associated with cognitive impairment, bipolar disorder, postoperative delirium, schizophrenia affective disorder, schizophrenia, non-cancer pain, postoperative pain, vomiting, nausea, and unconsciousness.

FIG. 32 illustrates the ketamine pharmacogenomic neuroplasticity sub-network and post hoc bioinformatics analysis shows that the neuroplasticity sub-network is significantly associated with emotional behavior, abnormal morphology of the nervous system, abnormal morphology of brain, depression, anxiety, and abnormal morphology of neurons.

FIG. 33 illustrates examples from 108 unique GWAS disease risk and pharmacogenomic SNPs that can be used to discriminate an individual patient's efficacy and adverse event profile in response to the antidepressant and other actions of ketamine and its analogs. FIG. 33A shows that multiple GWAS disease risk SNPs located within the glutamate receptor sub-network can be annotated as enhancers associated with tobacco smoking status, chronic schizophrenia (ICD diagnostic code F20), and bipolar 1 disorder (ICD diagnostic codes F31.0-F31.64). FIG. 33B shows that the ketamine neuroplasticity sub-network contains multiple GWAS disease risk SNPs that can be annotated as enhancers associated with recurrent depression (ICD code F33), alcoholism and response to ketamine.

FIG. 34 is a list of all of the genes contained in the neuroplasticity and drug efficacy (NP, EFF) sub-network of the ketamine pharmacogenomic network in the human brain.

FIG. 35 is a list of all of the genes contained in the chromatin remodeling (CR), adverse events (AE), and neurotransmission (NT) sub-network of the ketamine pharmacogenomic network in the human brain.

FIG. 36 is a list of all of the genes contained in the pharmacokinetics and hormonal regulation (PK, H) sub-network of the ketamine pharmacogenomic network in the human brain.

Figures 42A, 42B, 42C:
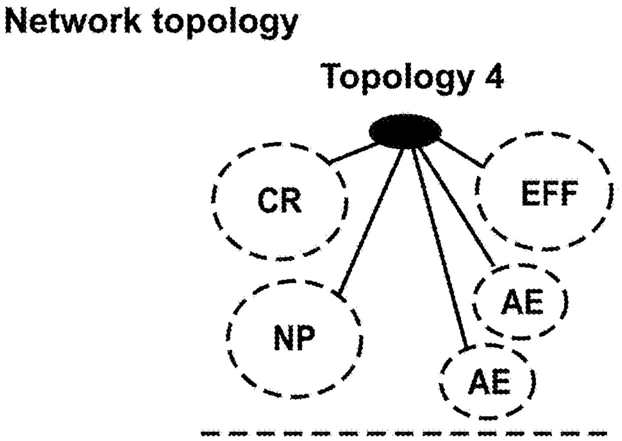
FIG. 42A illustrates the most significant disease annotations of the lithium pharmacogenomic network.
FIG. 42B illustrates the top 5 drugs that are upstream regulators of the lithium pharmacogenomic network.
FIG. 42C illustrates the topology model that most accurately fits the lithium pharmacogenomic network.

FIG. 42 shows the results of post-hoc bioinformatics analysis of the lithium pharmacogenomic network and its concomitant network topology model. FIG. 42A shows that the most significant disease annotations of the gene contained in the lithium pharmacogenomic network are cognitive impairment, mood disorders, drug-induced tremor, drug-induced weight gain, and schizophrenia.

FIG. 42B shows the most significant drugs that act as upstream regulators of the lithium pharmacogenomic network, including lithium chloride (p value=2.23E-23: Fisher's exact test), lithium (p=4.20E-19), and fluoxetine (p=2.94E-14).

FIG. 42C shows that the lithium pharmacogenomic network fits the model network topology label 4, with deconstructed gene set sub-networks that comprise chromatin remodeling (CR), neuroplasticity (NP), efficacy (EFF), adverse events (AE), and adverse events (AE). The non-CNS, peripheral systematic pharmacokinetic (SPK) sub-network of the lithium pharmacogenomic network cannot be determined from the output of this system.

FIG. 43 illustrates a high-resolution compartmentalization of gene set sub-networks as an example of the embodiment of a detailed output using this system for the lithium pharmacogenomic network.

FIG. 44 is a list of all of the genes contained in the chromatin remodeling (CR) sub-network of the lithium pharmacogenomic network in the human brain.

FIG. 45 is a list of all of the genes contained in the neuroplasticity (NP) sub-network of the lithium pharmacogenomic network in the human brain.

FIG. 46 is a list of all of the genes contained in the efficacy sub-network (EFF) of the lithium pharmacogenomic network in the human brain.

FIG. 47 is a list of all of the genes contained in the drug-induced tremor, adverse event (AE) sub-network of the lithium pharmacogenomic network in the human brain.

FIG. 48 is a list of all of the genes contained in the drug-induced weight gain, adverse event (AE) sub-network of the lithium pharmacogenomic network in the human brain.

Figures 49A, 49B, 49C:
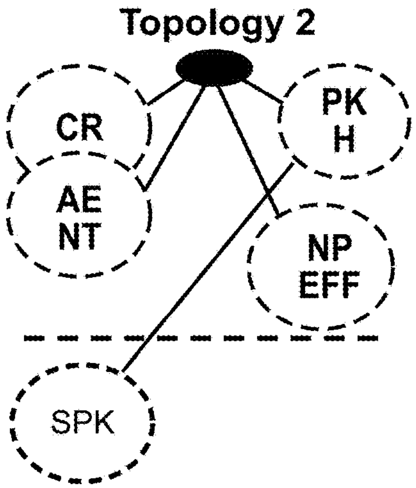
FIG. 49A illustrates the most significant disease annotations of the lamotrigine pharmacogenomic network.
FIG. 49B illustrates the top 5 drugs that are upstream regulators of the lamotrigine pharmacogenomic network.
FIG. 49C illustrates the topology model that most accurately fits the lamotrigine pharmacogenomic network.

FIG. 49 shows the results of post-hoc bioinformatics analysis of the lamotrigine pharmacogenomic network and its concomitant network topology model. FIG. 49A shows that the most significant disease annotations of the gene contained in the lamotrigine pharmacogenomic network are epilepsy, fibromyalgia, bipolar 1 disorder, mania, and treatment-resistant schizophrenia.

FIG. 49B shows the most significant drugs that act as upstream regulators of the lamotrigine pharmacogenomic network, including lamotrigine (p value=1.08E-10: Fisher's exact test), carbamazepine (p=3.51E-08), and mirtazapine (p=1.06E-07).

FIG. 49C shows that the lamotrigine pharmacogenomic network fits the model network topology label 2, with deconstructed gene set sub-networks that comprise chromatin remodeling (CR). adverse events (AE), and neurotransmission (NT), neuroplasticity and drug efficacy (NP, EFF), and pharmacokinetics and hormonal regulation (PK, H). The non-CNS, peripheral systematic pharmacokinetic (SPK) sub-network of the ketamine pharmacogenomic network cannot be determined from the output of this system.

Figure 50:
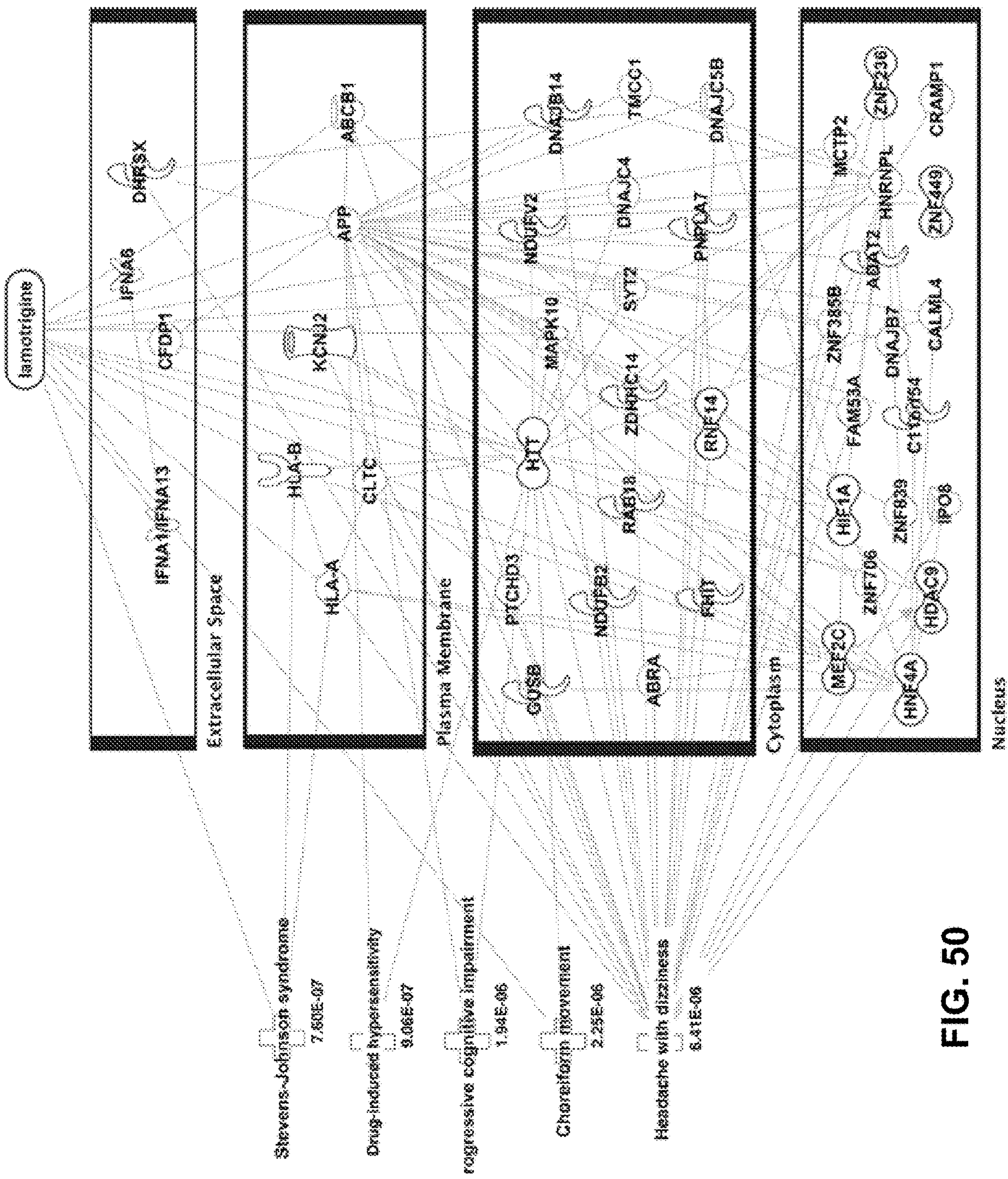
FIG. 50 illustrates an example of the lamotrigine pharmacogenomic adverse event sub-network as output by this system.

FIG. 50 illustrates the lamotrigine pharmacogenomic adverse event sub-network and post hoc bioinformatics analysis shows that the lamotrigine adverse event sub-network is significantly associated with Stevens-Johnson syndrome, drug-induced hypersensitivity, progressive cognitive impairment, choreiform movement and headache with dizziness.

Figure 51:
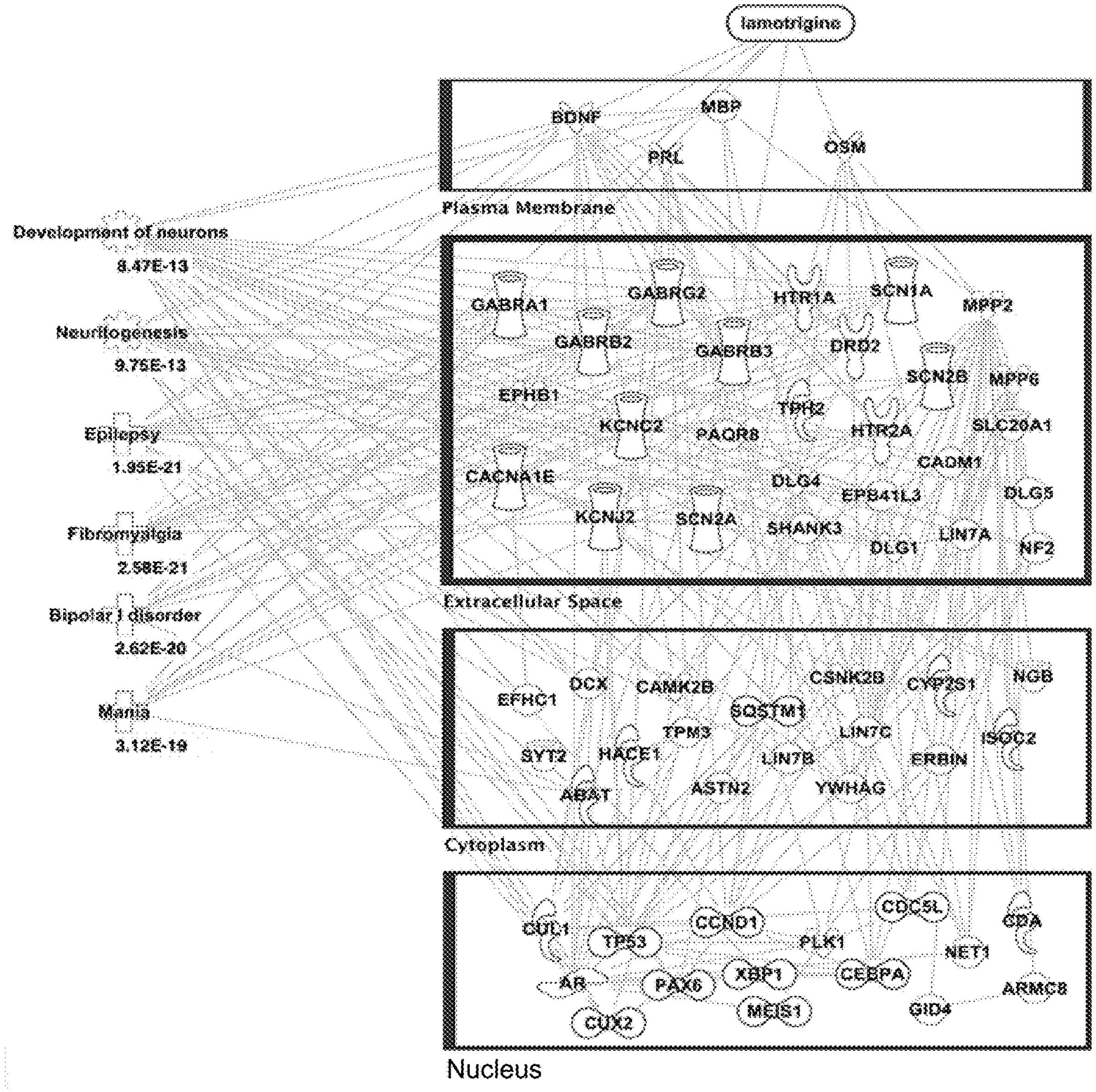
FIG. 51 illustrates an example of the lamotrigine pharmacogenomic neuroplasticity and efficacy sub-network as output by this system.

FIG. 51 illustrates the lamotrigine pharmacogenomic neuroplasticity sub-network and post hoc bioinformatics analysis shows that the lamotrigine pharmacogenomic neuroplasticity sub-network is significantly associated with development of neurons and neuritogenesis, as well as disease states including epilepsy, fibromyalgia, bipolar 1 disorder, and mania.

FIG. 52 is a list of all of the genes contained in the chromatin remodeling (CR) sub-network of the lamotrigine pharmacogenomic network in the human brain.

FIG. 53 is a list of all of the genes contained in the neuroplasticity and efficacy (NP, EFF) sub-network of the lamotrigine pharmacogenomic network in the human brain.

FIG. 54 is a list of all of the genes contained in the adverse event (AE) sub-network of the lamotrigine pharmacogenomic network in the human brain.

FIG. 55 is a list of all of the genes contained in the pharmacokinetics (PK) sub-network of the lamotrigine pharmacogenomic network in the human brain.

Figures 56A, 56B, 56C:
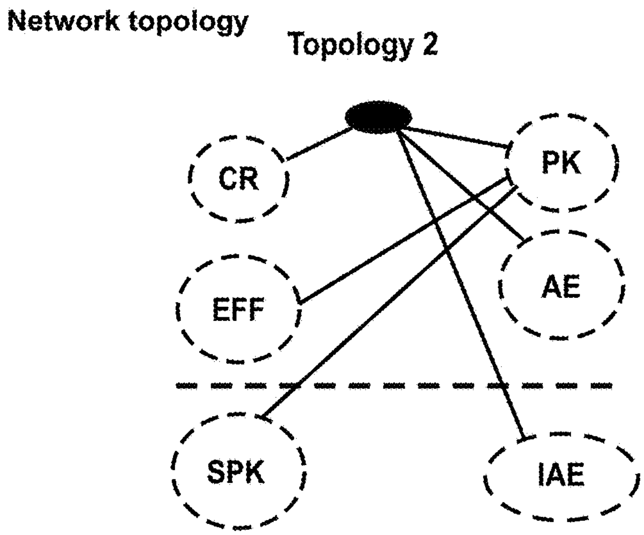
FIG. 56A illustrates the most significant disease annotations of the clozapine pharmacogenomic network.
FIG. 56B illustrates the top 5 drugs that are upstream regulators of the clozapine pharmacogenomic network.
FIG. 56C illustrates the topology model that most accurately fits the clozapine pharmacogenomic network.

FIG. 56 shows the results of post-hoc bioinformatics analysis of the clozapine pharmacogenomic network and its concomitant network topology model. FIG. 56A shows that the most significant disease annotations of the gene contained in the clozapine pharmacogenomic network are psychosis, agitation, bipolar spectrum disorder, non-affective psychosis, and treatment-resistant schizophrenia.

FIG. 56B shows the most significant drugs that act as upstream regulators of the clozapine pharmacogenomic network, including clozapine (p value=8.85E-110; Fisher's exact test), haloperidol (p=1.45E-42), and chlorpromazine (p=6.95E-20).

FIG. 56C shows that the clozapine pharmacogenomic network fits the model network topology label 3, with deconstructed gene set sub-networks that comprise chromatin remodeling (CR), adverse events, central nervous system (AE), pharmacokinetics (PK), and adverse events, peripheral immune system (IAE). The non-CNS. peripheral systematic pharmacokinetic (SPK) sub-network of the clozapine pharmacogenomic network cannot be determined from the output of this system.

Figure 57:
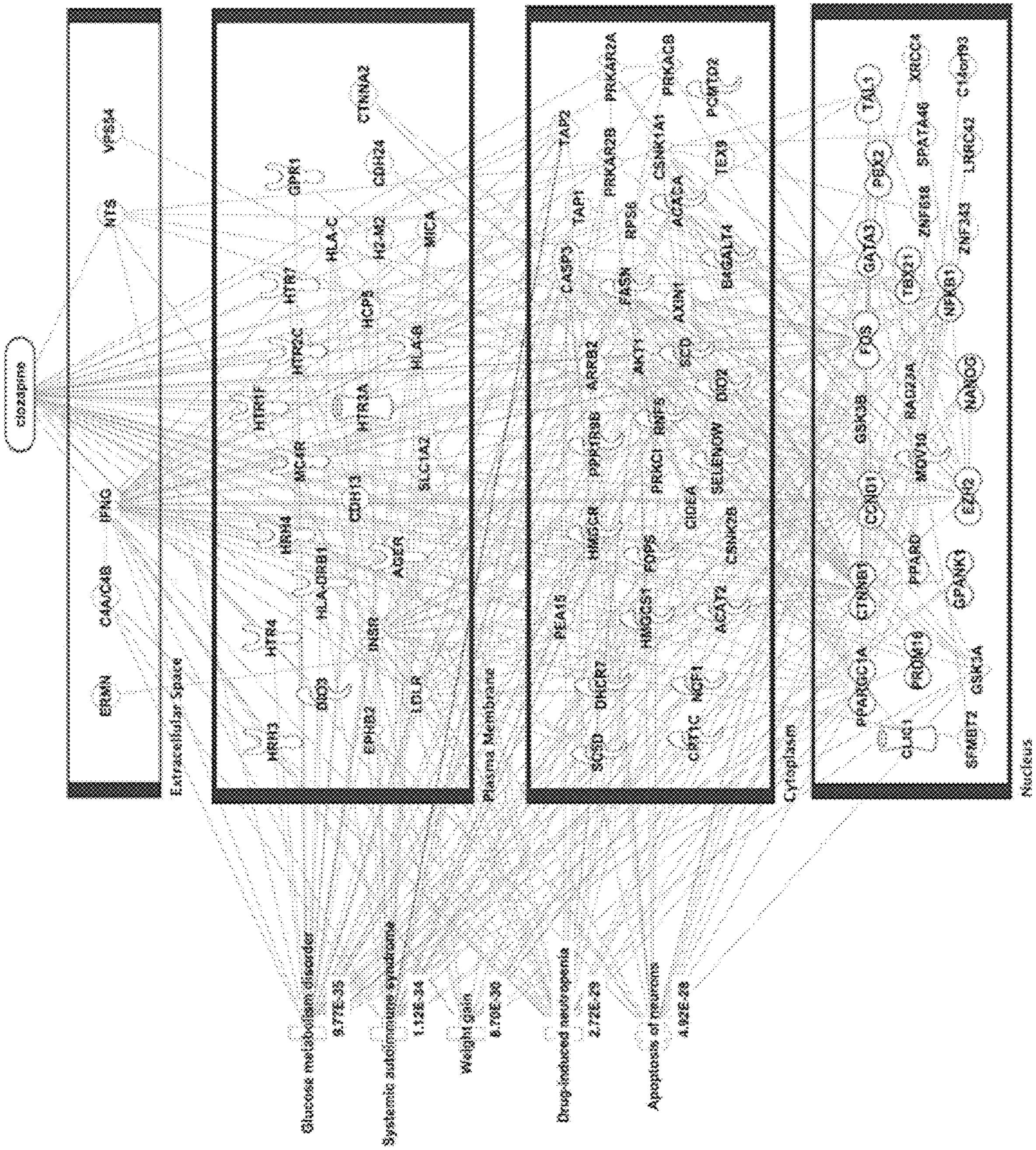
FIG. 57 illustrates an example of the clozapine pharmacogenomic adverse event sub-network as output by this system.

FIG. 57 illustrates the clozapine pharmacogenomic adverse event CNS and peripheral immune system adverse event sub-networks (AE, IAE), and post hoc bioinformatics analysis shows that the clozapine adverse event sub-network is significantly associated with glucose metabolism disorder, systemic autoimmune disorder, weight gain, drug-induced neutropenia, and apoptosis of neurons.

Figure 58:
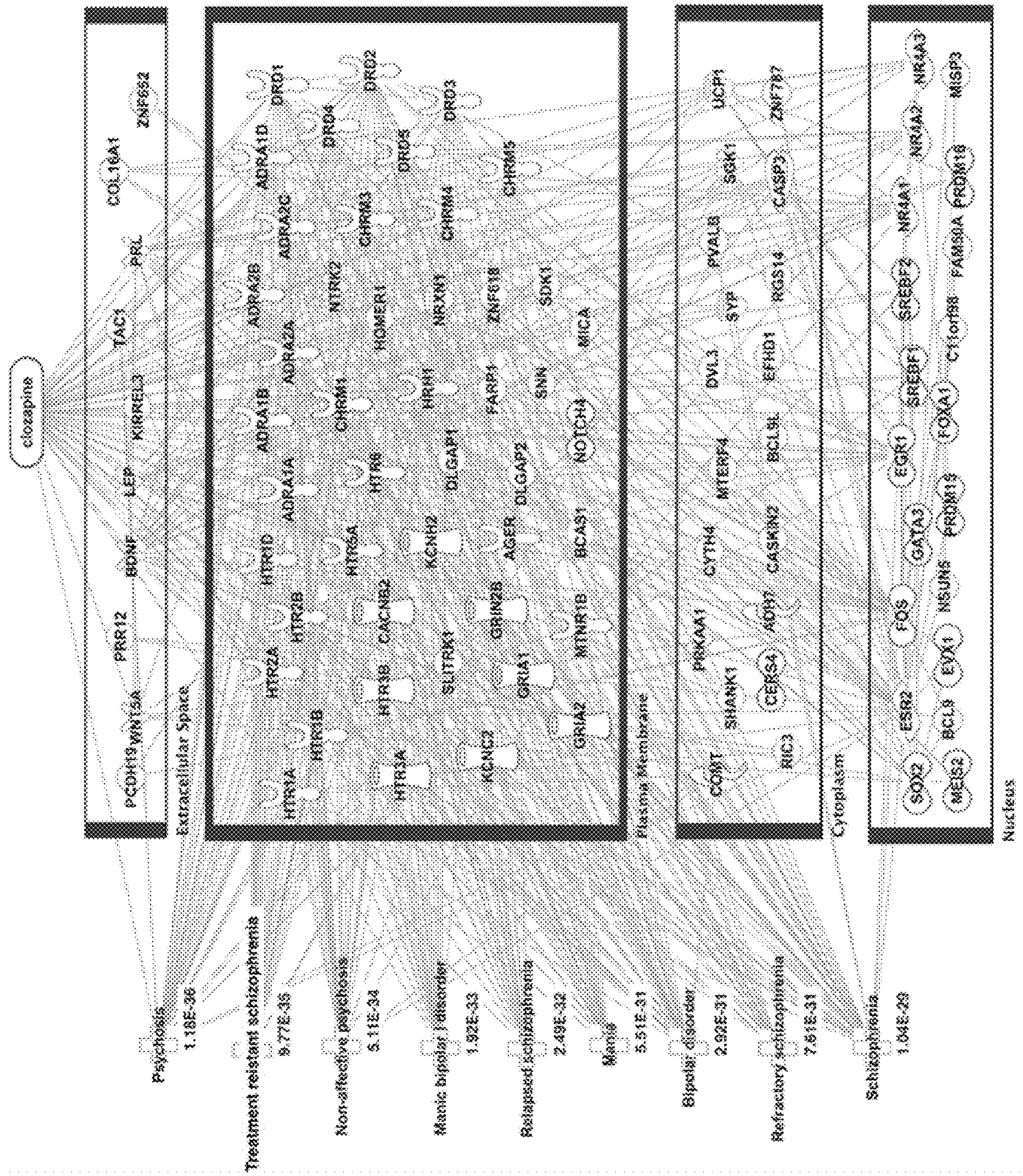
FIG. 58 illustrates an example of the clozapine pharmacogenomic neuroplasticity and efficacy sub-network as output by this system.
Figure 63A:
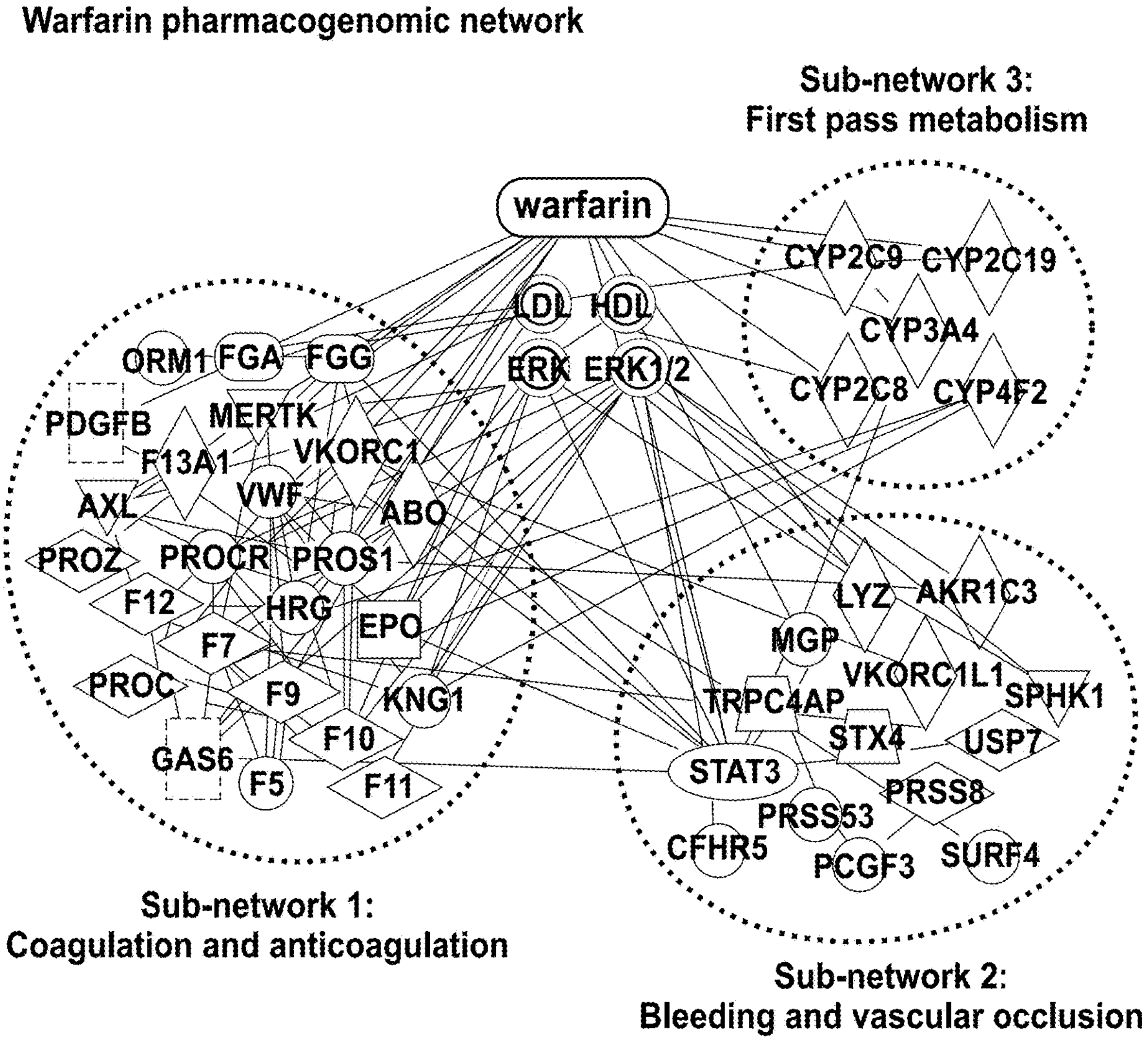
FIGS. 63A-63D illustrate the warfarin pharmacogenomic network which does not map to any of the network topologies of psychotropic medications as shown in FIG. 11. The warfarin pharmacogenomic network is illustrated in 63A and corresponding gene set enrichment characteristics shown in FIG. 63B.
Figure 63B:
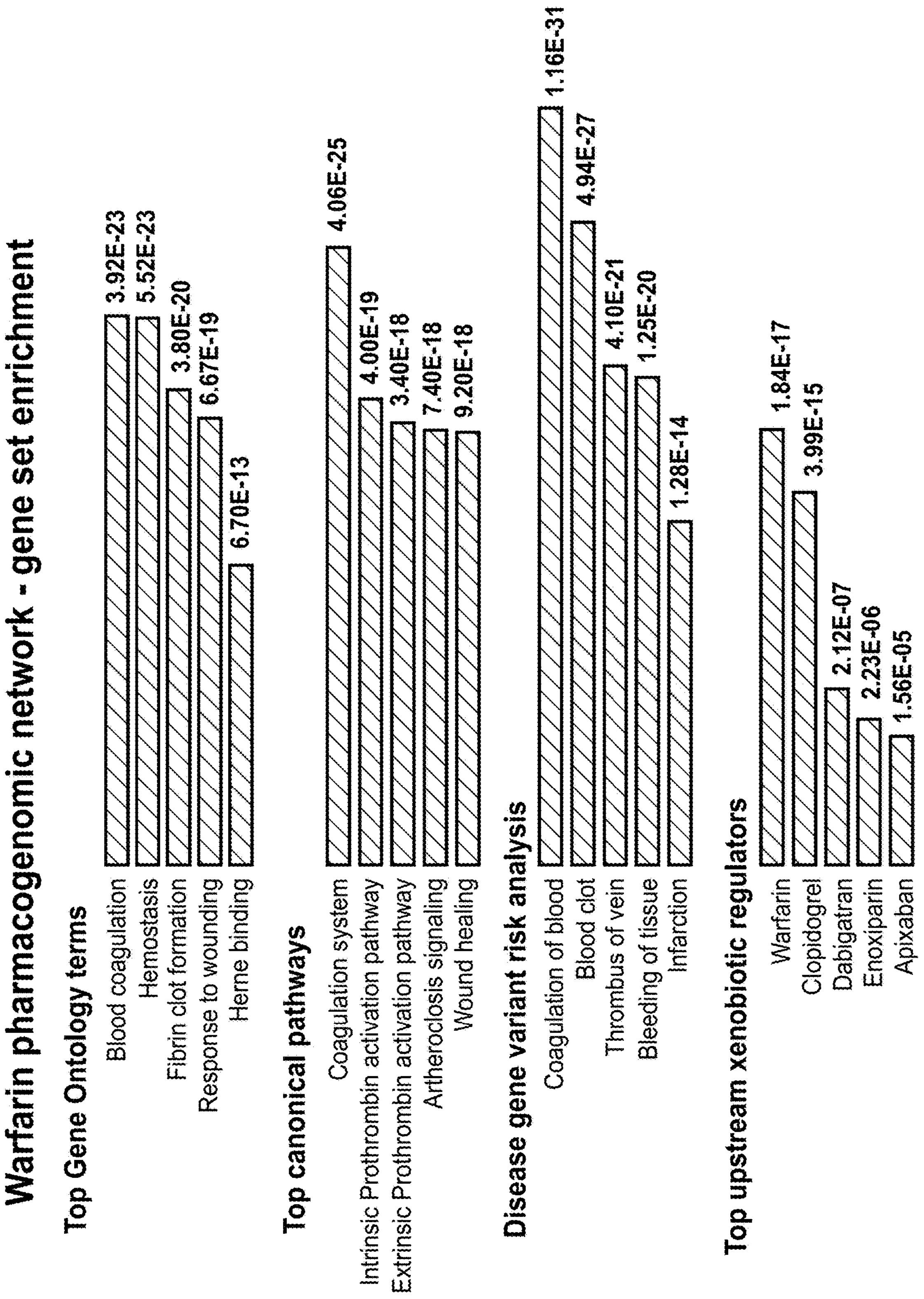
Figure 63C:
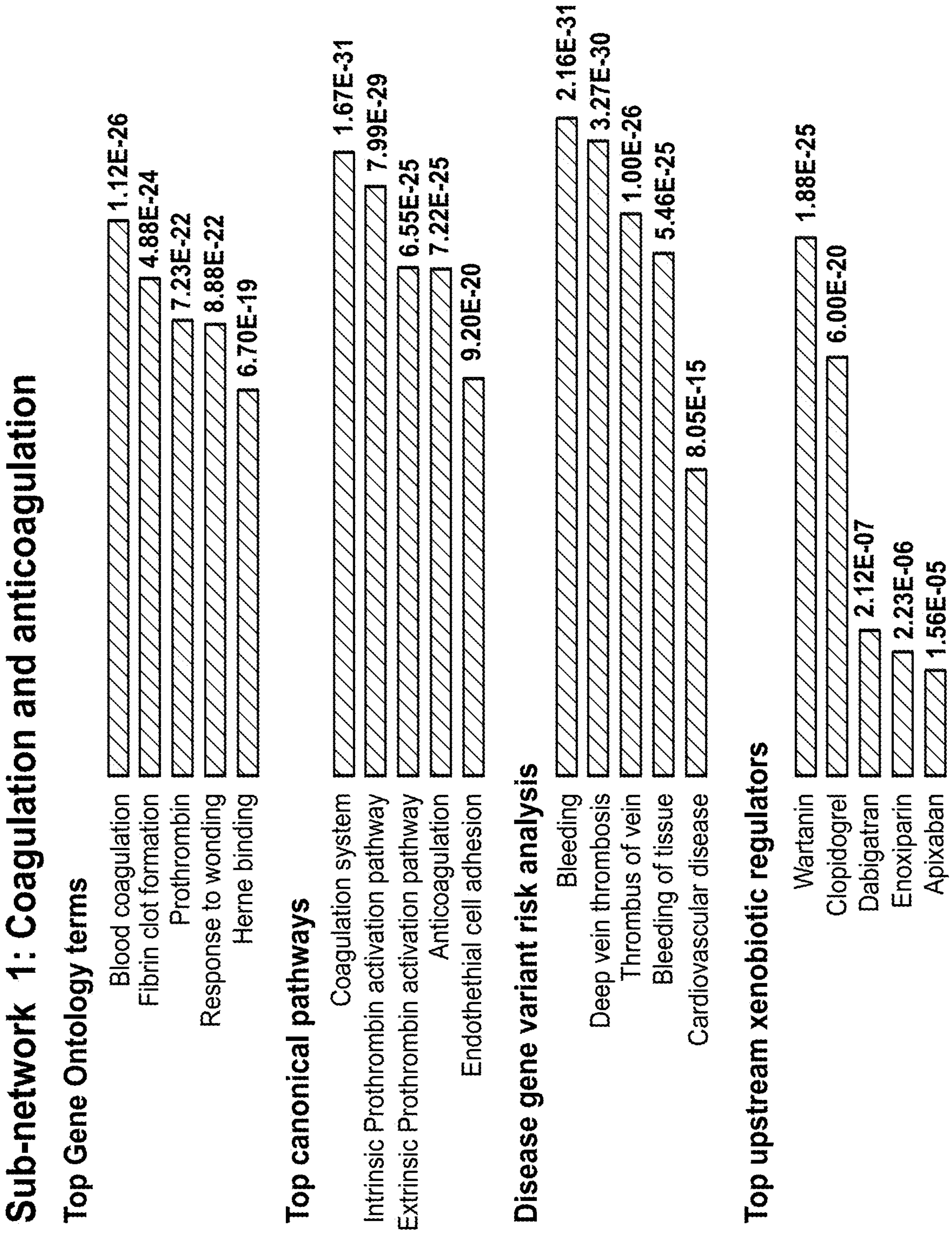
Figure 63D:
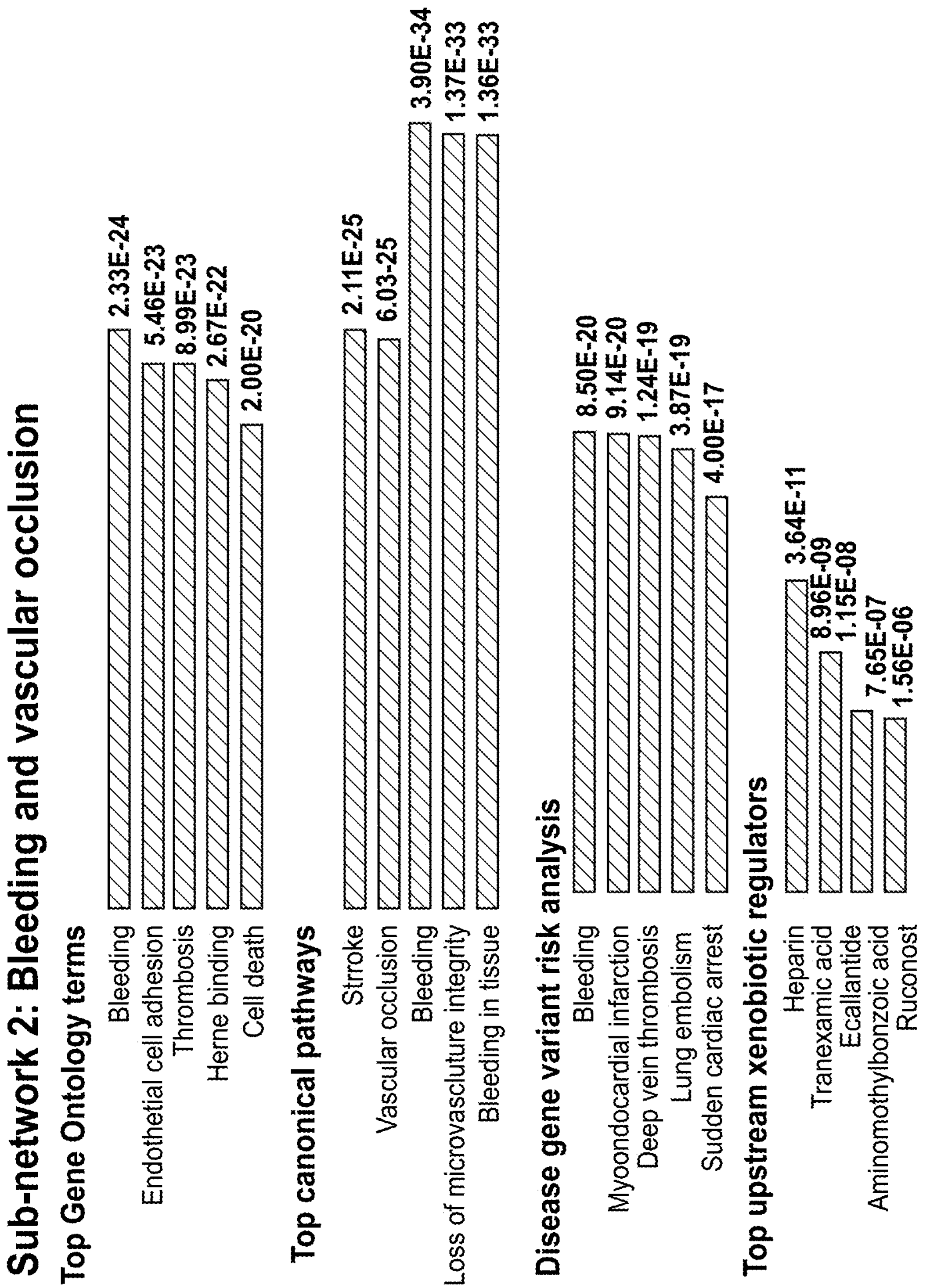

FIG. 58 illustrates the clozapine pharmacogenomic efficacy sub-network (EFF), and post hoc bioinformatics analysis shows that the clozapine efficacy sub-network is significantly associated with psychosis, treatment-resistant schizophrenia, non-affective psychosis, manic bipolar disorder, relapsed schizophrenia, mania, bipolar disorder, refractory schizophrenia, and schizophrenia.

FIG. 59 is a list of all of the genes contained in the chromatin remodeling (CR) sub-network of the clozapine pharmacogenomic network in the human brain.

FIG. 60 is a list of all of the genes contained in the efficacy (EFF) sub-network of the clozapine pharmacogenomic network in the human brain.

FIG. 61 is a list of all of the genes contained in the adverse event (AE) sub-network of the clozapine pharmacogenomic network in the human brain and in the peripheral immune system.

FIG. 62 is a list of all of the genes contained in the pharmacokinetics (PK) sub-network of the clozapine pharmacogenomic network in the human brain.

Another application of these methods is the identification of genes that encode novel, druggable molecules whose function is known, but was not known to be part of a drug efficacy sub-network of a class of medications that are of interest. As illustrated in FIG. 63, the warfarin pharmacogenomic network contains several candidate drug targets that were not previously known to be members of this drug's anticoagulant pharmacogenomic network. The method of pharmacogenomics network mapping using SNPs as part of drug pathway reconstruction enables the addition of the following genes as part of sub-network 1, which mediates the anticoagulant action of warfarin: AXL (AXL receptor tyrosine kinase), F9 (Coagulation factor IX), MERTK (MER proto-oncogene, tyrosine kinase), PDGFB (platelet derived growth factor subunit B), PROC (Protein C, inactivator of coagulation factors Va and VIIIa), PROCR (Protein C receptor), PROS) (Protein S) and PROZ (Protein Z, vitamin K dependent). Some of these novel genes may encode products that are druggable for use as an anticoagulant.

As shown in FIG. 63, the identified pharmacogenomic network for warfarin includes one or more of: ABO, alpha 1-3-N-acetylgalactosaminyltransferase and alpha 1-3-galactosyltransferase (ABO) gene, Aldo-keto reductase family 1 member C3 (AKR1C3) gene, AXL receptor tyrosine kinase (AXL) gene, Complement factor H related 5 (CFHRS) gene, cytochrome P450 family 2 subfamily C member 19 (CYP2C19) gene, Cytochrome P450 family 2 subfamily C member 8 (CYP2C8) gene, Cytochrome P450 family 2 subfamily C member 9 (CYP2C9) gene, Cytochrome P450 family 3 subfamily A member 4 (CYP3A4) gene, Cytochrome P450 family 4 subfamily F member 2

(CYP4F2) gene, Erythropoietin (EPO) gene, Coagulation factor V (F5) gene, Coagulation factor VII (F7) gene, Coagulation factor IX (F9) gene, Coagulation factor X (F10) gene, Coagulation factor XI (F11) gene, Coagulation factor XII (F12) gene, Coagulation factor XIII A chain (F13A1) gene, Fibrinogen alpha chain (FGA) gene, Fibrinogen gamma chain (FGG) gene, Growth arrest specific 6 (GAS6) gene, Histidine rich glycoprotein (HRG) gene, Kininogen 1 (KNG1) gene, Lysozyme (LYZ) gene, MER proto-oncogene, tyrosine kinase (MERTK) gene, Matrix Gla protein (MGP) gene, Orosomucoid 1 (ORM1) gene, Polycomb group ring finger 3 (PCGF3) gene, Platelet derived growth factor subunit B (PDGFB) gene, Protein C, inactivator of coagulation factors Va and VIIIa (PROC) gene, Protein C receptor (PROCR) gene, Protein S (PROS1) gene, Protein Z, vitamin K dependent plasma glycoprotein (PROZ) gene, Serine protease 8 (PRSS8) gene, Serine protease 53 (PRSS53) gene, Sphingosine kinase 1 (SPHK1) gene, Signal transducer and activator of transcription 3 (STAT3) gene, Syntaxin 4 (STX4) gene, Surfeit 4 (SURF4) gene, Transient receptor potential cation channel subfamily C member 4 associated protein (TRPC4AP) gene, Ubiquitin specific peptidase 7 (USP7) gene, Vitamin K epoxide reductase complex subunit 1 (VKORC1) gene, Vitamin K epoxide reductase complex subunit 1 like 1 (VKORC1L1) gene, or von Willebrand factor (VWF) gene.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as providing examples only and does not describe every possible embodiment, as describing every possible embodiment would be impractical, if not impossible. One could implement numerous alternate embodiments, using either current technology or technology developed after the filing date of this application.

We claim:

1. A method for identifying a pharmacogenomic network of a drug, the method comprising:

obtaining, by one or more processors, a plurality of single nucleotide polymorphisms (SNPs) correlated with drug response or adverse events for a particular drug;

performing, by the one or more processors, a mapping of 3D spatial connections using the plurality of SNPs as probes within chromatin data to determine interconnections between target genes correlated with drug response or adverse events for the particular drug;

identifying, by the one or more processors, a drug pharmacogenomic network for the particular drug based on the target genes;

deconstructing, by the one or more processors, the drug pharmacogenomic network into a plurality of drug pharmacogenomic sub-networks;

obtaining a biological sample of a patient;

comparing SNPs within the biological sample to SNPs correlated with drug response the drug pharmacogenomic network or one or more of the plurality of drug pharmacogenomic sub-networks; and administering the particular drug to the patient when the drug is identified as one that would be effective in the patient based on the comparison.

2. The method of claim 1, wherein identifying a drug pharmacogenomic network for the particular drug based on the target genes includes:

comparing, by the one or more processors, the plurality of SNPs to a database of SNPs to identify additional SNPs that are linked to the plurality of SNPs using a topologically associating domain (TAD) boundary within a chromosome territory, wherein the plurality of SNPs and additional SNPs are included in a set of candidate variants, wherein the mapping of the 3D spatial connections is performed using the candidate variants;

performing, by the one or more processors, a pathway analysis on the target genes associated with the set of candidate variants to filter the target genes to identify a set of genes which are causally related to the particular drug; and identifying, by the one or more processors, the drug pharmacogenomic network for the particular drug based on the identified set of genes.

3. The method of claim 2, further comprising:

performing, by the one or more processors, a bioinformatics analysis on the drug pharmacogenomic network to ensure a most significantly associated drug to the plurality of drug pharmacogenomic sub-networks is the particular drug.

4. The method of claim 3, wherein performing a bioinformatics analysis on the drug pharmacogenomic network includes:

validating, via bioinformatics, the drug pharmacogenomic network and the plurality of drug pharmacogenomic sub-networks for the particular drug.

5. The method of claim 4, wherein validating the drug pharmacogenomic network and the plurality of drug pharmacogenomic sub-networks for the particular drug includes:

comparing the drug pharmacogenomic network and the plurality of drug pharmacogenomic sub-networks for the particular drug to one or more of:

terms from a gene ontology or medications database, canonical biological pathway in cells or tissues where the particular drug acts, or xenobiotic upstream regulators in the cells or the tissues where the particular drug acts.

6. The method of claim 2, wherein performing a pathway analysis on target genes associated with the set of candidate variants to filter the target genes includes identifying, by the one or more processors, a set of candidate drug pharmacogenomic network genes by identifying a subset of the target genes that form a statistically significant interconnected pathway expressed in a tissue associated with the particular drug.

7. The method of claim 6, further comprising:

analyzing each gene in the set of candidate drug pharmacogenomic network genes according to at least one of: a function of the gene in context of the particular drug, a set of mutations within the gene, or a pattern of expression of the gene relative to a neuroanatomical substrate, as defined by RNA expression data, functional imaging, or other integrative multiscale data indicating where the particular drug is known to act;

analyzing other genes and functional genomic elements including long noncoding RNA based on each gene in the set of candidate drug pharmacogenomic network genes; and adding or removing genes to or from the set of candidate drug pharmacogenomic network genes based on the analysis.

8. The method of claim 7, wherein analyzing each gene in the set of candidate drug pharmacogenomic network genes according to a pattern of expression of the gene relative to a neuroanatomical substrate includes:

comparing each gene in the set of candidate drug pharmacogenomic network genes to a neuromap indicating the neuroanatomical substrate for the particular drug; and filtering genes from the set of candidate drug pharmacogenomic network genes that are not expressed in a same neuroanatomical region as the particular drug.

9. The method of claim 1, further comprising:

determining, by the one or more processors, one or more spatial contacts including TADs based on the plurality of single nucleotide polymorphisms (SNPs) correlated with drug response or adverse events for the particular drug, wherein the one or more spatial contacts are differentially expanded and suppressed.

10. The method of claim 1, wherein the drug pharmacogenomic network includes one of more defining characteristics of functional spatial genomics, including at least one of:

mutations that impact enhancer-promoter pairs, promoter-promoter pairs, super enhancer-promoter pairs, regulatory RNAs, euchromatin or heterochromatin state, topologically-associating domains (TADs), or lamina-associating domains (LADs).

11. The method of claim 1, further comprising:

storing, by the one or more processors, the indication of the drug pharmacogenomic network and indications of the plurality of drug pharmacogenomic sub-networks for the particular drug in a database as a reference set to compare and score input patient pharmacogenomic networks for the same particular drug to determine efficacy and adverse events when treating the patient for a condition or disease.

12. The method of claim 1, further comprising:

identifying, by the one or more processors, a set of molecular pharmacodynamic targets within one of the plurality of drug pharmacogenomic sub-networks for a same or similar clinical indication as the specified drug.

13. The method of claim 12, wherein the set of molecular pharmacodynamic targets within one of the plurality of drug pharmacogenomic sub-networks and the particular drug act in a human brain, and a majority of members of a pathway for the molecular pharmacodynamic target are expressed in the same regions of the human brain as the particular drug.

14. The method of claim 1, further comprising:

re-purposing a drug based on underlying loci of pharmacogenomic enhancer SNPs related to the plurality of drug pharmacogenomic sub-networks within the topology of sub-network types.

15. The method of claim 1, further comprising:

re-purposing a combination of drugs to test as a therapeutic after determination that physiological mechanisms demonstrate that complementarity between sub-network characteristics of two or more drugs offers a more optimal therapy for a particular disease or disease states than a single particular drug.

16. The method of claim 15, wherein re-purposing a combination of drugs includes re-purposing valproic acid and ketamine as a combinatorial therapeutic for neurological and neuropsychiatric disorders.

17. The method of claim 1, wherein the particular drug is one of: valproic acid, ketamine, lithium, lamotrigine, clozapine, or warfarin.

* * * * *